US008916172B2

(12) United States Patent
Moss et al.

(10) Patent No.: US 8,916,172 B2
(45) Date of Patent: *Dec. 23, 2014

(54) MVA EXPRESSING MODIFIED HIV ENVELOPE, GAG, AND POL GENES

(75) Inventors: Bernard Moss, Bethesda, MD (US); Linda Wyatt, Rockville, MD (US); Patricia Earl, Chevy Chase, MD (US); Harriet L. Robinson, Atlanta, GA (US)

(73) Assignees: Emory University, Atlanta, GA (US); National Institute of Allergy and Infectious Diseases (NIAID), Bethesda, MD (US); The United States of America, as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/987,791

(22) Filed: Jan. 10, 2011

(65) Prior Publication Data

US 2011/0104199 A1    May 5, 2011

Related U.S. Application Data

(63) Continuation of application No. 12/018,150, filed on Jan. 22, 2008, now Pat. No. 7,867,982, which is a continuation of application No. 10/646,628, filed on Aug. 22, 2003, now abandoned, which is a continuation of application No. PCT/US02/06713, filed on Mar. 1, 2002.

(60) Provisional application No. 60/274,434, filed on Mar. 8, 2001.

(51) Int. Cl.
| A61K 39/285 | (2006.01) |
| C12N 7/04 | (2006.01) |
| A61P 31/18 | (2006.01) |
| A61P 37/04 | (2006.01) |
| A61K 39/21 | (2006.01) |
| C07K 14/005 | (2006.01) |
| C12N 15/86 | (2006.01) |
| A61K 39/00 | (2006.01) |

(52) U.S. Cl.
CPC ........... *C12N 15/86* (2013.01); *A61K 2039/525* (2013.01); *C12N 2830/15* (2013.01); *C12N 2830/60* (2013.01); *C12N 2740/16222* (2013.01); *C12N 2710/24143* (2013.01); *A61K 39/21* (2013.01); *A61K 2039/57* (2013.01); *C12N 2710/24171* (2013.01); *A61K 2039/53* (2013.01); *C07K 14/005* (2013.01); *C12N 2830/00* (2013.01); *C12N 2740/15022* (2013.01); *C12N 2740/16122* (2013.01)
USPC ...................... 424/199.1; 435/236

(58) Field of Classification Search
None
See application file for complete search history.

(56) References Cited

U.S. PATENT DOCUMENTS

| 5,169,763 | A | 12/1992 | Kieny et al. |
| 5,185,146 | A | 2/1993 | Altenburger |
| 5,256,767 | A | 10/1993 | Salk et al. |
| 5,445,953 | A | 8/1995 | Dorner et al. |
| 5,494,807 | A | 2/1996 | Paoletti et al. |
| 5,589,466 | A | 12/1996 | Felgner et al. |
| 5,593,972 | A | 1/1997 | Weiner et al. |
| 5,614,404 | A | 3/1997 | Mazzara et al. |
| 5,676,950 | A | 10/1997 | Small et al. |
| 5,736,368 | A | 4/1998 | Mazzara et al. ........... 435/320.1 |
| 5,741,492 | A | 4/1998 | Hurwitz et al. |
| 5,747,324 | A | 5/1998 | Mazzara et al. |
| 5,747,338 | A | 5/1998 | Giese et al. |
| 5,756,103 | A | 5/1998 | Paoletti et al. ............. 424/160.1 |
| 5,766,599 | A | 6/1998 | Paoletti et al. .................... 435/5 |
| 5,795,577 | A | 8/1998 | Kieny et al. ................ 424/208.1 |
| 5,817,637 | A | 10/1998 | Weiner et al. ................. 435/456 |
| 5,846,946 | A | 12/1998 | Huebner et al. ................ 514/44 |
| 5,849,304 | A | 12/1998 | Moss et al. |
| 5,853,725 | A | 12/1998 | Salk et al. .................. 424/208.1 |
| 5,858,775 | A | 1/1999 | Johnson ..................... 435/320.1 |
| 5,863,542 | A | 1/1999 | Paoletti et al. |
| 5,879,925 | A | 3/1999 | Rovinski et al. |
| 5,911,989 | A | 6/1999 | Katinger et al. ........... 424/160.1 |
| 5,928,930 | A | 7/1999 | Salk et al. |
| 5,985,641 | A | 11/1999 | Haynes et al. |
| 6,051,410 | A | 4/2000 | Mazzara et al. |
| 6,077,662 | A | 6/2000 | Compans et al. ................. 435/5 |
| 6,080,408 | A | 6/2000 | Rovinski et al. |
| 6,086,891 | A | 7/2000 | Hurwitz et al. |
| 6,099,847 | A | 8/2000 | Tobin et al. |
| 6,103,244 | A | 8/2000 | Dorner et al. |
| 6,121,021 | A | 9/2000 | Rovinski et al. |
| 6,140,114 | A | 10/2000 | Klatzmann et al. |
| 6,156,952 | A | 12/2000 | Bryant et al. .................... 800/11 |

(Continued)

FOREIGN PATENT DOCUMENTS

| EP | 335 635 | 3/1989 |
| EP | 0 538 496 | 8/1991 |

(Continued)

OTHER PUBLICATIONS

Andersson et al., Cloning, Structure, and Expression of the Mitochondrial Cytochrome . . . J. of Biol. Chem. 264(14):8222-8229, 1989.

Belyakov et al., "Induction of a Mucosal Cytotoxic T-Lymphocyte Response by . . . " J. of Virology 72(1):8264-8272, 1998.

Cheonis, N., "Status Report on HIV Vaccine Development" Status Report on HIV Vaccine Development retrieved from internet >http://www.thebody.com/sfaf/winter00/vaccine.html. Oct. 2001.

Davison et al., "Structure of Vaccinia Virus Early Promoters" J. Mol. Biol. 210:749-769, 1989.

(Continued)

*Primary Examiner* — Robert A Zeman
(74) *Attorney, Agent, or Firm* — King & Spalding

(57) ABSTRACT

The invention provides modified virus Ankara (MVA), a replication-deficient strain of vaccinia virus, expressing human immunodeficiency virus (HIV) env, gag, and pol genes.

4 Claims, 63 Drawing Sheets

(56) References Cited

U.S. PATENT DOCUMENTS

| | | | |
|---|---|---|---|
| 6,171,596 B1 | 1/2001 | Earl et al. | |
| 6,204,250 B1 | 3/2001 | Bot et al. | |
| 6,214,804 B1 | 4/2001 | Felgner et al. | |
| 6,221,633 B1 | 4/2001 | Ertl et al. | |
| 6,265,183 B1 | 7/2001 | Dorner et al. | |
| 6,291,157 B1 | 9/2001 | Rovinski et al. | |
| 6,306,625 B1 | 10/2001 | Jacobs et al. | |
| 6,448,083 B1 | 9/2002 | Larocca et al. | 435/456 |
| 6,544,527 B1 | 4/2003 | Rovinski et al. | 424/208.1 |
| 6,663,871 B1 | 12/2003 | McMichael et al. | |

FOREIGN PATENT DOCUMENTS

| | | |
|---|---|---|
| WO | WO89/09260 | 10/1989 |
| WO | WO 89/12095 | 12/1989 |
| WO | WO 91/07425 | 5/1991 |
| WO | WO 92/08789 | 5/1992 |
| WO | WO 97/27311 | 7/1997 |
| WO | WO 98/56919 | 12/1998 |
| WO | WO 99/63098 | 12/1999 |
| WO | WO 00/00216 | 1/2000 |
| WO | WO 01/47955 | 7/2000 |
| WO | WO 01/02607 | 1/2001 |
| WO | WO 01/52886 | 7/2001 |
| WO | WO 01/82962 | 11/2001 |
| WO | WO 01/92470 | 12/2001 |
| WO | WO 02/072754 | 9/2002 |
| WO | WO 03/004657 | 1/2003 |

OTHER PUBLICATIONS

Hanke et al., "Enhancement of MHC class I-restricted peptide-specific T cell induction . . . " Vaccine 16(5):439-445, 1998.
Hanke et al., "Lack of toxicity and persistence in the mouse associated with administration of candidate . . . " Vaccine 21:108-114, 2002.
Hanke et al., "Development of a DNA-MVA/HIVA vaccine for Kenya" Vaccine 20:1995-1998, 2002.
Hanke et al., "Pre-clinical development of a mutli-CTL epitope-based DNA prime MVA boost vaccine for AIDS" Immunology Letters 66:177-181, 1999.
Hanke et al., "Effective induction of HIV-specific CTL by multi-epitope using gene gun . . . " Vaccine 17:589-596, 1999.
Hanke et al., "Immunogenicities of intravenous and intramuscular administrations of modified vaccinia . . . " J. of General Virology 79:83-90, 1998.
Haffar et al., "The Carboxy Terminus of Human Immunodeficiency Virus Type I gp160 . . . " J. of Virology 64(6):3100-3103, 1990.
Ho, M., "Aids Vaccines Trials Dangerous" retrieved from internet http://www.i-sis.org.uk/isisnews/i-sisnews11-19.php. Oct. 2001.
Masternak et al., "cis- and trans-Acting Elements Involved in Reactivation of Vaccinia Virus Early Transcription" J. of Virology 70(12):8737-8746, 1996.
Wee et al., "A DNA/MVA-based candidate human immunodeficiency virus vaccine for Kenya induces . . . " J. of General Virology 83:75-80, 2002.
Wyatt et al., "Development of a replication-deficient recombinant vaccinia virus vaccine effective against . . . " Vaccine 14(15):1451-1458, 1996.
Wyatt et al., "Priming and boosting immunity to respiratory syncytial virus by recombinant replication-defective . . . " Vaccine 18:392-397, 2000.
Amara et al., "Different Patterns of Immune Responses but Similar Control of a Simian-Human Immunodeficiency Virus 89.6P Mucosal Challenge by Modified Vaccinia Virus Ankara (MVA) and DNA/MVA Vaccines," *J. Virology* 76:7625-7631 (2002).
Andre et al., "Increased immune response elicited by DNA vaccination with a synthetic gp120 sequence with optimized codon usage," J. Virol., 72: 1497-1503, 1998.
Antoine et al., "The Complete Genomic Sequence of the Modified Vaccinia Ankara Strain: Comparison with Other Orthopoxviruses", Virology, 244: 365-96, 1998.

Asakura et al., "Induction of HIV-1 specific mucosal immune responses by DNA vaccination," Scand. J. Immunol., 46: 326-330, 1997.
Bachmann and Zinkernagel, "Neutralizing antiviral B cell responses," in Ann. Rev. Immunol., 15: 235-270, 1997.
Barouch et al., "Reduction of Simian-human immunodeficiency virus 89.6P viremia in rhesus monkeys by recombinant modified vaccinia virus Ankara vaccination," J. Virol., 75: 5151-5158, 2001.
Barouch et al., "Augmentation of immune responses to HIV-1 and simian immunodeficiency virus DNA caccines by IL-2/IG plasmid administration in rhesus monkeys", Proc. Natl. Acad. Sci. U.S.A., 97:4192-7, Apr. 11, 2000.
Barry et al., "Protection against mycoplasma infection using expression-library immunization," Nature, 377: 632-635, 1995.
Berger, "HIV Entry and Tropism: the chemokine receptor connection," AIDS, 11(Suppl. A): S3-16, 1997.
Benson et al., J. Virol., "Recombinant vaccine-induced protection against the highly pathogenic simian immunodeficiency virus SIV(mac251): dependence on route of challenge exposure," 72: 4170-4182, 1998.
Blanchard et al., "Modified vaccinia virus Ankara undergoes limited replication in human cells and lacks several immunomodulatory proteins: implications for use as a human vaccine," J. Gen. Virol., 79: 1159-1167, 1998.
Bohm et al., "DNA vector constructs that prime hepatitis B surface antigen-specific cytotoxic T lymphocyte and antibody responses in mice after intramuscular injection," J. Immuno. Methods, 193: 29-40, 1996.
Bohm et al., "Routes of plasmid DNA vaccination that prime murine humoral and cellular immune responses," Vaccine, 16: 949-54, 1998.
Bolivar et al., "Construction and Characterization of New Cloning Vehicles: (II. A Multipurpose Cloning System)," Gene, 2: 95-113, 1977.
Boyer et al., "Protection of chimpanzees from high-dose heterologous HIV-1 challenge by DNA vaccination," Nature Med., 3: 526-532, 1997.
Boyle et al., "Influence of cellular location of expressed antigen on the efficacy of DNA vaccination: cytotoxic T lymphocyte and antibody responses are suboptimal when antigen is cytoplasmic after intramuscular DNA immunization," Int. Immunol., 9: 1897-1906, 1997.
Boyle et al., "Enhanced responses to a DNA vaccine encoding a fusion antigen that is directed to sites of immune induction," Nature, 392: 408-411, 1998.
Burton and Montefiori, "The antibody response in HIV-1 infection," AIDS, 11(Suppl A):S87-98, 1997.
Burton et al., "Why do we not have an HIV vaccine and how can we make one?" Nature Med. 4:495-498, 1998.
Calarota et al., "Cellular cytotoxic response induced by DNA vaccination in HIV-1-infected patients," Lancet, 351: 1320-1325, 1998.
Cardoso et al., "Immunization with Plasmid DNA Encoding for the Measles Virus Hemagglutinin and Nucleoprotein Leads to Humoral and Cell-Mediated Immunity," Virology, 225: 293-299, 1998.
Carroll and Moss, "Host Range and Cytopathogenicity of the Highly Attenuated MVA Strain of Vaccina Virus: Propagation and Generation of Recombinant Viruses in a Nonhuman Mammalian Cell Line", Virology, 238:198-211, 1997.
Chapman et al., "Effect of intron A from human cytomegalovirus (Towne) immediate-early gene on heterologous expression in mammalian cells," Nucl. Acids Res., 19: 3979-3986, 1991.
Chen et al., "Protective Immunity Induced by Oral Immunization with a Rotavirus DNA Vaccine Encapsulated in Microparticles," J. Virol., 72: 5757-5761, 1998.
Chun et al., "Early establishment of a pool of latently infected, resting CD4+ T cells during primary HIV-1 infection," Proc. Natl. Acad. Sci. USA, 95: 8869-8873, 1998.
Collman et al., "An Infection Molecular Clone of an Unusual Microphage-Tropic and Highly Cytopathic Strain of Human Immunodeficiency Virus Type 1," J. Virol., 66: 7517-7521, 1992.
Condon et al., "DNA-based immunization by in vivo transfection of dendritic cells," Nat Med., 2:1122-1128, 1996.
Corr et al., "Gene Vaccination with Naked Plasmid DNA: Mechanism of CTL Priming," J. Exp. Med., 184: 1555-1560, 1996.

(56) References Cited

OTHER PUBLICATIONS

Dempsey et al., C3d of Complement as a Molecular Adjuvant: Bridging Innate and Acquired Immunity, Science, 271: 348-350, 1996.
Durbin et al., "Comparison of the immunogenicity and efficacy of a replication-defective vaccinia virus expressing antigens of human parainfluenza virus type 3 (HPIV3) with those of a live attenuated HPIV3 vaccine candidate in rhesus monkeys passively immunized with PIV3 antibodies," J. Infect. Dis., 179: 1345-1351, 1999.
Durbin et al., "The immunogenicity and efficacy of intranasally or parenterally administered replication-deficient vaccinia-parainfluenza virus type 3 recombinants in rhesus monkeys", Vaccine, 16: 1324-30, 1998.
Endo et al., "Short- and Long-term Clinical Outcomes in Rhesus Monkeys Inoculated with a Highly Pathogenic Chimeric Simian/Human Immunodeficiency Virus", J. Virol., 74:6935-45, 2000.
Esparza and Bhamarapravati, "Accelerating the development and future availability of JIV-1 vaccines: why, when, where, and how?", Lancet, 355: 2061-6, 2000.
Evans DT et al., "Virus-specific T-lymphocyte responses select for amino-acid variation in simian immunodeficiency virus Env and Nef," Nat. Med., 5: 1270-1276, 1999.
Feltquate et al., "Different T Helper Cell Types and Antibody Isotypes Generated by Saline and Gene Gun DNA Immunization," J. Immunol. 158: 2278-2284, 1997.
Feinberg et al., "AIDS vaccine models" Challenging challenge viruses Nature Med. 8(3):207-210, 2002.
Finzi at al., "Latent infection of CD4 T cells provides a mechanism for lifelong persistence of HIV-1, even in patients on effective combination therapy", Nat. Med. 5: 1270-6, 1996.
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand. J. Immunol., 47: 289-295, 1998.
Fu et al., "Priming of Cytotoxic T Lymphocytes by DNA Vaccines: Requirement for Professional Antigen Presenting Cells and Evidence for Antigen Transfer from Myocytes," Mol. Med., 3: 362-371, 1997.
Furci et al., "Antigen-driven C-C Chemokine-mediated HIV-1 Suppression by CD4 T Cells from Exposed Uninfected Individuals Expressing the Wild-type CCR-5 Allele", J. Exp. Med., 186:455-60, 1997.
Fynan et al., "DNA vaccines: Protective immunizations by parenteral, mucosal, and gene-gun inoculations," Proc. Natl. Acad. Sci. USA, 90: 11478-11482, 1993.
Hakim et al., "A Nine-Amino Acid Peptide from IL-1β Augments Antitumor Immune Responses Induced by Protein and DNA Vaccines," J. Immunol., 157: 5503-5511, 1996.
Hanke at al., "DNA multi-CTL epitope vaccines for HIV and *Plasmodium faciparum:* immunogenicity in mice," Vaccine, 16: 426-435, 1998b.
Hartikka et al., "An Improved Plasmid DNA Expression Vector for Direct Injection into Skeletal Muscle," Hum. Gen. Therapy, 7: 1205-1217, 1996.
Hirsch et al., "Prolonged Clinical Latency and Survival of Macaques Given a Whole Inactivated Simian Immunodeficiency Virus Vaccine", J. Infect. Dis., 170:51-9, 1994.
Huang et al., "Human Immunodeficiency Virus Type 1-Specific Immunity . . . " J. of Virology 75:4947-4951, 2001.
Inchauspe et al., "Plasmid DNA Expressing a Secreted or a Nonsecreted Form of Hepatitis C Virus Nucleocapsid: Comparative Studies of Antibody and T-Helper Responses Following Genetic Immunization," DNA Cell Biol., 16: 185-195, 1997.
Iwasaki at al., "Enhanced CTL responses mediated by plasmid DNA immunogens encoding costimulatory molecules and cytokines," J. Immunol., 158: 4591-4601, 1997a.
Iwasaki et al., "The dominant role of bone-marrow derived cells in CTL induction following plasmid DNA immunization at different sites," J. Immunol., 159: 11-14, 1997b.

Jacobsen et al., "Characterization of Human Immunodeficiency Virus Type 1 Mutants with Decreased Sensitivity to Proteinase Inhibitor Ro 31-8959," *J. Virology* 206:527-537 (1995).
Jin et al., "Dramatic Rise in Plasma Viremia after CD8 T Cell Depletion in Simian Immunodeficiency Virus-infected Macaques", J. Exp. Med., 189: 991-8, 1999.
Jones et al., "Poly (DL-lactide-co-glycolide)-encapsulated plasmid DNA elicits systemic and mucosal antibody responses to encoded protein after oral administration," Vaccine, 15: 814-817, 1997.
Kawabata et al., "The Fate of Plasmid DNA After Intravenous Injection in Mice: Involvement of Scavenger Receptors in Its Hepatic Uptake," Pharm. Res., 12: 825-830, 1995.
Kent et al., "Enhanced T-Cell Immunogenicity and Protective Efficacy of a Human Immunodeficiency Virus Type 1 Vaccine Regimen Consisting of Consecutive Priming with DNA and Recombinant Fowlpox Virus," J. Virol., 72: 10180-10188, 1998.
Kern et al., "Target structures of the CD8(+)-T-cell response to human cytomegalovirus: the 72-kilodalton major immediate-early protein revisited," J. Virol., 73: 8179-8184, 1999.
Knapp et al., "A high frequency of Mamu-A*01 in the rhesus macaque detected by polymerase chain reaction with sequence-specific primers and direct sequencing," Tissue Antigens, 50: 657-661, 1997.
Kong et al., "Immunogenicity of Mutliple Gene and Clade Human Immunodeficiency . . . " J. of Virology 77(23):12764-12772, 2003.
Korber et al., "Epidemiological and Immunological Implications of the Global Variability of HIV" *Retroviral Immunology*, B. Walker, D. Pantaleo, Eds (The Humana Press, Totowa, NH, In press).
Kuroda et al., "Analysis of Gag-specific Cytotoxic T Lymphocytes in Simian Immunodeficiency Virus-infected Rhesus Monkeys by Cell Staining with a Tetrameric Major Histocompatibility Complex Class I-Peptide Complex," J. Exp. Med., 187: 1373-1381, 1998.
Lau et al., "Cytotoxic T-cell memory without antigen", Nature, 369: 648-52, 1994.
Letvin et al., "Cytotoxic T lymphocytes specific for the simian immunodeficiency virus", Immunol. Rev., 170: 127-34, 1999.
Letvin, N.L. "Progress in the development of an HIV-1 vaccine" Science 280:1875-1880, 1998.
Letvin et al., "Potent, protective anti-HIV immune responses generated by bimodal HIV envelope DNA plus protein vaccination," Proc. Natl. Acad. Sci. USA, 94: 9378-9383, 1997.
Levy et al., "Controlling HIV pathogenesis: the role of the noncytotoxic anti-HIV response of CD8 T cells", Immunol. Today, 17: 217-24, 1996.
Lew et al., "Cancer Gene Therapy Using Plasmid DNA: Pharmacokinetic Study of DNA Following Injection in Mice," Hum. Gene Ther., 6: 553, 1995.
Lewis, et al., "Limited Protection from a Pathogenic Chimeric Simian-Human Immunodeficiency Virus Challenge following Immunization with Attenuated Simian Immunodeficiency Virus", J. Virol., 73: 1262-70, 1999.
Li et al., "Infection of Cynomolgus Monkeys with a Chimeric HIV-2/SIV$_{mac}$ Virus That Expresses the HIV-1 Envelope Glycoproteins," J. of AIDS, 5: 639-646, 1992.
Lifson et al., "The Extent of Early Viral Replication Is a Critical Determinant of the Natural History of Simian Immunodeficiency Virus Infection", J. Virol., 71: 9508-14, 1997.
Livingston et al., "The Induction of Mucosal Immunity in the Female Genital Tract Using Gene-Gun Technology (Part 1: Antigen Expression)," Ann. New York Acad. Sci., 772: 265-267, 1995.
Lu et al., "SIV DNA vaccine trial in macaques: post-challenge necropsy in vaccine and control groups," Vaccine 15: 920-923, 1997.
Maecker et al., "DNA vaccination with cytokine fusion constructs biases the immune response to ovalbumin," Vaccine, 15: 1687-1696, 1997.
Maecker et al., "Cytotoxic T Cell Responses to DNA Vaccination: Dependence on Antigen Presentation via Class II MHC[1]," J. Immunol., 161: 6532-6536, 1998.
Mahnel et al., "[Experiences with immunization against orthopox viruses of humans and animals using vaccine strain MVA]," Berl. Munch Tierarztl Wochenschr, 107: 253-256, 1994. [English Translation of Abstract Attached].

(56) References Cited

OTHER PUBLICATIONS

Manthorpe et al., "Gene Therapy by Intramuscular Injection of Plasmid DNA: Studies on Firefly Luciferase Gene Expression in Mice," Hum. Gene Therapy, 4: 419-431, 1993.

Markmeyer et al., The pAX plasmids: new gene-fusion vectors for sequencing, mutagenesis and expression of proteins in *E.coli, Gene* 93:129-134 (1990).

Mayr et al., "[The smallpox vaccination strain MVA: marker, genetic structure, experience gained with the parenteral vaccination and behavior in organisms with a debilitated defence mechanism (author's transl)]," Zentralbl. Bakteriol., 167: 375-390, 1978. [English Translation of Abstract Attached].

McCluskie et al., "Direct Gene Transfer to the Respiratory Tract of Mice with Pure Plasmid and Lipid-Formulated DNA", Antisense Nucleic Acid Drug Dev., 8: 401-414, 1998.

Megede et al., "Increased Expression and Immunogenicity of Sequence-Modified . . . " J. of Virology 74(6):2628-2635, 2000.

Meyer et al., "Mapping of deletions in the genome of highly attenuated vaccinia virus MVA and their influence on virulence," *J. Gen. Virology* 72:1031-1038 (1991).

Mizuno et al., "Mutational analysis of two zinc-finger motifs in HIV type 1 nucleocapsid proteins: effects on proteolytic processing of Gag precursors and particle formation, "*Aides Research and Human Retroviruses* 12(9): 793-800 (1996).

Montgomery et al., "Heterologous and Homologous Protection Against Influenza A by DNA Vaccination: Optimization of DNA Vectors," DNA Cell Biol., 12: 777-783, 1993.

Moore et al., "HIV-1 neutralization: the consequences of viral adaptation to growth on transformed T cells," AIDS, 9(Suppl. A):S117-136, 1995.

Murali-Krishna et al., "Counting Antigen-Specific CD8 T Cells: A Reevaluation of Bystander Activation during Viral Infection," Immunity, 8:177-187, 1998.

Murali-Krishna et al., "Persistence of Memory CD8T Cells in MHC Class 1-Deficient Mice", Science, 286:1377-81, 1999.

Pal et al., "Inhibition of HIV-1 Infection by the β-Chemokine MDC", Science, 278: 695-8, 1997.

Persson et al., "Modifications of HIV-1 Retrovirus-Like Particles to Enhance . . . " Biologicals 26:255-265, 1998.

Pertmer and Robinson, "Studies on Antibody Responses Following Neonatal Immunization with Influenza Hemagglutinin DNA or Protein," Virology, 257:406-414, (1999).

Pertmer et al., "Influenza Virus Nucleoprotein-Specific Immunoglobin G Subclass and Cytokine Responses Elicited by DNA Vaccination are Dependent on the Route of Vector DNA Delivery," J. Virol., 70: 6119-6125, 1996.

Pertmer et al., "Gene gun-based nucleic acid immunization: elicitation of humoral and cytotoxic T lymphocyte responses following epidermal delivery of nanogram quantities of DNA," Vaccine, 13: 1427-1430, 1995.

Poignard et al., "Neutralizing Antibodies Have Limited Effects on the Control of Established HIV-1 Infection In Vivo," Immunity, 10: 431-438, 1999.

Porgador et al., "Predominant Role for Directly Transfected Dendritic Cells in Antigen Presentation to CD8+ T Cells after Gene Gun Immunization," J. Exp. Med., 188: 1075-1082, 1998.

Ramshaw and Ramsey, "The prime-boost strategy: exciting prospects for improved vaccination", Immunol. Today, 21: 163-5, 2000.

Reimann et al., "An *env* Gene Derived from a Primary Human Immunodeficiency Virus Type 1 Isolate Confers High In Vivo Replicative Capacity to a Chimeric Simian/Human Immunodeficiency Virus in Rhesus Monkeys," J. Virol., 70: 3198-3206, 1996.

Reimann et al., "A Chimeric Simian/Human Immunodeficiency Virus Expressing a Primary Patient Human Immunodeficiency Virus Type 1 Isolate *env* Causes an AIDS-Like Disease after In Vivo Passage in Rhesus Monkeys," J. Virol., 70: 6922-6928, 1996.

Richmond et al., "Studies of the Neutralizing Activity and Avidity of Anti-Human Immunodeficiency Virus Type 1 Env Antibody Elicited by DNA Priming and Protein Boosting," J. Virol., 72: 9092-9100, 1998.

Robinson and Pertmer, "DNA Vaccines: Basic Studies and Applications," in *Adv. Virus Res.*, 55: 1-74, 2000.

Robinson and Pertmer, "Nucleic Acid Immunizations," in *Current Protocols in Immunology*, (R. Coico, Ed.), vol. 1, pp. 2.14.1-2.14.19. 3 vols. John Wiley & Sons, Inc., New York.

Robinson et al., "Protection against a lethal influenza virus challenge by immunization with a haemagglutinin-expressing plasmid DNA," Vaccine, 11: 957-960, 1993.

Robinson et al., "The Scientific Future of DNA for Immunization," American Academy of Microbiology, May 13-Jun. 2, 1996, 1997.

Rodriguez et al., "DNA Immunization: Ubiquitination of a Viral Protein Enhances Cytotoxic T-Lymphocyte Induction and Antiviral Protection but Abrogates Antibody Induction," J. Virol., 71: 8497-8503, 1997.

Ross et al., "C3d enhancement of antibodies to hemagglutinin accelerates protection against influenza virus challenge," Nat. Immunology, 1:127-131, 2000.

Ross et al., "Enhanced Avidity Maturation of Antibody to Human Immunodeficiency Virus Envelope: DNA Vaccination with gp120-C3d Fusion Proteins," AIDS Res. Human Retro., 17(a):829-835, 2001.

Rubbert et al., "Multifactorial nature of non cytolytic CD8+ T cell-mediated suppression of HIV replication: beta-chemokine dependent and independent effects," AIDS Res. Hum. Retroviruses 13: 63-9, 1997.

Sasaki et al., "Comparison of Intranasal and Intramuscular Immunization against Human Immunodeficiency Virus Type 1 with a DNA-Monophosphoryl Lipid A Adjuvant Vaccine," Infect. Immunol., 66: 823-826, 1998.

Schmitz et al., "Control of Viremia in Simian Immunodeficiency Virus Infection by CD8 Lymphocytes", Science, 283: 857-60, 1999.

Schneider et al., "Induction of CD8 cells using heterologous prime-boost immunisation strategies", Immunol. Rev., 170: 29-38, 1999.

Schneider et al., "Enhanced immunogenicity for CD8+ T cell induction and complete protective efficacy of malaria DNA vaccination by boosting with modified vaccinia virus Ankara," Nat. Med., 4: 397-402, 1998.

Scholtissek et al., "A cloning cartridge of $\lambda t_o$ terminator," Nucleic Acids Res., 15: 3185, 1987.

Sizemore et al., "Attenuated *shigella* as a DNA Delivery Vehicle for DNA-Mediated Immunization," Science, 270: 299-302, 1995.

Sizemore et al., "Attenuated bacteria as a DNA delivery vehicle for DNA-mediated immunization," Vaccine, 15: 804-807, 1997.

Smith et al., "Multiprotein HIV Type 1 Clade B DNA/MVA Vaccine: . . . " Aids Research and Human Retroviruses 20(6):654-665, 2004.

Smith et al., "Recombinant Vaccinia Viruses as New Live Vaccines," *Biotechnology & Genetic Engineering Reviews* 2:383-407 (1984).

Staprans et al., "Simian Immunodeficiency Virus Disease Course Is Predicted by the Extent of Virus replication during Primary Infection", J. Virol., 73:4829-39, 1999.

Stittelaar et al., "Protective immunity in macaques vaccinated with a modified vaccinia virus Ankara-based measles virus vaccine in the presence of passively acquired antibodies," J. Virol., 74: 4236-4243, 2000.

Subbarao et al., "Genetic variability of HIV-1," AIDS, 10(Suppl. A):S13-23, 1996.

Sutcliffe, "Complete nucleotide sequence of the *Escherichia coli* plasmid pBR322," Cold Spring Harbor Quant. Biol., 43: 77-90, 1979.

Sutter et al., "Nonreplicating vaccinia vector efficiently expresses recombinant genes," Proc. Natl. Acad. Sci. USA, 89: 10847-10851, 1992.

Tang et al., "Genetic immunization is a simple method for eliciting an immune response," Nature, 356: 152-154, 1992.

Thomson et al., "Delivery of Multiple CD8 Cytotoxic T Cell Epitopes by DNA Vaccination," J. Immunol., 160: 1717-1723, 1998.

(56) References Cited

OTHER PUBLICATIONS

Tobery et al., "Targeting of HIV-1 Antigens for Rapid Intracellular Degradation Enhances Cytotoxic T Lymphocyte (CTL) Recognition and the Induction of De Novo CTL Responses In Vivo After Immunization," J. Exp. Med., 185: 909-920, 1997.
Tomaras et al., "CD8 T cell-mediated suppressive activity inhibits HIV-1 after virus entry with kinetics indicating effects on virus gene expression", Proc. Natl. Acad. Sci. U.S.A, 97:3503-8, 2000.
Torres et al., "DNA immunization: effect of secretion of DNA-expressed hemaggutinins on antibody responses," Vaccine, 18: 805-814, 2000.
Torres et al., "Differential Dependence on Target Site Tissue for Gene Gun and Intramuscular DNA Immunizations," J. Immunol., 158: 4529-4532, 1997.
Uchijima et al., "Optimization of Codon Usage of Plasmid DNA Vaccine Is Required for the Effective MHC Class I-Restricted T Cell Responses Against an Intracellular Bacterium," J. Immunol., 161: 5594-5599, 1998.
Ulmer et al., "Heterologous Protection Against Influenza by Injection of DNA Encoding a Viral Protein," Science 259: 1745-1749, 1993.
Villinger et al., "Induction of Long-Term Protective Effects against Heterologous Challenge in SIVhu-Infected Macaques", Virology, 278:194-206, 2000.
Wang et al., "Mammalian cell/vaccinia virus expression vectors with increased stability of retroviral sequences in *E.coli*; production of feline immunodeficiency virus envelope protein," Gene 153:197-202 (1995).
Watson et al., "Plasma Viremia in Macaques Infected with Simian Immunodeficiency Virus: Plasma Viral Load Early in Infection Predicts Survival", J. Virol., 71: 284-90, 1997.
Wild et al., "Polyvalent vaccination against hepatitis B surface and core antigen using a dicistronic expression plasmid," Vaccine, 16: 353-360, 1998.
Wolff et al. "Direct Gene Transfer into Mouse Muscle in Vivo," Science, 247: 1465-1468, 1990.
Wu et al., "Deoxyribonucleic Acid Vaccines Encoding Antigens With Rapid Proteasome-Dependent Degradation Are Highly Efficient Inducers of Cytolytic T Lymphocytes," J. Immunol., 159: 6037-6043, 1997.
Wyand et al., "Protection by live, attenuated simian immunodeficiency virus against heterologous challenge," J. Virol., 73: 8356-8363, 1999.
Wyatt et al., "Marker Rescue of the Host Range Restriction Defects of Modified Vaccinia Virus Ankara," Virology, 251:334-42, 1998.
Xiang et al., "Manipulation of the Immune Response to a Plasmid-Encoded Viral Antigen by Coinoculation with Plasmids Expressing Cytokines," Immunity, 2: 129-135, 1995.
Yamamoto et al., "Highly sensitive qualitative and quantitative detection of reverse transcriptase activity: optimization, validation, and comparative analysis with other detection systems," J. Virol. Methods, 61: 135-143, 1996.
Yang and Walker, "CD8+ cells in human immunodeficiency virus type I pathogenesis: cytolytic and noncytolytic inhibition of viral replication," Adv. Immunol., 66: 273-311, 1997.
Zajac et al., "Viral Immune Evasion Due to Presistence of Activated T Cells Without Effector Function", J. Exp. Med., 188:2205-13, 1998.
Allen et al., "Induction of AIDS virus-specific CTL activity in fresh . . . " J. Immunol. 164:4968-4978, 2000.
Amara et al., "Control of a Mucosal Challenge and Prevention of AIDS . . . "Science 292:69-74, 2001.
Ayyavoo et al., "Immunogenecity of a novel DNA vaccine cassette expressing multiple . . . " AIDS 14:1-9, 2000.
Barouch et al., "Control of Viremia and prevention of clinical AIDS in rhesus monkeys . . . "Science 290:486-492, 2000.
Bowie et al., "Deciphering the message in protein sequences: tolerance to amino acid substitutions" Science 257:1306-1310, 1990.
Burton et al., "Why do we not have an HIV vaccine and how can we make one" Nature Med. 4:495-498, 1998.

Caselli et al., "DNA immunization with HIV-1 mutated in the trans activation domain . . . "J. of Immunol. 162:5631-5638, 1999.
Davison et al., "New vaccinia virus recombination plasmids incorporating a synthetic . . . " Nucl. Acids. Res. 18(14):4285-4286, 1990.
Earl et al., "Comparison of vaccine strategies using recombinant env-gag-pol MVA . . . " Virology 294:270-281, 2002.
Earl et al., "Immunogenicity and protective efficacy of oligomeric human immunodeficiency virus . . . " J. of Virol. 75(2):645-653, 2001.
Egan et al., "Simian immunodeficiency virus (SIV) gag DNA-vaccinated rhesus monkey . . . " J. Virol. 74:7485-7495, 2000.
Englund et al. "Integration is required for productive infection of monocyte-derived macrophages . . . " J. of Virol. 69(5):3216-3219, 1995.
Feinberg et al., "AIDS vaccine models: Challenging challenge viruses" Nature Med. 8(3):207-210, 2002.
Gao et al., "Effects of mutations in the polymerase domain on the polymerase" J. Mol. Biol. 277:559-572, 1998.
Girard et al., "New prospects for the development of a vaccine against human immunodeficiency . . . " Sciences 322:959-966, 1999.
Gomez et al., "Recombinant proteins produced by vaccinia virus vectors . . . " Arch. Virol. 146(5):875-892, 2001.
Gorelick et al., "Nucleocapsid Protein Zinc-Finger Mutants of Simian Immunodeficiency . . . " Virology 259-70, 1999.
Goulder et al. "Anti-HIV cellular immunity: recent advances towards vaccine design" AIDS 13:S121-36, 1999.
Greenspan et al., "Defining epitopes: it's not easy as it seems" Nature Biotech. 7:936-937, 1999.
Hirsch et al., "Limited virus replication following SIV challenge of macaques . . . " Vaccines 95:195-200, 1995.
Hoffman-Lehman et al., "Sensitive and robust one-tube real-time reverse transcriptase-polymerase chain . . . " AIDS Res. Hum. Retroviruses 16:1247-1257, 2000.
Karacostas et al., "Human immunodeficiency virus-like particles produced by a vaccinia virus . . . " PNAS USA 86:8964-8967. 1989.
Karlsson et al., "Characterization of Molecularly Clones Simian-Human Immunodeficiency . . . "J. Virol. 71:4218-25, 1997.
Kuiken, C., "Reagents for HIV/SIV vaccine studies" HIV Sequences Compendium-2001, Los Almos, NM: Theoretical Biology and Biophysics Group.
Lechner et al., "Analysis of Successful Immune Responses in Persons Infected with Hepatitis C Virus" J. Exp. Med. 191:1499-1512, 2000.
Le Grice et al., "Active site mutagenesis of the AIDS virus protease and it alleviation . . . " The EMBO J. 7(8):2547-2553, 1988.
Letvin, N.L., "Progress in the development of an HIV-1 vaccine" Science 280:1875-1880, 1998.
Mellors et al., "Prognosis in HIV-1 Infection Predicted by the Quantity of Virus . . . "Science 272:1167-70, 1996.
Men et al., "Immunization of rhesus monkeys with a recombinant of modified vaccinia . . . " Vaccine 18:3113-3122, 2000.
Mizrahi et al., "Mutagenesis of the conserved aspartic acid 443, glutamic acid 478 . . . " J. of Biol. Chem 269(30):19245-19249, 1994.
Montefiori et al., "Neutralizing antibodies in sera from macaques infected with chimeric . . . "J. Virol. 72:3427-3431, 1998.
Montefiori et al., "Evaluation of antiviral drugs and neutralizing antibodies to human . . . "J. Clin. Microbiol. 26-231-237, 1988.
Moss et al., "Retroviruses of human AIDS and related animal diseases" Colloque des Cent Gardes 12th, Paris, France, Eds. M. Girard & B. Dodet, Editions Scientifiques et Medicales Elsevier, pp. 105-107, 1999 (abstract).
Ourmanov et al. "Comparative efficacy of recombinant modified vaccinia virus Ankra . . . "J. Virol. 74:2740-2751, 2000.
Ourmanov et al., "Recombinant modified vaccinia virus Ankara expressing . . . " J. Virol. 74:2960-2965, 2000.
Power et al., "A valid ELISPOT assay for enumeration of ex vivo, antigen-specific . . . " J. Immunol. Methods 227:99-107, 1999.
Quinn et al., "Viral load and heterosexual transmission of human immunodeficiency . . . " N. Eng. J. Med. 342:921-9, 2000.
Robinson et al., "AIDS vaccines: Heterologous Prime/Boost Strategies . . . " AIDS Reviews 2:105-110, 2000.
Robinson et al., "Neutralizing antibody-independent containment of immunodeficiency virus . . . " Nature Med. 5:526, 1999.

(56) References Cited

OTHER PUBLICATIONS

Sauter et al., "An internalization signal in the simian immunodeficiency virus . . . " J. Cell. Biol. 132:795-811, 1996.
Smith et al., "Multiprotein HIV type 1 clade B DNA/MVA vaccine" AIDS Res. & Human Retrov. 20(6):654-665, 2004.
Staprans et al., "Quantitative methods to monitor viral load in simian immunodeficiency virus infections" Viral Genome Methods, K. Adolph, Ed., CRC Press, Boca Raton, FL, pp. 167-184, 1996.
Wakefield et al., "In vitro enzymatic activity of human immunodeficiency virus . . . " J. of Virol. 66(11):6806-6812, 1992.
Waldrop et al., "Determination of antigen-specific memory/effector CD4 T cell . . . " J. Clin. Invest. 99:1739-50, 1997.
Zhang et al. "Nucleocapsid protein effects on the specificity of retrovirus RNA encapsidation" J. of Virol. 69(9):5716-5722, 1995.
Accession No. AF430344; (XP-002321209); Smith et al., Oct. 9, 2001.
Accession No. AF426288; (XP-002321210); Smith et al., Mar. 12, 2002.

| Chemokine coreceptor used | PBMC replication | Macrophage replication | T-cell-line replication | REplicative phenotype | Syncytium-inducing phenotype |
|---|---|---|---|---|---|
| X4 | + | – | + | Rapid/high | ++ |
| R5 | + | + | – | Slow/low | – |
| R5/X4 | + | + | + | Rapid/high | + |

FIG. 3

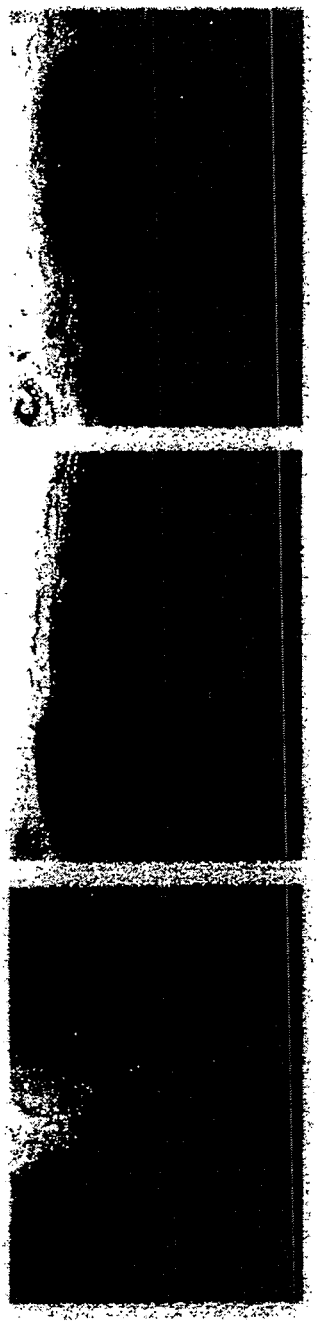

```
  1  GAATTCCTTG GTGGTCGCCA TGGATGCTGT TATTGTATAC TGTCTAAACG CGTTAGTAAA ACATGGCGAG
     CTTAAGCAAC CACCAGCGGT ACCTACCACA ATAACATATG ACAGATTTGC GCAATCATTT TGTACCGCTC

71  GAAATAAATC ATATAAAAAA TGATTTCATG ATTAAACCAT GTTGTGAAAA AGTCAAGAAC GTTCACATTG
     CTTTATTTAG TATATTTTTT ACTAAAGTAC TAATTTGGTA CAACACTTTT TCAGTTCTTG CAAGTGTAAC

141  GCGGACAATC TAAAAACAAT ACACTGATTG CACATTTGCC ATATATATGGAT AATGCGGTAT CCGATGTATG
     CGCCTGTTAG ATTTTTGTTA TGTGACTAAC GTGTAAACGG TATATACCTA TTACGCCATA GGCTACATAC

211  CAATTCACTG TATAAAAAGA ATGTATCAAG AATATCCAGA TTTGCTAATT TGATAAAGAT AGATGACGAT
     GTTAAGTGAC ATATTTTTCT TACATAGTTC TTATAGGTCT AAACGATTAA ACTATTTCTA TCTACTGCTA

281  GACAAGACTC CTACTGGTGT ATATAATTAT AAGATGCCAT TCCTCTGTTATT ATATCCATAG
     CTGTTCTGAG GATGACCACA TATATTAATA AAATTTGGAT TTCTACGGTA AGGACAATAA TATAGGTATC

351  GAAAGGATAG AGATGTTTGT GAACTATTAA TCTCATCTGA TAAAGCCGTGT GCGTGTATAG AGTTAAAATTC
     CTTTCCTATC TCTACAAACA CTTGATAATT AGAGTAGACT ATTTCGCACA CGCACATATC TCAATTTAAG
```

*FIG. 14A*

```
421 ATATAAAGTA GCCATTCTTC CCATGGATGT TTCCTTTTTT ACCAAAGGAA ATGCATCATT GATTATTCTC
    TATATTTCAT CGGTAAGAAG GGTACCTACA AAGGAAAAAA TGGTTTCCTT TACGTAGTAA CTAATAAGAG

491 CTGTTTGATT TCTCTATCGA TGCGGCACCT CTCTTAAGAA GTGTAACCGA TAATAAGTT ATTATATCTA
    GACAAACTAA AGAGATAGCT ACGCCGTGGA GAGAATTCTT CACATTGGCT ATTATTACAA TAATATAGAT

561 GACACCAGCG TCTACATGAC GAGCTTCCGA GTTCCAATTG GTTCAAGTTT TACATAAGTA TAAAGTCCGA
    CTGTGGTCGC AGATGTACTG CTCGAAGGCT CAAGGTTAAC CAAGTTCAAA ATGTATTCAT ATTTCAGGCT

631 CTATTGTTCT ATATTATATA TGGTTGTTGA TGGATCTGTG ATGCATGCAA TAGCTGATAA TAGAACTTAC
    GATAACAAGA TATAATATAT ACCAACAACT ACCTAGACAC TACGTACGTT ATCGACTATT ATCTTGAATG

701 GCAAATATTA GCAAAAATAT ATTAGACAAT ACTACAATTA ACGATGAGTG TAGATGCTGT TATTTTGAAC
    CGTTTATAAT CGTTTTTATA TAATCTGTTA TGATGTTAAT TGCTACTCAC ATCTACGACA ATAAAACTTG
```

FIG. 14B

```
 771  CACAGATTAG GATTCTTGAT AGAGATGAGA TGCTCAATGG ATCATCGTGT GATATGAACA GACATTGTAT
      GTGTCTAATC CTAAGAACTA TCTCTACTCT ACGAGTTACC TAGTAGCACA CTATACTTGT CTGTAACATA

841  TATGATGAAT TTACCTGATG TAGGCGAATT TGGATCTAGT ATGTTGGGGA AATATGAACC TGACATGATT
      ATACTACTTA AATGGACTAC ATCCGCTTAA ACCTAGATCA TACAACCCCT TTATACTTGG ACTGTACTAA

911  AAGATTGCTC TTTCGGTGCC TGGGTACCAG CGCGCCCTTT CATTTTGTTT TTTTCTATGC TATAAATGGT
      TTCTAACGAG AAAGCCACGG ACCCATGGTC GCGCGGGAAA GTAAAACAAA AAAAGATACG ATATTTACCA

981  ACGTCCTGTA GAAACCCCAA CCCGTGAAAT CAAAAAACTC GACGGCCTGT GGGCATTCAG TCTGGATCGC
      TGCAGGACAT CTTTGGGGTT GGGCACTTTA GTTTTTTGAG CTGCCGGACA CCCGTAAGTC AGACCTAGCG

1051  GAAAACTGTG GAATTGATCA GCGTTGGTGG GAAAGCGCGT TACAAGAAAG CCGGGCAATT GCTGTGCCAG
      CTTTTGACAC CTTAACTAGT CGCAACCACC CTTTCGCGCA ATGTTCTTTC GGCCCGTTAA CGACACGGTC
```

FIG. 14C

```
1121  GCAGTTTTAA CGATCAGTTC GCCGATGCAG ATATTCGTAA TTATGCGGGC AACGTCTGGT ATCAGCGCGA
      CGTCAAAATT GCTAGTCAAG CGGCTACCGTC TATAAGCATT AATACGCCCG TTGCAGACCA TAGTCGCGCT

1191  AGTCTTTATA CCGAAAGGTT GGGCAGGCCA GCGTATCGTG CTGCCTTTCG ATGCGGGTCAC TCATTACGGC
      TCAGAAATAT GGCTTTCCAA CCCGTCCGGT CGCATAGCAC GACGGAAAGC TACGCCCAGTG AGTAATGCCG

1261  AAAGTCTGGG TCAATAATCA GGAAGTGATG GAGCATCAGG GCGGGCTATAC GCCATTTGAA GCCGATGTCA
      TTTCACACCC AGTTATTAGT CCTTCACTAC CTCGTAGTCC CGCCCGATATG CGGTAAACTT CGGCTACAGT

1331  CGCCGTATGT TATTGCCGGG AAAAGTGTAC GTATCACCGT TTGTGTGAAC AACGAACTGA ACTGGCAGAC
      GCGGCATACA ATAACGGCCC TTTTCACATG CATAGTGGCA ACACACTTG TTGCTTGACT TGACCGTCTG

1401  TATCCCGCCG GGAATGGTGA TTACCGACGA AAACGGCAAG AAAAAGCAGT CTTACTTCCA TGATTTCTTT
      ATAGGGCGGC CCTTACCACT AATGGCTGCT TTTGCCGTTC TTTTTCGTCA GAATGAAGGT ACTAAAGAAA

1471  AACTATGCCG GAATCCATCG CAGCGTAATG CAGCGTAATG CTCTACACCA CGCCGAACAC CTGGGTGGAC GATATCACCG
      TTGATACGGC CTTAGGTAGC GTCGCATTAC GAGATGTGGT GCGGCTTGTG GACCCACCTG CTATAGTGGC
```

FIG. 14D

1541  TGGTGACGGCA TGTCGCGCAA GACTGTAACC ACGCGTCTGT TGACTGGCAA GTGGTGGCCA ATGGTGATGT
      ACCACTGCCT ACAGCGCGTT CTGACATTGG TGGCAGACA ACTGACCGTC CACCACCGGT TACCACTACA

1611  CAGCGGTTGAA CTGCGTGATG CGGATCAACA GGTGCTTGCA ACTGGACAAG GCACTAGCGG GACTTTGCAA
      GTCGCAACTT GACGCACTAC GCCTAGTTGT CCACCAACGT TGACCTGTTC CGTGATCGCC CTGAAACGTT

1681  GTGGTCAATC CGCACCTCTG GCAACCGGGT GAAGGTTATC TCTATGAACT GTGGGTCACA GCCAAAGCC
      CACCACTTAG GCGTGGAGAC CGTTGGCCCA CTTCCAATAG AGATACTTGA CACCCAGTGT CGGTTTTCGG

1751  AGACAGAGTG TGATATCTAC CCGCTTCGCG GGGAAGCGC AGCCGTAGGC CAGTCACCGT CACTTCCCGC TTGTCAAGGA
      TCTGTCTCAC ACTATAGATG GGCGAAGCGC TCGGCATCAT CGTTCAGTGGCA GTCAGTGGCA CACTTCCCGC TTGTCAAGGA

1821  GATTAACCAC AAACCGTTCT ACTTTACTGG CTTTGGTCGT CATGAAGATG CGGACTTGCC TGGCAAAGGA
      CTAATTGGTG TTTGGCAAGA TGAAATGACC GAAACCAGCA GTACTTCTAC GCCTGAACGC ACCGTTTCCT

1891  TTCGATAACG TGCTGATGGT GCACGACCAC GCATTAATGG ACTGGGATTGG TACCGTACCT TACCGTACCT ATGGCATGGA
      AAGCTATTGC ACGACTACCA CGTGCTGGTC CGTAATTAACC TGACCTAACC CCGGTTGAGG ATGGCATGGA

FIG. 14E

```
1961  CGCATTACCC TTACGCTGAA GAGATGCTCG ACTGGGCAGA TGAACATGGC ATCGTGGTCA TTGATGAAAC
      GCGTAATGGG AATGCGACTT CTCTACGAGC TGACCCGTCT ACTTGTACCG TAGCACCACT AACTACTTTG

2031  TGCTGCTGTC GGCTTTAACC TCTCTTTAGG CATTGGTTTC GAAGCGGGCA ACAAGCCGAA AGAACTGTAC
      ACGACGACAG CCGAAATTGG AGAGAAATCC GTAACCAAAG CTTCGCCCGT TGTTCGGCTT TCTTGACATG

2101  ACCGAAGAGG CAGTCAACGG GGAAACTCAG CAAGCGCACT TACAGGCGAT TAAAGAGCTG ATAGCGCGTG
      TGGCTTCTCC GTCAGTTGCC CCTTTGAGTC GTTCGCGTGA ATGTCCGCTA ATTTCTCGAC TATCGCGCAC

2171  ACAAAAACCA CCCAAGCGTG GTGATGTGGA GTATTGCCAA CGAACCGGAT ACCCGTCCGC AAGGTGCACG
      TGTTTTTGGT GGGTTCGCAC CACTACACCT CATAACGGTT GCTTGGCCTA TGGGCAGGCG TTCCACGTGC

2241  GGAATATTTC GCGCCACTGG CGGAAGCAAC GCGTAAACTC GACCCGACGC GTCCGATCAC CTGCGTCAAT
      CCTTATAAAG CGCGGTGACC GCCTTCCGTTG CGCATTTGAG CTGGGCTGCG CAGGCTAGTG GACGCAGTTA

2311  GTAATGTTCT GCGACGCTCA CACCCGATACC TCTTTGATGT GCTGCTGCCTG AACCGTTATT
      CATTACAAGA CGCTGCGAGT GTGGCTATGG AGAAACTACA CGACACGGAC TTGGCAATAA
```

FIG. 14F

```
2381  ACGGATGGTA TGTCCAAAGC GGCGATTTGG AAACGGCAGA GAAGGTACTG GAAAAAGAAC TTCTGGCCTG
      TGCCTACCAT ACAGGTTTCG CCGCTAAACC TTTGCCGTCT CTTCCATGAC CTTTTTCTTG AAGACCGGAC

2451  GCAGGAGAAA CTGCATCAGC CGATTATCAT CACCGAATAC GGCGTGGATA CGTTAGCCGG GCTGCACTCA
      CGTCCTCTTT GACGTAGTCG GCTAATAGTA GTGGCTTATG CCGCACCTAT GCAATCGGCC CGACGTGAGT

2521  ATGTACACCG ACATGTCGAC TGAAGAGTAT CAGTCTGCAT GGCTGGATAT GTATCACCGC GTCTTTGATC
      TACATGTGGC TGTACAGCTG ACTTCTCATA GTCAGACGTA CCGACCTATA CATAGTGGCG CAGAAACTAG

2591  GCGTCAGCGC CGTCGTCGGT GAACAGGTAT GGAATTTCGC CGATTTTGCC ACCTCGCAAG GCATATTGCG
      CGCAGTCGCG GCAGCAGCCA CTTGTCCATA CCTTAAAGCG GCTAAAACGG TGGAGCGTTC CGTATAACGC

2661  CGTTGGGCGT AACAAGAAAG GGATCTTCAC TCGCGACCGC AAACCGAAGT CGGGGGCTTT TCTGCTGCAA
      GCAACCGCCA TTGTTCTTTC CCTAGAAGTG AGCGCTGGCG TTTGGCTTCA GCCCCGAAA AGACGACGTT

2731  AAACGGCTGGA CTGGCATGAA CTTCCGGTGAA AAACCCCAGC AGGGAGGCAA ACAATGAGAG CTCGGTTGTT
      TTTGCCGACCT GACCGTACTT GAAGGCCACTT TTTGGGGTCG TCCCTCCGTT TGTTACTCTC GAGCCAACAA
```

*FIG. 14G*

2801  GATGGATCTG TGATGCATGC AATAGCTCAT AATAGAACTT ACGCAAATAT TAGCAAAAAT ATATTAGACA
      CTACCTAGAC ACTACGTACG TTATCGACTA TTATCTTGAA TGCGTTTATA ATCGTTTTTA TATAATCTGT

2871  ATACTACAAT TAACGATGAG TGTAGAGATCCT GTTATTTTGA ACCACAGATT AGGATTCTTG ATAGAGATGA
      TATGATGTTA ATTGCTACTC ACATCTACGA CAATAAAACT TGGTGTCTAA TCCTAAGAAC TATCTCTACT

2941  GATGCTCAAT GGATCATCGT GTGATATGAA CAGACATTGT ATTATGATGA ATTTACCTGA TGTAGGCGAA
      CTACGAGTTA CCTAGTAGCA CACTATACTT GTCTGTAACA TAATACTACT TAAATGGACT ACATCCGCTT

3011  TTTGGATCTA GTATGTTGGG GAAATATGAA CCTGACATGA TTAAGATTGC TCTTTCGGTG GCTGGGGGCC
      AAACCTAGAT CATACAACCC CTTTATACTT GGACTGTACT AATTCTAACG AGAAAGCCAC CGACGCCGG

3081  CGCTCGAGTA AAAAATGAAA AAATATTCTA ATTTATAGGA CGGTTTTGAT TTTCTTTTTT TCTATGCTAT
      GCGAGCTCAT TTTTTACTTT TTTATAAGAT TAAATATCCT GCCAAAACTA AAAGAAAAAA AGATACGATA

3151  AAATAATAAA TAGCGGGCCGC ACCATGAAAG TGAAGGGGAT CAGGAAGAAT TATCAGCCACT TGTGGAAATG
      TTTATTATTT ATCGCCCGGCG TGGTACTTTC ACTTCCCCTA GTCCTTCTTA ATAGTCGTGA ACACCTTTAC

FIG. 14H

```
3221  GGGCATCATG CTCCTTGGGA TGTTGATGAT CTGTAGTGCT GTAGAAAATT TGTGGGTCAC AGTTTATTAT
      CCCGTAGTAC GAGGAACCCT ACAACTACTA GACATCACGA CATCTTTTAA ACACCCAGTG TCAAATAATA

3291  GGGGTACCTG TCTGGAAAGA AGCAACCACC ACTCTATTTT GTGCATCAGA TGCTAAAGCA TATGATACAG
      CCCCATGGAC AGACCTTTCT TCGTTGGTGG TGAGATAAAA CACGTAGTCT ACGATTTCGT ATACTATGTC

3361  AGGTACATAA TGTTTCGGCC ACACATGCCT GTGTACCCAC AGACCCCAAC CCACAAGAAG TAGTATTGGA
      TCCATGTATT ACAAAGCCGG TGTGTACGGA CACATGGGTG TCTGGGGTTG GGTGTTCTTC ATCATAACCT

3431  AAATGTGACA GAAAATTTTA ACATGTGGAA AAATAACATG GTAGAACAGA TGCATGAGGA TATAATCAGT
      TTTACACTGT CTTTTAAAAT TGTACACCTT TTTATTGTAC CATCTTGTCT ACGTACTCCT ATATTAGTCA

3501  TTATGGGATC AAAGCCTAAA GCCATGTGTA AAATTAACCC CACTCTGTGT TACTTTAAAT TGCACTGATT
      AATACCCTAG TTTCGGATTT CGGTACACAT TTTAATTGGG GTGAGACACA ATGAAATTTA ACGTGACTAA

3571  TGAGGAATGT TACTAATAGTA AATAATAGTA GTGAGGGAAT GAGAGGAGAA ATAAAAAACT GCTCTTTCAA
      ACTCCTTACA ATGATTATAG TTATTATCAT CACTCCCTTA CTCTCCTCTT TATTTTTTGA CGAGAAAGTT
```

FIG. 14I

3641 TATCACCACA AGCATAAGAG ATAAGGTGAA GAAAGACTAT GCACTTTTCT ATAGACTTGA TGTAGTACCA
     ATAGTGGTGT TCGTATTCTC TATTCCACTT CTTTCTGATA CGTGAAAAGA TATCTGAACT ACATCATGGT

3711 ATAGATAATG ATAATACTAG CTATAGGTTG ATAAATTGTA ATACCTCAAC CATTACACAG GCCTGTCCAA
     TATCTATTAC TATTATGATC GATATCCAAC TATTTAACAT TATGGAGTTG GTAATGTGTC CGGACAGGTT

3781 AGGTATCCTT TGAGCCAATT CCCATACATT ATTGTACCCC GGCTGGTTTT CCGATTCTAA AGTGTAAAGA
     TCCATAGGAA ACTCGGTTAA GGGTATGTAA TAACATGGGG CCGACCAAAA CGGCTAAGATT TCACATTTCT

3851 CAAGAAGTTC AATGGAACAG GGCCATGTAA AAATGTCAGC ACAGTACAAT GTACACATGG AATTAGGCCA
     GTTCTTCAAG TTACCTTGTC CCGGTACATT TTTACAGTCG TGTCATGTTA CATGTGTACC TTAATCCGGT

3921 GTAGTGTCAA CTCAACTGCT GTTAAATGGC AGTCTAGCAG AAGAAGAGGT AGTAATTAGA TCTAGTAATT
     CATCACAGTT GAGTTGACGA CAATTTACCG TCAGATCGTC TTCTTCTCCA TCATTAATCT AGATCATTAA

3991 TCACAGACAA TGCAAAAAAC ATAATAGTAC AGTTGAAAGA ATCTGTAGAA ATTAATTGTA CAAGACCCAA
     AGTGTCTGTT ACGTTTTTTG TATTATCATG TCAACTTTCT TAGACATCTT TAATTAACAT GTTCTGGGTT

FIG. 14J

```
4061  CAACAATACA AGGAAAAGTA TACATATAGC ACCAGGAAGA GCATTTTATA CAACAGGAGA AATAATAGGA
      GTTGTTATGT TCCTTTTCAT ATGTATATCC TGGTCCTTCT CGTAAAATAT GTTGTCCTCT TTATTATCCT

4131  GATATAAGAC AAGCACATTG CAACATTAGT AGAACAAAAT GGAATAACAC TTTAAATCAA ATAGCTACAA
      CTATATTCTG TTCGTGTAAC GTTGTAATCA TCTTGTTTTA CCTTATTGTG AAATTTAGTT TATCGATGTT

4201  AATTAAAAGA ACAATTTGGG AATAATAAAA CAATAGTCTT TAATCAATCC TCAGGAGGGG ACCCAGAAAT
      TTAATTTTCT TGTTAAACCC TTATTATTTT GTTATCAGAA ATTAGTTAGG AGTCCTCCCC TGGGTCTTTA

4271  TGTAATGCAC AGTTTTAATT GTGGAGGGGA ATTCTCTAC TGTAATTCAA CACAACTGTT TAATAGTACT
      ACATTACGTG TCAAAATTAA CACCTCCCCT TAAGAAGATG ACATTAAGTT GTGTTGACAA ATTATCATGA

4341  TGGAATTTTA ATGGTACTTG GAATTTAACA CAATCGAATG GTACTGAAGG CTACTGAAGG AATGACACTT ATCACACTCC
      ACCTTAAAAT TACCATGAAC CTTAAATTGT GTTAGCTTAC CATGACTTCC TTTACTGTGA TAGTGTGAGG

4411  CATGTAGAAT AAAACAAATT ATAAATATGT GGCAGGAAGT AGGAAAAGCA ATGTATGCCC CTCCCATCAG
      GTACATCTTA TTTTGTTTAA TATTTATACA CCGTCCTTCA TCCTTTTCGT TACATACGGG GAGGGTAGTC
```

FIG. 14K

```
4481  AGGACAAATT AGATGCTCAT CAAATATTAC AGGGCTAATA TTAACAAGAG ATGGTGGAAC TAACAGTAGT
      TCCTGTTTAA TCTACGACTA GTTTATAATG TCCCGATTAT AATTGTTCTC TACCACCTTG ATTGTCATCA

4551  GGGTCCGAGA TCTTCAGACC TGGGGGAGGA GATATGAGGG ACAATTGGAG AAGTGAATTA TATAAATATA
      CCCAGGCTCT AGAAGTCTGG ACCCCCTCCT CTATACTCCC TGTTAACCTC TTCACTTAAT ATATTTATAT

4621  AAGTAGTAAA AATTGAACCA TTAGGAGTAG CACCCACCAA GGCAAAAAGA AGAGTGGTGC AGAGAGAAAA
      TTCATCATTT TTAACTTGGT AATCCTCATC GTGGGTGGTT CCGTTTTTCT TCTCACCACG TCTCTCTTTT

4691  AAGAGCAGTG GGAACGATAG GAGCTATGTT CCTTGGGGTC TTGGCAGCAG CAGGAAGCAC TATGGGCGCA
      TTCTCGTCAC CCTTGCTATC CTCGATACAA GGAACCCCAAG AACCGTCGTC GTCCTTCGTG ATACCCGCGT

4761  GGGTCAATAA CGCTGACGGT ACAGGCCAGA CTATTATTGT GATAATAACA GCAACAGCAG AACAATTGC
      CGCAGTTATT GCGACTGCCA TGTCCGGTCT GATAATAACA GACCATATCA CGTTGTCGTC TTGTTAAACG

4831  TGAGGGCTAT TGAGGGCGCAA CAGCATCTGT TGCAACTCAC AGTCTGGGGC ATCAAGCAGC TCCAGGCAAG
      ACTCCCGATA ACTCCCGCGTT GTCGTAGACA ACGTTGAGTG TCAGACCCCG TAGTTCGTCG AGGTCCGTTC
```

FIG. 14L

```
4901  AGTCCTGGCT GTGGAAAGAT ACCTAAGGGA TCAACAGCTC CTAGGGATTT GGGGTTGCTC TGGAAAACTC
      TCAGGACCCA CACCTTTCTA TGGATTCCCT AGTTGTCGAG GATCCCTAAA CCCCAACGAC ACCTTTTGAG

4971  ATCTGCACCA CTGCTGTGCC TTGGAATGCT AGTTGGAGTA ATAAAACTCT GGATATGATT TGGATAACA
      TAGACGTGGT GACGACACGG AACCTTACGA TCAACCTCAT TATTTTGAGA CCTATACTAA ACCCTATTGT

5041  TGACCTGGAT GGAGTGGGAA AGAGAAATCG AAAATTACAC AGGCTTAATA TACACCTTAA TTGAGGAATC
      ACTGGACCTA CCCTCACCCTT TCTCTTTAGC TTTTAATGTG TCCGAATTAT ATGTGGAATT AACTCCTTAG

5111  GCAGAACCAA CAAGAAAAGA ATGAACAAGA CTTATTAGCA TTAGATAAGT GGGCAAGTTT CTGGAATTCC
      CGTCTTGGTT GTTCTTTTCT TACTTGTTCT GAATAATCGT AATCTATTCA CCCGTTCAAA CACCTTAACC

5181  TTTGACATAT CAAATTGGCT GTGGTATGTA AAAATCTTCA TAATGATAGT AGGAGGCTTG ATAGTTTAA
      AAACTGTATA GTTTAACCGA CACCATACAT TTTTAGAAGT ATTACTATCA TCCTCCGAAC TATCCAAATT

5251  GAATAGTTTT TACTGTACTT TCTATAGTAA ATAGAGTTAG GCAGGGATAC TCACCATTGT CATTTCAGAC
      CTTATCAAAA ATGACATGAA AGATATCATT TATCTCAATC CGTCCCTATG AGTGGTAACA GTAAAGTCTG
```

*FIG. 14M*

```
5321  CCACCTCCCA GCCCCGAGGC GACCCGACAG GCCCGAAGGA ATCGAAGAAG AAGGTGGAGA CAGAGACTAA
      GGTGGAGGGT CGGGGCTCCC CTGGGCTGTC CGGGCTTCCT TAGCTTCTTC TTCCACCTCT GTCTCTGATT

5391  TTTTTATGCG GCCGCTGGTA CCCAACCTAA AAATTGAAAA TAAATACAAA GGTTCTTGAG GGTTGTGTTA
      AAAAATACGC CGGCGACCAT GGGTTGGATT TTTAACTTTT ATTTATGTTT CCAAGAACTC CCAACACAAT

5461  AATTGAAAGC GAGAAATAAT CATAAATAAG CCCGGGGATC CTCTAGAGTC GACACCATGG GTGCGAGAGC
      TTAACTTTCG CTCTTTATTA GTATTTATTC GGGCCCCTAG GAGATCTCAG CTGTGGTACC CACGCTCTCG

5531  GTCAGTATTA AGCGGGGGAG AATTAGATCG ATGGGAAAAA ATTCGGTTAA GGCCAGGGGG AAAGAAAAAA
      CAGTCATAAT TCGCCCCCTC TTAATCTAGC TACCCTTTTT TAAGCCAATT CCGGTCCCCC TTTCTTTTTT

5601  TATAAATTAA AACATATAGT ATGGGCAAGC AGGGAGCTAG AACGATTCGC AGTTAATCCT GGCCTGTTAG
      ATATTTAATT TTGTATATCA TACCCGTTCG TCCCTCGATC TTGCTAAGCG TCAATTAGGA CCGGACAATC

5671  AAACATCAGA AGGCTGTAGA CAAATACTGG GACAGCTACA ACCATCCCTT CAGACAGGAT CAGAAGAACT
      TTTGTAGTCT TCCGACATCT GTTTATGACC CTGTCGATGT TGGTAGGGAA GTCTGTCCTA GTCTTCTTGA
```

*FIG. 14N*

```
5741  TAGATCATTA TATAATACAG TAGCAACCCT CTATTGTGTG CATCAAAGGA TAGAGATAAA AGACACCAAG
      ATCTAGTAAT ATATTATGTC ATCGTTGGGA GATAACACAC GTAGTTTCCT ATCTCTATTT TCTGTGGTTC

5811  GAAGCTTTAG ACAAGATAGA GGAAGAGCAA AACAAAAAGC AGAAAAAAGC ACACCAAGCA GCAGCTGACA
      CTTCGAAATC TGTTCTATCT CCTTCTCGTT TTGTTTTTCG TCTTTTTTCG TGTGGTTCGT CGTCGACTGT

5881  CAGGACACAG CAATCAGGTC AGCCAAAATT ACCCTATAGT GCAGAACATC CAGGGGCAAA TGGTACATCA
      GTCCTGTGTC GTTAGTCCAG TCGGTTTTAA TGGGATATCA CGTCTTGTAG GTCCCCGTTT ACCATGTAGT

5951  GGCCATATCA CCTAGAACTT TAAATGCATG GGTAAAAGTA GTAGAAGAGA AGGCTTTCAG CCCAGAAGTG
      CCGGTATAGT GGATCTTGAA ATTTACGTAC CCATTTTCAT CATCTTCTCT TCCGAAAGTC GGGTCTTCAC

6021  ATACCCATGT TTTCAGCATT ATCAGAAGGA GCCACCCCAC AAGATTTAAA CACCATGCTA AACACAGTGG
      TATGGGTACA AAAGTCGTAA TAGTCTTCCT CGGTGGGGTG TTCTAAATTT GTGGTACGAT TTGTGTCACC

6091  GGGGACATCA AGCAGCCATG CAAATGTTAA AAGAGACCAT CAATGAGGAA GCTGCACAGAAT GGGATAGACT
      CCCCTGTAGT TCGTCGGTAC GTTTACAATT TTCTCTGGTA GTTACTCCTT CGACGTCTTA CCCTATCTCA
```

FIG. 140

```
6161  GCATCCAGTG CATGCAGGGC CTATTGCACC AGGCCAGATG AGAGAACCAA GGGGAAGTGA CATAGCAGGA
      CGTAGGTCAC GTACGTCCCG GATAACGTGG TCCGGTCTAC TCTCTTGGTT CCCCTTCACT GTATCGTCCT

6231  ACTACTAGTA CCCTTCAGGA ACAAATAGGA TGGATGACAA ATAATCCACC TATCCCAGTA GGAGAAATTT
      TGATGATCAT GGGAAGTCCT TGTTTATCCT ACCTACTGTT TATTAGGTGG ATAGGGTCAT CCTCTTTAAA

6301  ATAAAAGATG GATAATCCTG GGATTAAAATA AAATAGTAAG AATGTATAGC CCTACCAGCA TTCTGGACAT
      TATTTTCTAC CTATTAGGAC CCTAATTTAT TTTATCATTC TTACATATCG GGATGGTCGT AAGACCTGTA

6371  AAGACAAGGA CCAAAAGAAC CTTTAGAGA CTATGTAGAC CGGTTCTATA AAACTCTAAG AGCCGAGCAA
      TTCTGTTCCT GGTTTTCTTG GAAATCTCT GATACATCTG GCCAAGATAT TTTGAGATTC TCGGCTCGTT

6441  GCTTCACAGG AGGTAAAAAA TTGGATGACA GAAACCTTGT TGGTCCAAAA TGCGAACCCA GATTGTAAGA
      CGAAGTGTCC TCCATTTTTT AACCTACTGT CTTTGGAACA ACCAGGTTTT ACGCTTGGGT CTAACATTCT

6511  CTATTTTAAA AGCATTGGGA CCAGCGGCTA CACTAGAAGA AATGATGACA GCATGTCAGG GAGTAGGAGG
      GATAAAATTT TCGTAACCCT GGTCGCCGAT GTGATCTTCT TTACTACTGT CGTACAGTCC CTCATCCTCC
```

FIG. 14P

```
6581  ACCCGGCCAT AAGGCAAGAG TTTTGGCTGA AGCAATGAGC CAAGTAACAA ATTCAGCTAC CATAATGATG
      TGGGCCGGTA TTCCGTTCTC AAAACCGACT TCGTTACTCG GTTCATTGTT TAAGTCGATG GTATTACTAC

6651  CAGAGAGGCA ATTTTAGGAA CCAAAGAAAG ATTTCTTAAG CTTCAATTG TGGCAAAGAA GGGCACACAG
      GTCTCTCCGT TAAAATCCTT GGTTTCTTTC TAAAGAATTC GAAGTTAAC ACCGTTTCTT CCCGTGTGTC

6721  CCAGAAATTG CAGGGCCCCT AGGAAAAAGG GCTGTTGGAA ATGTGGAAAG CAAGGACACC AAATGAAAGA
      GGTCTTTAAC GTCCCGGGGA TCCTTTTTCC CGACAACCTT TACACCTTTC GTTCCTGTGG TTTACTTCT

6791  TTGTACTGAG AGACAGGCTA ATTTTTTAGG GAAGATCTGG CCTTCCTACA AGGGAAGGCC AGGGAATTTT
      AACATGACTC TCTGTCCGAT TAAAAAATCC CTTCTAGACC GGAAGGATGT TCCCTTCCGG TCCCTTAAAA

6861  CTTCAGAGCA GACCAGAGCC AACACAGCCCA CCAGAAGAGA GCTTCAGGTC TGGGGTAGAG ACAACAACTC
      GAAGTCTCGT CTGGTCTCGG TTGTCGGGGT GGTCTTCTCT CGAAGTCCAG ACCCCATCTC TGTTGTTGAG

6931  CCCCTCAGAA GCAGGAGCCG ATAGACAAGG AACTCTATCC TTTAACTTCC CTCAGATCAC TCTTTGGCAA
      GGGGAGTCTT CGTCCTCGGC TATCTGTTCC TTGAGATAGG AAATTGAAGG GAGTCTAGTG AGAAACCGTT
```

FIG. 14Q

```
7001  CGACCCCTCG TCACAATAAA GATAGGGGGG CAACTAAAGC AAGCTCTATT AGATACAGGA CCAGATGATA
      GCTGGGGAGC AGTGTTATTT CTATCCCCCC GTTGATTTCG TTCGAGATAA TCTATGTCCT CGTCTACTAT

7071  CAGTATTAGA AGAAATGAGT TTGCCAGGAA GATGGAAACC AAAAATGATA GGGGGAATTG GAGGTTTTAT
      GTCATAATCT TCTTTACTCA AACGGTCCTT CTACCTTTGG TTTTTACTAT CCCCCTTAAC CTCCAAAATA

7141  CAAAGTAAGA CAGTATGATC AGATATACTCAT AGAAATCTGT GGACATAAAG CTATAGGTAC AGTATTAGTA
      GTTTCATTCT GTCATACTAG TCTATATGAGTA TCTTTAGACA CCTGTATTTC GATATCCATG TCATAATCAT

7211  GGACCTACAC CTGTCAACAT AATTGGAAGA AATCTGTTGA CTCAGATTGG TTGCACTTTA AATTTTCCCA
      CCTGGATGTG GACAGTTGTA TTAACCTTCT TTAGACAACT GAGTCTAACC AACGTGAAAT TTAAAAGGGT

7281  TTAGCCCTAT TGAGACTGTA CCAGTAAAAT TAAAGCCCAGG AATGGATGGC CCAAAAGTTA AACAATGGCC
      AATCGGGATA ACTCTGACAT GGTCATTTTA ATTCGGTCC TTACCTACCG GGTTTTCAAT TTGTTACCGG

7351  ATTCACAGAA GAAAAAATAA AAGCATTAGT AGAAATTTGT ACAGAAATGG AAAAGGAAGG GAAAATTTCA
      TAACTGTCTT CTTTTTTATT TTCGTAATCA TCTTTAAACA TGTCTTTACC TTTTCCTTCC CTTTTAAAGT
```

FIG. 14R

```
7421  AAAATTGGGC CTGAGAATCC ATACAATACT CCAGTATTTG CCATAAAGAA AAAAGACAGT ACTAAATGGA
      TTTTAACCCG GACTCTTAGG TATGTTATGA GGTCATAAAC TTTTCTGTCA TGATTTACCT

7491  GAAATTAGT AGATTTCAGA GAACTTAATA AGAGAACTCA AGACTTCTGG GAAGTTCAAT TAGGAATACC
      CTTTAATCA TCTAAAGTCT CTTGAATTAT TCTCTTGAGT TCTGAAGACC CTTCAAGTTA ATCCTTATGG

7561  ACATCCCGCA CGGTTAAAAA AGAAAAAATC AGTAACAGTA CTGGATGTGG GTGATGCATA TTTTTCAGTT
      TGTAGGGCGT CCCAATTTTT TCTTTTTTAG TCATTGTCAT GACCTACACC CACTACGTAT AAAAAGTCAA

7631  CCCTTAGATC AAGACTTCAG GAAGTATACT GCATTTACCA TACCTAGTAT AAACAATGAC ACACCAGGGA
      GGGAATCTAG TTCTGAAGTC CTTCATATGA CGTAAATGGT ATGGATCATA TTTGTTACTC TGTGGTCCCT

7701  TTAGATATCA GTACAATGTG CTTCCACAGG GATGGAAAGG ATCACCAGCA ATATTCCAAA GTAGGATGAC
      AATCTATAGT CATGTTACAC GAAGGTGTCC CTACCTTTCC TAGTGGTCGT TATAAGGTTT CATCGTACTG

7771  AAAAATCTTA GAGCCTTTTA AAAAACAAAA TCCAGACATA GTTATCTATC AATACATGAA CGATTTGTAT
      TTTTTAGAAT CTCGGAAAAT TTTTTGTTTT AGGTCTGTAT CAATAGATAG TTATGTACTT GCTAAACATA
```

FIG. 14S

```
7841  GTAGGATCTG ACTTAGAAAT AGGGCAGCAT AGAACAAAAA TAGAGGAGCT GAGACAACAT CTGTTGAGGT
      CATCCTAGAC TGAATCTTTA TCCCGTCGTA TCTTGTTTTT ATCTCCTCGA CTCTGTTGTA GACAACTCCA

7911  GGGGACTTAC CACACCAGAC AAAAAACATC AGAAAGAACC TCCATTCCTT TGCATGGGTT ATGAACTCCA
      CCCCTGAATG GTGTGGTCTG TTTTTTGTAG TCTTTCTTGG AGGTAAGGAA ACCTACCCAA TACTTGAGGT

7981  TCCTGATAAA TGGACAGTAC AGCCTATAGT GCTGCCAGAA AAACACAGCT GGACTGTCAA TGACATACAG
      AGGACTATTT ACCTGTCATG TCGGATATCA CGACGGTCTT TTTGTGTCGA CCTGACAGTT ACTGTATGTC

8051  AAGTTAGTGG GGAAATTGAA TACCGCAAGT CAGATTTACC CAGGGATTAA AGTAAGGCAA TTATGTAAAC
      TTCAATCACC CCTTTAACTT ATGGCGTTCA GTCTAAATGG GTCCCTAATT TCATTCCGTT AATACATTTG

8121  TCCTTAGAGG AACCAAAGCA CTAACAGAAG TAATACCACT AACAGAAGAA GCAGAGCTAG AACTGGCAGA
      AGGAATCTCC TTGGTTTCGT GATTGTCTTC ATTATGGTGA TTGTCTTCTT CGTCTCGATC TTGACCGTCT

8191  AAACAGAGAG ATTCTAAAAG AACCAGTACA TGGAGTGTAT TATGACCCAT CAAAAGACTT AATAGCAGAA
      TTTGTCTCTC TAAGATTTTC TTGGTCATGT ACCTCACATA ATACTGGGTA GTTTTCTGAA TTATCGTCTT
```

*FIG. 14T*

```
8261  ATACAGAAGC AGGGGCAAGG CCAATGGACA TATCAAATTT ATCAAGAGCC ATTTAAAAAT CTGAAAACAG
      TATGTCTTCG TCCCCGTTCC GGTTACCTGT ATAGTTTAAA TAGTTCTCGG TAAATTTTTA GACTTTTGTC

8331  GAAATATGC AAGAATGAGG GGTGCCCACA CTAATGATGT AAAACAATTA ACAGAGGCAG TGCAAAAAAT
      CTTTTATACG TTCTTACTCC CCACGGGTGT GATTACTACA TTTTGTTAAT TGTCTCCGTC ACGTTTTTTA

8401  AACCACAGAA AGCATAGTAA GACTCCTAAA TTTAAACTAC CCATACAAAA GGAAACATGG
      TTGGTGTCTT TCGTATCATT CTGAGGATTT AAATTTGATG GGTATGTTTT CCTTTGTACC

8471  GAAACATGGT GGACAGAGTA TTGGCCAAGC ACCTGGATTC CTGAGTGGA GTTTGTTAAT ACCCCTCCTT
      CTTTGTACCA CCTGTCTCAT AACCGTTCG TGGACCTAAG GACTCACCCT CAAACAATTA TGGGGAGGAA

8541  TAGTGAAATT ATGGTACCAG TTAGAGAAAG AACCCATAGT AACCTTCTATG TAGATGGGGC
      ATCACTTTAA TACCATGGTC AATCTCTTC TTGGGTATCA TGGAAGATAC ATCTACCCCG

8611  AGCTAACAGG CAGACTAAAT TAGGAAAAGC AGGATATGTT ACTAACAAAG GAAGACAAAA GGTTGTCCCC
      TCGATTGTCC CTCTGATTTA ATCCTTTTCG TCCTATACAA TGATTGTTTC CTTCTGTTTT CCAACAGGGG
```

FIG. 14U

```
8681  CTAACTAACA CAACAAATCA GAAAACTCAG TTACAAGCAA TTTATCTAGC TTTGCAGGAT TCAGGATTAG
      GATTGATTGT GTTGTTTAGT CTTTTGAGTC AATGTTCGTT AATAGATCG AAACGTCCTA AGTCCTAATC

8751  AAGTAAACAT AGTAACAGAC TCACAATATG CATTAGGAAT CATTCAAGCA CAACCAGATA AAAGTGAATC
      TTCATTTGTA TCATTGTCTG AGTGTTATAC GTAATCCTTA GTAAGTTCGT GTTGGTCTAT TTTCACTTAG

8821  AGAGTTAGTC AATCAAATAA TAGAGCAGTT AATAAAAAAG GAAAAGGTCT ATCTGGCATG GGTACCAGCA
      TCTCAATCAG TTAGTTTATT ATCTCGTCAA TTATTTTTTC CTTTTCCAGA TAGACCGTAC CCATGGTCGT

8891  CACAAAGGAA TTGGAGGAAA TGAACAAGTA GATAAATTAG TCAGTGCTGG AATCAGGAAA ATACTATTT
      GTGTTTCCTT AACCTCCTTT ACTGTTCAT CTATTTAATC AGTCACGACC TTAGTCCTTT TATGATAAAA

8961  TAGATGGAAT AGATAAGGGC CAAGATGAAC ATTAGTTTTT ATGTCGACCT GCAGGGAAAG TTTTATAGGT
      ATCTACCTTA TCTATTCCGG GTTCTACTTG TAATCAAAAA TACAGCTGGA CGTCCCTTTC AAAATATCCA

9031  AGTTGATAGA ACAAAATACA TAATTTGTA AAAATAAATC ACTTTTTATA CTAATATGAC ACGATTACCA
      TCAACTATCT TGTTTTATGT ATTAAAACAT TTTATTTAG TGAAAAATAT GATTATACTG TGCTAATGGT
```

*FIG. 14V*

```
9101  ATACTTTTGT TACTAATATC ATTAGTATAC GCTACACCTT TTCCTCAGAC ATCTAAAAAA ATAGGTGATG
      TATGAAACA  ATGATTATAG TAATCATATG CGATGTGGAA AAGGAGTCTG TAGATTTTTT TATCCACTAC

9171  ATGCAACTTT ATCATGTAAT CGAAATAATA CAAATGACTA CGTTGTTATG AGTGCCTTGGT ATAAGGAGCC
      TACGTTGAAA TAGTACATTA GCTTTATTAT GTTTACTGAT GCAACAATAC TCACGAACCA TATTCCTCGG

9241  CAATTCCATT ATTCTTTTAG CTGCTAAAAG CGACGTCTTG TATTTTGATA ATTATACCAA GGATAAAATA
      GTTAAGGTAA TAAGAAAATC GACGATTTTC GCTGCAGAAC ATAAAACTAT TAATATGGTT CCTATTTTAT

9311  TCTTACGACT CTCCATACGA TGATCTAGTT ACAACTATCA CAATTAAAATC ATTGACTGCT AGAGATGCCG
      AGAATGCTGA GAGGTATGCT ACTAGATGCT TGTTGATAGT GTTAATTTAG TAACTGACGA TCTCTACGGC

9381  GTACTTATGT ATGTGCATTC TTTATGACAT CGCCTACAAA CGGATGTGTT AAAGTAGATT ATGAAGAATA
      CATGAATACA TACACGTAAG AAATACTGTA GCGGATGTTT ACTGACTGACTA TTTCATCTAA TACTTCTTAT

9451  CTCCACAGAG TTGATTGTAA ATACAGATAG TGAATCGACT ATAGACATAA TACTATCTGG ATCTACACAT
      GAGGTGTCTC AACTAACATT TATGTCTATC ACTTAGCTGA TATCTGTATT ATGATAGACC TAGATGTGTA
```

FIG. 14W

```
9521  TCACCAGAAA CTAGTTAAGC TTGTCTCCCT ATAGTGAGTC GTATTAGAGC TTGGGGTAAT CATGGTCATA
      AGTGGTCTTT GATCAATTCG AACAGAGGGA TATCACTCAG CATAATCTCG AACCGCATTA GTACCAGTAT

9591  GCTGTTTCCT GTGTGAAATT GTTATCCGCT CACAATTCCA CACAACATAC GAGCCGGAAG CATAAAGTGT
      CGACAAAGGA CACACTTTAA CAATAGGCGA GTGTTAAGGT GTGTTGTATG CTCGGCCTTC GTATTTCACA

9661  AAAGCCTGGG GTGCCTAATG AGTGAGCTAA CTCACATTAA TTGCGTTGCG CTCACTGCCC GCTTTCGAGT
      TTTCGGACCC CACGGATTAC TCACTCGATT GAGTGTAATT AACGCAACGC GAGTGACGGG CGAAAGCTCA

9731  CGGAAAACCT GTCGTGCCAG CTGCATTAAT GAATCGGCCA ACGCGCGGGG AGAGGCGGTT TGCGTATTGG
      GCCTTTTGGA CAGCACGGTC GACGTAATTA CTTAGCCGGT TGCGCGCCCC TCTCCGCCAA ACGCATAACC

9801  GCGCTCTTCC GCTTCCTCGC TCACTGACTC GCTGCGCTCG GTCGTTCGGC TGCGGCGAGC GGTATCAGCT
      CGCGAGAAGG CGAAGGAGCG AGTGACTGAG CGACGCGAGC CAGCAAGCCG ACGCCGCTCG CCATAGTCGA

9871  CACTCAAAGG CGGTAATACG GTTATCCACA GAATCAGGGG ATAACGCAGG AAAGAACATG TGAGCAAAAG
      GTGAGTTTCC GCCATTATGC CAATAGGTGT CTTAGTCCCC TATTGCGTCC TTTCTTGTAC ACTCGTTTTC

9941  GCCAGCAAAA GGCCAGGAAC CGTAAAAAGG CCGCGTTGCT GGCGTTTTTC GATAGGCTCC GCCCCCCTGA
      CGGTCGTTTT CCGGTCCTTG GCATTTTTCC GGCGCAACGA CCGCAAAAAG CTATCCGAGG CGGGGGGACT
```

FIG. 14X

```
10011  CGAGCATCAC AAAAATCGAC GCTCAAGTCA GAGGTGGCGA AACCCGACAG GACTATAAAG ATACCAGGCG
       GCTCGTAGTG TTTTTAGCTG CGAGTTCAGT CTCCACCGCT TTGGGCTGTC CTGATATTTC TATGGTCCGC

10081  TTTCCCCCTG GAAGCTCCCT CGTGCGCTCT CCTGTTCCGA CCCTGCCCCT TACCGGATAC CTGTCCGCCT
       AAAGGGGGAC CTTCGAGGGA GCACGCGAGA GGACAAGGCT GGGACGGCGA ATGGCCTATG GACAGGCGGA

10151  TTCTCCCTTC GGGAAGCGTG GCGCTTTCTC ATAGCTCACG CTGTAGGTAT CTCAGTTCGG TGTAGGTCGT
       AAGAGGGAAG CCCTTCGCAC CGCGAAAGAG TATCGAGTGC GACATCCATA GAGTCAAGCC ACATCCAGCA

10221  TCGCTCCAAG CTGGGCTGTG TGCACGAACC CCCCGTTCAG CCCGACCGCT GCGCCTTATC CGGTAACTAT
       AGCGAGGTTC GACCCGACAC ACGTGCTTGG GGGGCAAGTC GGGCTGGCGA CGCGGAATAG GCCATTGATA

10291  CGTCTTGAGT CCAACCCGGT AAGACACGAC TTATCGCCAC TGGCAGCAGC CACTGGTAAC AGGATTAGCA
       GCAGAACTCA GGTTGGGCCA TTCTGTGCTG AATAGCGGTG ACCGTCGTCG GTGACCATTG TCCTAATCGT

10361  GAGCGAGGTA TGTAGGCGGT GCTACAGAGT TCTTGAAGTG GTGGCCTAAC TACGGCTACA CTAGAAGGAC
       CTCGCTCCAT ACATCCGCCA CGATGTCTCA AGAACTTCAC CACCGGATTG ATGCCGATGT GATCTTCCTG

10431  AGTATTTGGT ATCTGCGCTC TGCTGAAGCC AGTTACCTTC GGAAAAAGAG TTGGTAGCTC TTGATCCGGC
       TCATAAACCA TAGACGCGAG ACGACTTCGG TCAATGGAAG CCTTTTTCTC AACCATCGAG AACTAGGCCG
```

*FIG. 14Y*

```
10501  AAACAAACCA CCGCTGGTAG CGGTGGTTTT TTTGTTTGCA AGCAGGAGAT TACGGGCAGA AAAAAGGAT
       TTTGTTTGGT GGCGACCATC GCCACCAAAA AAACAAACGT TCGTCGTCTA ATGCCCGTCT TTTTTTCCTA

10571  CTCAAGAAGA TCCTTTGATC TTTTCTACGG GGTCTGACGC TCAGTGGAAC GAAAACTCAC GTTAAGGAT
       GAGTTCTTCT AGGAAACTAG AAAAGATGCC CCAGACTGCG AGTCACCTTG CTTTTGAGTG CAATTCCCTA

10641  TTTGGTCATG AGATTATCAA AAAGGATCTT CACCCTAGATC CTTTTAAATT AAAAATGAAG TTTTAAATCA
       AAACCAGTAC TCTAATAGTT TTTCCTAGAA GTGGATCTAG GAAAATTTAA TTTTTACTTC AAAATTTAGT

10711  ATCTAAAGTA TATATGAGTA AACTTGGTCT GACACGTTACC AATGCTTAAT CAGTGAGGCA CCTATCTCAG
       TAGATTTCAT ATATACTCAT TTGAACCAGA CTGTCAATGG TTACGAATTA GTCACTCCGT GGATAGAGTC

10781  CGATCGTGCT ATTTCGTTCA TCCATAGTTG CCTGACTCCC CGTCGTGTAG ATAACTACGA TACGGGAGGG
       GCTAGACAGA TAAAGCAAGT AGGTATCAAC GGACTGAGGG GCAGCACATC TATTGATGCT ATGCCCTCCC

10851  CTTACCATCT GGCCCCAGTG CTGCAATGAT ACCGCGAGAC CCACGCTCAC CGGCTCCAGA TTTATCAGCA
       GAATGGTAGA CCGGGGTCAC GACGTTACTA TGGCGCTCTG GGTGCGAGTG GCCGAGGTCT AAATAGTCGT

10921  ATAAACCAGC CAGCCGGAAG GGCCGAGCGC AGAAGTGGTC CTGCAACTTT ATCCGCCTCC ATCCAGTCTA
       TATTTGGTCG GTCGGCCTTC CCGGCTCGCG TCTTCACCAG GACGTTGAAA TAGGCGGAGG TAGGTCAGAT
```

FIG. 14Z

```
10991  TTAATTGTTG CCGGGAAGCT AGAGTAAGTA GTTCGCCAGT TAATAGTTTG CGCAACGTTG TTGGCATTGC
       AATTAACAAC GGCCCTTCGA TCTCATTCAT CAAGCGGTCA ATTATCAAAC GCGTTGCAAC AACCGTAACG

11061  TACAGGCATC GTGGTGTCAC GCTCGTCGTT TGGTATGGCT TCATTCAGCT CGGGTTCCCA ACGATCAAGG
       ATGTCCGTAG CACCACAGTG CGAGCAGCAA ACCATACCGA AGTAAGTCGA GCCCAAGGGT TGCTAGTTCC

11131  CGAGTTACAT GATCCCCCAT GTTGTGCAAA AAGCGGTTA GCTCCTTCGG TCCTCCGATC GTTGTCAGAA
       GCTCAATGTA CTAGGGGGTA CAACACGTTT TTTCGCCAAT CGAGGAAGCC AGGAGGCTAG CAACAGTCTT

11201  GTAAGTTGGC CGCAGTGTTA TCACTCATGG TTATGGCAGC ACTGCATAAT TCTCTTACTG TCATGCCATC
       CATTCAACCG GCGTCACAAT AGTGAGTACC AATACCGTCG TGACGTATTA AGAGAATGAC AGTACGGTAG

11271  CGTAAGATGC TTTTCTGTGA CTGGTGAGTA CTCAACCAAG TCATTCTGAG AATAGTGTAT GGGGCGACCG
       GCATTCTACG AAAAGACACT GACCACTCAT GAGTTGGTTC AGTAAGACTC TTATCACATA CCCCGCTGGC

11341  AGTGCTCTT GCCCGGGCTC AATACCCGCC CACATAGCAG AACTTTAAAA GTGCTCATCA
       TCAACGAGAA CGGGCCCGAG TTATGGGCGG GTGTATCGTC TTGAAATTTT CACGAGTAGT
```

*FIG. 14AA*

```
11411  TTGGAAAACG TTCTTCGGGG CGAAAAACTCT CAAGGATCTT ACCGCTGTTG AGATCCAGTT CGATGTAACC
       AACCTTTTGC AAGAAGCCCC GCTTTTTGAGA GTTCCTAGAA TGGCGACAAC TCTAGGTCAA GCTACATTGG

11481  CACTCCTGCA CCCAACTGAT CTTCAGCATC TTTTACTTTC ACCAGCCTTT CTGGGTGAGC AAAAACAGGA
       GTGAGGACGT GGGTTGACTA GAAGTCGTAG AAAATGAAAG TGGTCGGAAA GACCCACTCG TTTTTGTCCT

11551  AGGCAAAATG CCGCAAAAAA GGGAATAAGG GCGACACGGA AATGTTGAAT ACTCATATCC TTCCTTTTTC
       TCCGTTTTAC GGCGTTTTTT CCCTTATTCC CGCTGTGCCT TTACAACTTA TGAGTATAGG AAGGAAAAAG

11621  AATATTATTG AAGCATTTAT CAGGGTTATT GTCTCATGAG CGGATACATA TTTGAATGTA TTTAGAAAAA
       TTATAATAAC TTCGTAAATA GTCCCAATAA CAGAGTACTC GCCTATGTAT AAACTTACAT AAATCTTTTT

11691  TAAACAAATA GGGGTTCCGC GCACATTTCC CCGAAAAGTG CCACCTGACC TCTAAGAAAC CATTATTATC
       ATTTGTTTAT CCCCAAGGCG CGTGTAAAGG GGCTTTTCAC GGTGGACTGG AGATTCTTTG GTAATAATAG

11761  ATGACATTAA CCTATAAAAA TAGGCGTATC ACGAGGCCCT TTCGTCTCGC GCGTTTCGGT GATGACGGTG
       TACTGTAATT GGATATTTTT ATCCGCATAG TGCTCCGGGA AAGCAGAGCG CGCAAAGCCA CTACTGCCAC
```

FIG. 14AB

```
11831  AAAACCTCTG ACACATGCAG CTCCCGGAGA CGGTCACAGC TTGTCTGTAA GCGGATGCCCG GGAGCAGACA
       TTTTGGAGAC TGTGTACGTC GAGGGCCTCT GCCAGTGTCG AACAGACATT CGCCTACGGC CCTCGTCTGT

11901  AGCCCGTCAG GGCGGGTCAG CGGGTGTTGG CGGGTGTCGG GGCTGGCTTA ACTATGCGGC ATCAGAGCAG
       TCGGGCAGTC CCCGCCAGTC GCCCACAACC GCCCACAGCC CCGACCGAAT TGATACGCCG TAGTCTCGTC

11971  ATTGTACTGA GAGTGCACCA TATGCGGGTGT GAAATACCGC ACAGATGCGT AAGGAGAAAA TACCGCATCA
       TAACATGACT CTCACGTGGT ATACGCCACA CTTTATGGCG TGTCTACGCA TTCCTCTTTT ATGGCGTAGT

12041  GGCGCCATTC GCCATTCAGG CTCGCGGAACT GTTGGGAAGG GCCATCGGTC CGGCTATTACG
       CCGGGGTAAG CGGTAAGTCC GACGCCGTTGA CAACCCTTCC CGGTAGCCAC GCCGGAGAA GCGATAATGC

12111  CCAGCTGGCC AAAAGGGGAT GTGCTGCAAG GCGATTAAGT TGGGTAACGC CAGGGTTTTC CCAGTCACGA
       GGTCGACCGG TTTCCCCCTA CACGACGTTC CGCTAATTCA ACCCATTGCG GTCCCAAAAG GGTCAGTGCT

12181  CGTTGTAAAA CGACGGCCAG TGAATTGGAT TTAGGTGACA CTATA
       GCAACATTTT GCTGCCGGTC ACTTAACCTA AATCCACTGT GATAT
```

*FIG. 14AC*

Text File of pLW-48 and the Included Individual HIV Genes and Their Promoters

Entire pLW-48 plasmid sequence:

GAATTCGTTGGTGGTCGCCATGGATGGTGTTATTGTATACTGTCTAAACGCG
TTAGTAAAACATGGCGAGGAAATAAATCATATAAAAAATGATTTCATGATTAA
ACCATGTTGTGAAAAAGTCAAGAACGTTCACATTGGCGGACAATCTAAAAAC
AATACAGTGATTGCAGATTTGCCATATATGGATAATGCGGTATCCGATGTAT
GCAATTCACTGTATAAAAAGAATGTATCAAGAATATCCAGATTTGCTAATTTG
ATAAAGATAGATGACGATGACAAGACTCCTACTGGTGTATATAATTATTTTAA
ACCTAAAGATGCCATTCCTGTTATTATATCCATAGGAAAGGATAGAGATGTTT
GTGAACTATTAATCTCATCTGATAAAGCGTGTGCGTGTATAGAGTTAAATTCA
TATAAAGTAGCCATTCTTCCCATGGATGTTTCCTTTTTTACCAAAGGAAATGC
ATCATTGATTATTCTCCTGTTTGATTTCTCTATCGATGCGGCACCTCTCTTAA
GAAGTGTAACCGATAATAATGTTATTATATCTAGACACCAGCGTCTACATGA
CGAGCTTCCGAGTTCCAATTGGTTCAAGTTTTACATAAGTATAAAGTCCGAC
TATTGTTCTATATTATATATGGTTGTTGATGGATCTGTGATGCATGCAATAGC
TGATAATAGAACTTACGCAAATATTAGCAAAAATATATTAGACAATACTACAA
TTAACGATGAGTGTAGATGCTGTTATTTTGAACCACAGATTAGGATTCTTGAT
AGAGATGAGATGCTCAATGGATCATCGTGTGATATGAACAGACATTGTATTA
TGATGAATTTACCTGATGTAGGCGAATTTGGATCTAGTATGTTGGGGAAATA
TGAACCTGACATGATTAAGATTGCTCTTTCGGTGGCTGGGTACCAGGCGCG
CCTTTCATTTTGTTTTTTTCTATGCTATAAATGGTACGTCCTGTAGAAACCCC
AACCCGTGAAATCAAAAAACTCGACGGCCTGTGGGCATTCAGTCTGGATCG
CGAAAACTGTGGAATTGATCAGCGTTGGTGGGAAAGCGCGTTACAAGAAAG
CCGGGCAATTGCTGTGCCAGGCAGTTTTAACGATCAGTTCGCCGATGCAGA
TATTCGTAATTATGCGGGCAACGTCTGGTATCAGCGCGAAGTCTTTATACCG
AAAGGTTGGGCAGGCCAGCGTATCGTGCTGCGTTTCGATGCGGTCACTCAT
TACGGCAAAGTGTGGGTCAATAATCAGGAAGTGATGGAGCATCAGGGCGG
CTATACGCCATTTGAAGCCGATGTCACGCCGTATGTTATTGCCGGGAAAAG
TGTACGTATCACCGTTTGTGTGAACAACGAACTGAACTGGCAGACTATCCC
GCCGGGAATGGTGATTACCGACGAAAACGGCAAGAAAAAGCAGTCTTACTT
CCATGATTTCTTTAACTATGCCGGAATCCATCGCAGCGTAATGCTCTACACC
ACGCCGAACACCTGGGTGGACGATATCACCGTGGTGACGCATGTCGCGCA
AGACTGTAACCACGCGTCTGTTGACTGGCAGGTGGTGGCCAATGGTGATGT
CAGCGTTGAACTGCGTGATGCGGATCAACAGGTGGTTGCAACTGGACAAG
GCACTAGCGGGACTTTGCAAGTGGTGAATCCGCACCTCTGGCAACCGGGT
GAAGGTTATCTCTATGAACTGTGCGTCACAGCCAAAAGCCAGACAGAGTGT
GATATCTACCCGCTTCGCGTCGGCATCCGGTCAGTGGCAGTGAAGGGCGA
ACAGTTCCTGATTAACCACAAACCGTTCTACTTTACTGGCTTTGGTCGTCAT
GAAGATGCGGACTTGCGTGGCAAAGGATTCGATAACGTGCTGATGGTGCAC
GACCACGCATTAATGGACTGGATTGGGGCCAACTCCTACCGTACCTCGCAT
TACCCTTACGCTGAAGAGATGCTCGACTGGGCAGATGAACATGGCATCGTG

FIG. 15A

```
GTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAAC
GGGGAAACTCAGCAAGCGCACTTACAGGCGATTAAAGAGCTGATAGCGCGT
GACAAAAACCACCCAAGCGTGGTGATGTGGAGTATTGCCAACGAACCGGAT
ACCCGTCCGCAAGGTGCACGGGAATATTTCGCGCCACTGGCGGAAGCAAC
GCGTAAACTCGACCCGACGCGTCCGATCACCTGCGTCAATGTAATGTTCTG
CGACGCTCACACCGATACCATCAGCGATCTCTTTGATGTGCTGTGCCTGAA
CCGTTATTACGGATGGTATGTCCAAAGCGGCGATTTGGAAACGGCAGAGAA
GGTACTGGAAAAGAACTTCTGGCCTGGCAGGAGAAACTGCATCAGCCGAT
TATCATCACCGAATACGGCGTGGATACGTTAGCCGGGCTGCACTCAATGTA
CACCGACATGTGGAGTGAAGAGTATCAGTGTGCATGGCTGGATATGTATCA
CCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAA
AGGGATCTTCACTCGCGACCGCAAACCGAAGTCGGCGGCTTTTCTGCTGCA
AAAACGCTGGACTGGCATGAACTTCGGTGAAAAACCGCAGCAGGGAGGCA
AACAATGAGAGCTCGGTTGTTGATGGATCTGTGATGCATGCAATAGCTGATA
ATAGAACTTACGCAAATATTAGCAAAAATATATTAGACAATACTACAATTAAC
GATGAGTGTAGATGCTGTTATTTTGAACCACAGATTAGGATTCTTGATAGAG
ATGAGATGCTCAATGGATCATCGTGTGATATGAACAGACATTGTATTATGAT
GAATTTACCTGATGTAGGCGAATTTGGATCTAGTATGTTGGGGAAATATGAA
CCTGACATGATTAAGATTGCTCTTTCGGTGGCTGGCGGCCCGCTCGAGTAA
AAAATGAAAAAATATTCTAATTTATAGGACGGTTTTGATTTTCTTTTTTTCTAT
GCTATAAATAATAAATAGCGGCCGCACCATGAAAGTGAAGGGGATCAGGAA
GAATTATCAGCACTTGTGGAAATGGGGCATCATGCTCCTTGGGATGTTGATG
ATCTGTAGTGCTGTAGAAAATTTGTGGGTCACAGTTTATTATGGGGTACCTG
TGTGGAAAGAAGCAACCACCACTCTATTTTGTGCATCAGATGCTAAAGCATA
TGATACAGAGGTACATAATGTTTGGGCCACACATGCCTGTGTACCCACAGA
CCCCAACCCACAAGAAGTAGTATTGGAAAATGTGACAGAAAATTTTAACATG
TGGAAAAATAACATGGTAGAACAGATGCATGAGGATATAATCAGTTTATGGG
ATCAAAGCCTAAAGCCATGTGTAAAATTAACCCCACTCTGTGTTACTTTAAAT
TGCACTGATTTGAGGAATGTTACTAATATCAATAATAGTAGTGAGGGAATGA
GAGGAGAAATAAAAAACTGCTCTTTCAATATCACCACAAGCATAAGAGATAA
GGTGAAGAAAGACTATGCACTTTTcTATAGACTTGATGTAGTACCAATAGATA
ATGATAATACTAGCTATAGGTTGATAAATTGTAATACCTCAACCATTACACAG
GCCTGTCCAAAGGTATCCTTTGAGCCAATTCCCATACATTATTGTACCCCGG
CTGGTTTTGCGATTCTAAAGTGTAAAGACAAGAAGTTCAATGGAACAGGGCC
ATGTAAAAATGTCAGCACAGTACAATGTACACATGGAATTAGGCCAGTAGTG
TCAACTCAACTGCTGTTAAATGGCAGTCTAGCAGAAGAAGAGGTAGTAATTA
GATCTAGTAATTTCACAGACAATGCAAAAAACATAATAGTACAGTTGAAAGAA
TCTGTAGAAATTAATTGTACAAGACCCAACAACAATACAAGGAAAAGTATAC
ATATAGGACCAGGAAGAGCATTTTATACAACAGGAGAAATAATAGGAGATAT
AAGACAAGCACATTGCAACATTAGTAGAACAAAATGGAATAACACTTTAAAT
CAAATAGCTACAAAATTAAAAGAACAATTTGGGAATAATAAAACAATAGTCTT
TAATCAATCCTCAGGAGGGGACCCAGAAATTGTAATGCACAGTTTTAATTGT
GGAGGGGAATTCTTCTACTGTAATTCAACACAACTGTTTAATAGTACTTGGA
ATTTTAATGGTACTTGGAATTTAACACAATCGAATGGTACTGAAGGAAATGA
```

FIG. 15B

```
CACTATCACACTCCCATGTAGAATAAAACAAATTATAAATATGTGGCAGGAA
GTAGGAAAAGCAATGTATGCCCCTCCCATCAGAGGACAAATTAGATGCTCAT
CAAATATTACAGGGCTAATATTAACAAGAGATGGTGGAACTAACAGTAGTGG
GTCCGAGATCTTCAGACCTGGGGGAGGAGATATGAGGGACAATTGGAGAA
GTGAATTATATAAATATAAAGTAGTAAAAATTGAACCATTAGGAGTAGCACCC
ACCAAGGCAAAAAGAAGAGTGGTGCAGAGAGAAAAAAGAGCAGTGGGAAC
GATAGGAGCTATGTTCCTTGGGTTCTTGGGAGCAGCAGGAAGCACTATGGG
CGCAGCGTCAATAACGCTGACGGTACAGGCCAGACTATTATTGTCTGGTAT
AGTGCAACAGCAGAACAATTTGCTGAGGGCTATTGAGGCGCAACAGCATCT
GTTGCAACTCACAGTCTGGGGCATCAAGCAGCTCCAGGCAAGAGTCCTGG
CTGTGGAAAGATACCTAAGGGATCAACAGCTCCTAGGGATTTGGGGTTGCT
CTGGAAAACTCATCTGCACCACTGCTGTGCCTTGGAATGCTAGTTGGAGTA
ATAAAACTCTGGATATGATTTGGGATAACATGACCTGGATGGAGTGGGAAA
GAGAAATCGAAAATTACACAGGCTTAATATACACCTTAATTGAGGAATCGCA
GAACCAACAAGAAAAGAATGAACAAGACTTATTAGCATTAGATAAGTGGGCA
AGTTTGTGGAATTGGTTTGACATATCAAATTGGCTGTGGTATGTAAAAATCTT
CATAATGATAGTAGGAGGCTTGATAGGTTTAAGAATAGTTTTTACTGTACTTT
CTATAGTAAATAGAGTTAGGCAGGGATACTCACCATTGTCATTTCAGACCCA
CCTCCCAGCCCCGAGGGGACCCGACAGGCCCGAAGGAATCGAAGAAGAAG
GTGGAGACAGAGACTAATTTTTATGCGGCCGCTGGTACCCAACCTAAAAATT
GAAAATAAATACAAAGGTTCTTGAGGGTTGTGTTAAATTGAAAGCGAGAAAT
AATCATAAATAAGCCCGGGGATCCTCTAGAGTCGACACCATGGGTGCGAGA
GCGTCAGTATTAAGCGGGGGAGAATTAGATCGATGGGAAAAAATTCGGTTA
AGGCCAGGGGGAAAGAAAAAATATAAATTAAAACATATAGTATGGGCAAGCA
GGGAGCTAGAACGATTCGCAGTTAATCCTGGCCTGTTAGAAACATCAGAAG
GCTGTAGACAAATACTGGGACAGCTACAACCATCCCTTCAGACAGGATCAG
AAGAACTTAGATCATTATATAATACAGTAGCAACCCTCTATTGTGTGCATCAA
AGGATAGAGATAAAAGACACCAAGGAAGCTTTAGACAAGATAGAGGAAGAG
CAAAACAAAAGTAAGAAAAAAGCACAGCAAGCAGCAGCTGACACAGGACAC
AGCAATCAGGTCAGCCAAAATTACCCTATAGTGCAGAACATCCAGGGGCAA
ATGGTACATCAGGCCATATCACCTAGAACTTTAAATGCATGGGTAAAAGTAG
TAGAAGAGAAGGCTTTCAGCCCAGAAGTGATACCCATGTTTTCAGCATTATC
AGAAGGAGCCACCCCACAAGATTTAAACACCATGCTAAACACAGTGGGGGG
ACATCAAGCAGCCATGCAAATGTTAAAAGAGACCATCAATGAGGAAGCTGC
AGAATGGGATAGAGTGCATCCAGTGCATGCAGGGCCTATTGCACCAGGCCA
GATGAGAGAACCAAGGGGAAGTGACATAGCAGGAACTACTAGTACCCTTCA
GGAACAAATAGGATGGATGACAAATAATCCACCTATCCCAGTAGGAGAAATT
TATAAAAGATGGATAATCCTGGGATTAAATAAAATAGTAAGAATGTATAGCCC
TACCAGCATTCTGGACATAAGACAAGGACCAAAAGAACCCTTTAGAGACTAT
GTAGACCGGTTCTATAAAACTCTAAGAGCCGAGCAAGCTTCACAGGAGGTA
AAAAATTGGATGACAGAAACCTTGTTGGTCCAAAATGCGAACCCAGATTGTA
AGACTATTTTAAAAGCATTGGGACCAGCGGCTACACTAGAAGAAATGATGAC
AGCATGTCAGGGAGTAGGAGGACCCGGCCATAAGGCAAGAGTTTTGGCTG
AAGCAATGAGCCAAGTAACAAATTCAGCTACCATAATGATGCAGAGAGGCA
ATTTTAGGAACCAAAGAAAGATTGTTAAGTGTTTCAATTGTGGCAAAGAAGG
GCACACAGCCAGAAATTGCAGGGCCCCTAGGAAAAAGGGCTGTTGGAAAT
```

*FIG. 15C*

```
GTGGAAAGGAAGGACACCAAATGAAAGATTGTACTGAGAGACAGGCTAATT
TTTTAGGGAAGATCTGGCCTTCCTACAAGGGAAGGCCAGGGAATTTTCTTCA
GAGCAGACCAGAGCCAACAGCCCCACCAGAAGAGAGCTTCAGGTCTGGGG
TAGAGACAACAACTCCCCCTCAGAAGCAGGAGCCGATAGACAAGGAACTGT
ATCCTTTAACTTCCCTCAGATCACTCTTTGGCAACGACCCCTCGTCACAATA
AAGATAGGGGGGCAACTAAAGGAAGCTCTATTAGATACAGGAGCAGATGAT
ACAGTATTAGAAGAAATGAGTTTGCCAGGAAGATGGAAACCAAAATGATAG
GGGGAATTGGAGGTTTTATCAAAGTAAGACAGTATGATCAGATACTCATAGA
AATCTGTGGACATAAAGCTATAGGTACAGTATTAGTAGGACCTACACCTGTC
AACATAATTGGAAGAAATCTGTTGACTCAGATTGGTTGCACTTTAAATTTTCC
CATTAGCCCTATTGAGACTGTACCAGTAAAATTAAAGCCAGGAATGGATGGC
CCAAAAGTTAAACAATGGCCATTGACAGAAGAAAAAATAAAAGCATTAGTAG
AAATTTGTACAGAAATGGAAAAGGAAGGGAAAATTTCAAAAATTGGGCCTGA
GAATCCATACAATACTCCAGTATTTGCCATAAAGAAAAAAGACAGTACTAAAT
GGAGGAAATTAGTAGATTTCAGAGAACTTAATAAGAGAACTCAAGACTTCTG
GGAAGTTCAATTAGGAATACCACATCCCGCAGGGTTAAAAAAGAAAAAATCA
GTAACAGTACTGGATGTGGGTGATGCATATTTTTCAGTTCCCTTAGATGAAG
ACTTCAGGAAGTATACTGCATTTACCATACCTAGTATAAACAATGAGACACC
AGGGATTAGATATCAGTACAATGTGCTTCCACAGGGATGGAAAGGATCACC
AGCAATATTCCAAAGTAGCATGACAAAAATCTTAGAGCCTTTTAAAAAACAAA
ATCCAGACATAGTTATCTATCAATACATGAACGATTTGTATGTAGGATCTGAC
TTAGAAATAGGGCAGCATAGAACAAAAATAGAGGAGCTGAGACAACATCTG
TTGAGGTGGGGACTTACCACACCAGACAAAAAACATCAGAAAGAACCTCCA
TTCCTTTGGATGGGTTATGAACTCCATCCTGATAAATGGACAGTACAGCCTA
TAGTGCTGCCAGAAAAAGACAGCTGGACTGTCAATGACATACAGAAGTTAG
TGGGGAAATTGAATACCGCAAGTCAGATTTACCCAGGGATTAAAGTAAGGC
AATTATGTAAACTCCTTAGAGGAACCAAAGCACTAACAGAAGTAATACCACT
AACAGAAGAAGCAGAGCTAGAACTGGCAGAAAACAGAGAGATTCTAAAAGA
ACCAGTACATGGAGTGTATTATGACCCATCAAAAGACTTAATAGCAGAAATA
CAGAAGCAGGGGCAAGGCCAATGGACATATCAAATTTATCAAGAGCCATTT
AAAAATCTGAAAACAGGAAAATATGCAAGAATGAGGGGTGCCCACACTAAT
GATGTAAAACAATTAACAGAGGCAGTGCAAAAAATAACCACAGAAAGCATAG
TAATATGGGGAAAGACTCCTAAATTTAAACTACCCATACAAAAGGAAACATG
GGAAACATGGTGGACAGAGTATTGGCAAGCCACCTGGATTCCTGAGTGGGA
GTTTGTTAATACCCCTCCTTTAGTGAAATTATGGTACCAGTTAGAGAAAGAA
CCCATAGTAGGAGCAGAAACCTTCTATGTAGATGGGGCAGCTAACAGGGAG
ACTAAATTAGGAAAAGCAGGATATGTTACTAACAAAGGAAGACAAAAGGTTG
TCCCCCTAACTAACACAACAAATCAGAAAACTCAGTTACAAGCAATTTATCTA
GCTTTGCAGGATTCAGGATTAGAAGTAAACATAGTAACAGACTCACAATATG
CATTAGGAATCATTCAAGCACAACCAGATAAAAGTGAATCAGAGTTAGTCAA
TCAAATAATAGAGCAGTTAATAAAAAAGGAAAAGGTCTATCTGGCATGGGTA
CCAGCACACAAAGGAATTGGAGGAAATGAACAAGTAGATAAATTAGTCAGT
GCTGGAATCAGGAAAATACTATTTTTAGATGGAATAGATAAGGCCCAAGATG
AACATTAGTTTTTATGTCGACCTGCAGGGAAAGTTTTATAGGTAGTTGATAG
AACAAAATACATAATTTTGTAAAAATAAATCACTTTTTATACTAATATGACACG
ATTACCAATACTTTTGTTACTAATATCATTAGTATACGCTACACCTTTTCCTCA
```

*FIG. 15D*

```
GACATCTAAAAAAAATAGGTGATGATGCAACTTTATCATGTAATCGAAATAATA
CAAATGACTACGTTGTTATGAGTGCTTGGTATAAGGAGCCCAATTCCATTAT
TCTTTTAGCTGCTAAAAGCGACGTCTTGTATTTTGATAATTATACCAAGGATA
AAATATCTTACGACTCTCCATACGATGATCTAGTTACAACTATCACAATTAAA
TCATTGACTGCTAGAGATGCCGGTACTTATGTATGTGCATTCTTTATGACATC
GCCTACAAATGACACTGATAAAGTAGATTATGAAGAATACTCCACAGAGTTG
ATTGTAAATACAGATAGTGAATCGACTATAGACATAATACTATCTGGATCTAC
ACATTCACCAGAAACTAGTTAAGCTTGTCTCCCTATAGTGAGTCGTATTAGA
GCTTGGCGTAATCATGGTCATAGCTGTTTCCTGTGTGAAATTGTTATCCGCT
CACAATTCCACACAACATACGAGCCGGAAGCATAAAGTGTAAAGCCTGGGG
TGCCTAATGAGTGAGCTAACTCACATTAATTGCGTTGCGCTCACTGCCCGCT
TTCGAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCG
TTGCTGGCGTTTTTTCGATAGGCTCCGCCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATC
CGGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACA
GTTACCAATGCTTAATCAGTGAGGCACCTATCTCAGCGATCTGTCTATTTCG
TTCATCCATAGTTGCCTGACTCCCCGTCGTGTAGATAACTACGATACGGGAG
GGCTTACCATCTGGCCCCAGTGCTGCAATGATACCGCGAGACCCACGCTCA
CCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTT
GGCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCA
ATACGGGATAATACCGCGCCACATAGCAGAACTTTAAAAGTGCTCATCATTG
GAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTAC
```

FIG. 15E

TTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTT
CAATATTATTGAAGCATTTATCAGGGTTATTGTCTCATGAGCGGATACATATT
TGAATGTATTTAGAAAAATAAACAAATAGGGGTTCCGCGCACATTTCCCCGA
AAAGTGCCACCTGACGTCTAAGAAACCATTATTATCATGACATTAACCTATAA
AAATAGGCGTATCACGAGGCCCTTTCGTCTCGCGCGTTTCGGTGATGACGG
TGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACT
GAGAGTGCACCATATGCGGTGTGAAATACCGCACAGATGCGTAAGGAGAAA
ATACCGCATCAGGCGCCATTCGCCATTCAGGCTGCGCAACTGTTGGGAAGG
GCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGAC
GTTGTAAAACGACGGCCAGTGAATTGGATTTAGGTGACACTATA

New Psyn II Promoter which controls ADA envelope expression:

TAAAAAATGAAAAAATATTCTAATTTATAGGACGGTTTTGATTTTCTTTTTTTC
TATGCTATAAATAATAAATA

ADA envelope truncated:

ATGAAAGTGAAGGGGATCAGGAAGAATTATCAGCACTTGTGGAAATGGGGC
ATCATGCTCCTTGGGATGTTGATGATCTGTAGTGCTGTAGAAAATTTGTGGG
TCACAGTTTATTATGGGGTACCTGTGTGGAAAGAAGCAACCACCACTCTATT
TTGTGCATCAGATGCTAAAGCATATGATACAGAGGTACATAATGTTTGGGCC
ACACATGCCTGTGTACCCACAGACCCCAACCCACAAGAAGTAGTATTGGAA
AATGTGACAGAAAATTTTAACATGTGGAAAAATAACATGGTAGAACAGATGC
ATGAGGATATAATCAGTTTATGGGATCAAAGCCTAAAGCCATGTGTAAAATT
AACCCCACTCTGTGTTACTTTAAATTGCACTGATTTGAGGAATGTTACTAATA
TCAATAATAGTAGTGAGGGAATGAGAGGAGAAATAAAAAACTGCTCTTTCAA
TATCACCACAAGCATAAGAGATAAGGTGAAGAAAGACTATGCACTTTTCTAT
AGACTTGATGTAGTACCAATAGATAATGATAATACTAGCTATAGGTTGATAAA
TTGTAATACCTCAACCATTACACAGGCCTGTCCAAAGGTATCCTTTGAGCCA
ATTCCCATACATTATTGTACCCCGGCTGGTTTTGCGATTCTAAAGTGTAAAG
ACAAGAAGTTCAATGGAACAGGGCCATGTAAAAATGTCAGCACAGTACAAT
GTACACATGGAATTAGGCCAGTAGTGTCAACTCAACTGCTGTTAAATGGCAG
TCTAGCAGAAGAAGAGGTAGTAATTAGATCTAGTAATTTCACAGACAATGCA
AAAAACATAATAGTACAGTTGAAAGAATCTGTAGAAATTAATTGTACAAGACC
CAACAACAATACAAGGAAAAGTATACATATAGGACCAGGAAGAGCATTTTTAT
ACAACAGGAGAAATAATAGGAGATATAAGACAAGCACATTGCAACATTAGTA
GAACAAAATGGAATAACACTTTAAATCAAATAGCTACAAAATTAAAAGAACAA
TTTGGGAATAATAAAACAATAGTCTTTAATCAATCCTCAGGAGGGGACCCAG
AAATTGTAATGCACAGTTTTAATTGTGGAGGGGAATTCTTCTACTGTAATTCA
ACACAACTGTTTAATAGTACTTGGAATTTTAATGGTACTTGGAATTTAACACA

FIG. 15F

ATCGAATGGTACTGAAGGAAATGACACTATCACACTCCCATGTAGAATAAAA
CAAATTATAAATATGTGGCAGGAAGTAGGAAAAGCAATGTATGCCCCTCCCA
TCAGAGGACAAATTAGATGCTCATCAAATATTACAGGGCTAATATTAACAAG
AGATGGTGGAACTAACAGTAGTGGGTCCGAGATCTTCAGACCTGGGGGAG
GAGATATGAGGGACAATTGGAGAAGTGAATTATATAAATATAAAGTAGTAAA
AATTGAACCATTAGGAGTAGCACCCACCAAGGCAAAAGAAGAGTGGTGCA
GAGAGAAAAAAGAGCAGTGGGAACGATAGGAGCTATGTTCCTTGGGTTCTT
GGGAGCAGCAGGAAGCACTATGGGCGCAGCGTCAATAACGCTGACGGTAC
AGGCCAGACTATTATTGTCTGGTATAGTGCAACAGCAGAACAATTTGCTGAG
GGCTATTGAGGCGCAACAGCATCTGTTGCAACTCACAGTCTGGGGCATCAA
GCAGCTCCAGGCAAGAGTCCTGGCTGTGGAAAGATACCTAAGGGATCAACA
GCTCCTAGGGATTTGGGGTTGCTCTGGAAAACTCATCTGCACCACTGCTGT
GCCTTGGAATGCTAGTTGGAGTAATAAAACTCTGGATATGATTTGGGATAAC
ATGACCTGGATGGAGTGGGAAAGAGAAATCGAAAATTACACAGGCTTAATAT
ACACCTTAATTGAGGAATCGCAGAACCAACAAGAAAAGAATGAACAAGACTT
ATTAGCATTAGATAAGTGGGCAAGTTTGTGGAATTGGTTTGACATATCAAATT
GGCTGTGGTATGTAAAAATCTTCATAATGATAGTAGGAGGCTTGATAGGTTT
AAGAATAGTTTTTACTGTACTTTCTATAGTAAATAGAGTTAGGCAGGGATACT
CACCATTGTCATTTCAGACCCACCTCCCAGCCCCGAGGGGACCCGACAGG
CCCGAAGGAATCGAAGAAGAAGGTGGAGACAGAGAC

PmH5 promoter (which controls HXB2 gag pol expression):

AAAAATTGAAAATAAATACAAAGGTTCTTGAGGGTTGTGTTAAATTGAAAGC
GAGAAATAATCATAAATA

HXB2 gag pol (with safety mutations, Δ integrase):

ATGGGTGCGAGAGCGTCAGTATTAAGCGGGGGAGAATTAGATCGATGGGA
AAAAATTCGGTTAAGGCCAGGGGGAAAGAAAAAATATAAATTAAAACATATA
GTATGGGCAAGCAGGGAGCTAGAACGATTCGCAGTTAATCCTGGCCTGTTA
GAAACATCAGAAGGCTGTAGACAAATACTGGGACAGCTACAACCATCCCTT
CAGACAGGATCAGAAGAACTTAGATCATTATATAATACAGTAGCAACCCTCT
ATTGTGTGCATCAAAGGATAGAGATAAAAGACACCAAGGAAGCTTTAGACAA
GATAGAGGAAGAGCAAAACAAAAGTAAGAAAAAGCACAGCAAGCAGCAGC
TGACACAGGACACAGCAATCAGGTCAGCCAAAATTACCCTATAGTGCAGAA
CATCCAGGGGCAAATGGTACATCAGGCCATATCACCTAGAACTTTAAATGCA
TGGGTAAAAGTAGTAGAAGAGAAGGCTTTCAGCCCAGAAGTGATACCCATG
TTTTCAGCATTATCAGAAGGAGCCACCCCACAAGATTTAAACACCATGCTAA
ACACAGTGGGGGGACATCAAGCAGCCATGCAAATGTTAAAAGAGACCATCA
ATGAGGAAGCTGCAGAATGGGATAGAGTGCATCCAGTGCATGCAGGGCCT
ATTGCACCAGGCCAGATGAGAGAACCAAGGGGAAGTGACATAGCAGGAAC
TACTAGTACCCTTCAGGAACAAATAGGATGGATGACAAATAATCCACCTATC
CCAGTAGGAGAAATTTATAAAAGATGGATAATCCTGGGATTAAATAAAATAG
TAAGAATGTATAGCCCTACCAGCATTCTGGACATAAGACAAGGACCAAAAGA
ACCCTTTAGAGACTATGTAGACCGGTTCTATAAAACTCTAAGAGCCGAGCAA

*FIG. 15G*

```
GCTTCACAGGAGGTAAAAAATTGGATGACAGAAACCTTGTTGGTCCAAAATG
CGAACCCAGATTGTAAGACTATTTTAAAAGCATTGGGACCAGCGGCTACACT
AGAAGAAATGATGACAGCATGTCAGGGAGTAGGAGGACCCGGCCATAAGG
CAAGAGTTTTGGCTGAAGCAATGAGCCAAGTAACAAATTCAGCTACCATAAT
GATGCAGAGAGGCAATTTTAGGAACCAAAGAAAGATTGTTAAGTGTTTCAAT
TGTGGCAAAGAAGGGCACACAGCCAGAAATTGCAGGGCCCCTAGGAAAAA
GGGCTGTTGGAAATGTGGAAAGGAAGGACACCAAATGAAAGATTGTACTGA
GAGACAGGCTAATTTTTTAGGGAAGATCTGGCCTTCCTACAAGGGAAGGCC
AGGGAATTTTCTTCAGAGCAGACCAGAGCCAACAGCCCCACCAGAAGAGAG
CTTCAGGTCTGGGGTAGAGACAACAACTCCCCCTCAGAAGCAGGAGCCGAT
AGACAAGGAACTGTATCCTTTAACTTCCCTCAGATCACTCTTTGGCAACGAC
CCCTCGTCACAATAAAGATAGGGGGGCAACTAAAGGAAGCTCTATTAGATA
CAGGAGCAGATGATACAGTATTAGAAGAAATGAGTTTGCCAGGAAGATGGA
AACCAAAAATGATAGGGGGAATTGGAGGTTTTATCAAAGTAAGACAGTATGA
TCAGATACTCATAGAAATCTGTGGACATAAAGCTATAGGTACAGTATTAGTA
GGACCTACACCTGTCAACATAATTGGAAGAAATCTGTTGACTCAGATTGGTT
GCACTTTAAATTTTCCCATTAGCCCTATTGAGACTGTACCAGTAAAATTAAAG
CCAGGAATGGATGGCCCAAAAGTTAAACAATGGCCATTGACAGAAGAAAAA
ATAAAAGCATTAGTAGAAATTTGTACAGAAATGGAAAAGGAAGGGAAATTT
CAAAAATTGGGCCTGAGAATCCATACAATACTCCAGTATTTGCCATAAAGAA
AAAAGACAGTACTAAATGGAGGAAATTAGTAGATTTCAGAGAACTTAATAAG
AGAACTCAAGACTTCTGGGAAGTTCAATTAGGAATACCACATCCCGCAGGG
TTAAAAAAGAAAAAATCAGTAACAGTACTGGATGTGGGTGATGCATATTTTTC
AGTTCCCTTAGATGAAGACTTCAGGAAGTATACTGCATTTACCATACCTAGT
ATAAACAATGAGACACCAGGGATTAGATATCAGTACAATGTGCTTCCACAGG
GATGGAAAGGATCACCAGCAATATTCCAAAGTAGCATGACAAAAATCTTAGA
GCCTTTTAAAAAACAAAATCCAGACATAGTTATCTATCAATACATGAACGATT
TGTATGTAGGATCTGACTTAGAAATAGGGCAGCATAGAACAAAAATAGAGGA
GCTGAGACAACATCTGTTGAGGTGGGGACTTACCACACCAGACAAAAAACA
TCAGAAAGAACCTCCATTCCTTTGGATGGGTTATGAACTCCATCCTGATAAA
TGGACAGTACAGCCTATAGTGCTGCCAGAAAAAGACAGCTGGACTGTCAAT
GACATACAGAAGTTAGTGGGGAAATTGAATACCGCAAGTCAGATTTACCCA
GGGATTAAAGTAAGGCAATTATGTAAACTCCTTAGAGGAACCAAAGCACTAA
CAGAAGTAATACCACTAACAGAAGAAGCAGAGCTAGAACTGGCAGAAAACA
GAGAGATTCTAAAAGAACCAGTACATGGAGTGTATTATGACCCATCAAAAGA
CTTAATAGCAGAAATACAGAAGCAGGGGCAAGGCCAATGGACATATCAAAT
TTATCAAGAGCCATTTAAAAATCTGAAAACAGGAAAATATGCAAGAATGAGG
GGTGCCCACACTAATGATGTAAAACAATTAACAGAGGCAGTGCAAAAAATAA
CCACAGAAAGCATAGTAATATGGGGAAAGACTCCTAAATTTAAACTACCCAT
ACAAAAGGAAACATGGGAAACATGGTGGACAGAGTATTGGCAAGCCACCTG
GATTCCTGAGTGGGAGTTTGTTAATACCCCTCCTTTAGTGAAATTATGGTAC
CAGTTAGAGAAAGAACCCATAGTAGGAGCAGAAACCTTCTATGTAGATGGG
GCAGCTAACAGGGAGACTAAATTAGGAAAAGCAGGATATGTTACTAACAAA
GGAAGACAAAAGGTTGTCCCCCTAACTAACACAACAAATCAGAAAACTCAGT
TACAAGCAATTTATCTAGCTTTGCAGGATTCAGGATTAGAAGTAAACATAGTA
ACAGACTCACAATATGCATTAGGAATCATTCAAGCACAACCAGATAAAAGTG
```

FIG. 15H

AATCAGAGTTAGTCAATCAAATAATAGAGCAGTTAATAAAAAAGGAAAAGGT
CTATCTGGCATGGGTACCAGCACACAAAGGAATTGGAGGAAATGAACAAGT
AGATAAATTAGTCAGTGCTGGAATCAGGAAAATACTATTTTTAGATGGAATA
GATAAGGCCCAAGATGAACATTAG

*FIG. 15I*

Sequence of new Psyn II promoter:

Early part of promoter

Critical region         Early start site

TAAAAAATGAAAAAATATTCTAATTTATAGGACGGT

Late part of promoter

TTTGATTTTCTTTTTTCTATGCTATAAATAATAAATA

FIG. 18

```
                        SEQUENCE LISTING

<160> NUMBER OF SEQ ID NOS: 13

<210> SEQ ID NO 1
<211> LENGTH: 12225
<212> TYPE: DNA
<213> ORGANISM: Artificial Sequence
<220> FEATURE:
<223> OTHER INFORMATION: Plasmid pLW-48

<400> SEQUENCE: 1
gaattcgttg gtggtcgcca tggatggtgt tattgtatac tgtctaaacg cgttagtaaa      60
acatggcgag gaaataaatc atataaaaaa tgatttcatg attaaaccat gttgtgaaaa     120
agtcaagaac gttcacattg gcggacaatc taaaaacaat acagtgattg cagatttgcc     180
atatatggat aatgcggtat ccgatgtatg caattcactg tataaaaaga atgtatcaag     240
aatatccaga tttgctaatt tgataaagat agatgacgat gacaagactc ctactggtgt     300
atataattat tttaaaccta agatgccat tcctgttatt atatccatag aaaggatag       360 agatgtttgt gaactattaa tctcatctga taaagcgtgt gcgtgtatag agttaaattc     420
atataaagta gccattcttc ccatggatgt ttccttttt accaaggaa atgcatcatt       480 gattattctc ctgtttgatt tctctatcga tgcggcacct ctcttaagaa gtgtaaccga     540
```

```
taataatgtt attatatcta gacaccagcg tctacatgac gagcttccga gttccaattg    600
gttcaagttt tacataagta taaagtccga ctattgttct atattatata tggttgttga    660
tggatctgtg atgcatgcaa tagctgataa tagaacttac gcaaatatta gcaaaaatat    720
attagacaat actacaatta acgatgagtg tagatgctgt tattttgaac cacagattag    780
gattcttgat agagatgaga tgctcaatgg atcatcgtgt gatatgaaca gacattgtat    840
tatgatgaat ttacctgatg taggcgaatt tggatctagt atgttgggga aatatgaacc    900
tgacatgatt aagattgctc tttcggtggc tgggtaccag gcgcgccttt cattttgttt    960
ttttctatgc tataaatggt acgtcctgta gaaaccccaa cccgtgaaat caaaaaactc    1020
gacggcctgt gggcattcag tctggatcgc gaaaactgtg gaattgatca gcgttggtgg    1080
gaaagcgcgt tacaagaaag ccgggcaatt gctgtgccag gcagttttaa cgatcagttc    1140
gccgatgcag atattcgtaa ttatgcgggc aacgtctggt atcagcgcga agtctttata    1200
ccgaaaggtt gggcaggcca gcgtatcgtc ctgcgtttcg atgcggtcac tcattacggc    1260
aaagtgtggg tcaataatca ggaagtgatg gagcatcagg cggctatac gccatttgaa    1320
gccgatgtca cgccgtatgt tattgccggg aaaagtgtac gtatcaccgt ttgtgtgaac    1380
aacgaactga actggcagac tatcccgccg ggaatggtga ttaccgacga aaacggcaag    1440
aaaaagcagt cttacttcca tgatttcttt aactatgccg gaatccatcg cagcgtaatg    1500
ctctacacca cgccgaacac ctgggtggac gatatcaccg tggtgacgca tgtcgcgcaa    1560
gactgtaacc acgcgtctgt tgactggcag gtggtggcca atggtgatgt cagcgttgaa    1620
ctgcgtgatg cggatcaaca ggtggttgca actggacaag cactagcgg acttttgcaa    1680
gtggtgaatc cgcacctctg caaccgggt gaaggttatc tctatgaact gtgcgtcaca    1740
gccaaaagcc agacagagtg tgatatctac ccgcttcgcg tcggcatccg gtcagtggca    1800
gtgaagggcg aacagttcct gattaaccac aaaccgttct actttactgg ctttggtcgt    1860
catgaagatg cggacttgcg tggcaaagga ttcgataacg tgctgatggt gcacgaccac    1920
gcattaatgg actggattgg ggccaactcc taccgtacct cgcattaccc ttacgctgaa    1980
gagatgctcg actgggcaga tgaacatggc atcgtggtga ttgatgaaac tgctgctgtc    2040
ggctttaacc tctctttagg cattggtttc gaagcgggca acaagccgaa agaactgtac    2100
agcgaagagg cagtcaacgg ggaaactcag caagcgcact acaggcgat taaagagctg    2160
atagcgcgtg acaaaaacca cccaagcgtg gtgatgtgga gtattgccaa cgaaccggat    2220
acccgtccgc aaggtgcacg ggaatatttc gcgccactgg cggaagcaac gcgtaaactc    2280
gacccgacgc gtccgatcac ctgcgtcaat gtaatgttct gcgacgctca caccgatacc    2340
atcagcgatc tctttgatgt gctgtgcctg aaccgttatt acggatggta tgtccaaagc    2400
ggcgatttgg aaacggcaga aaggtactg gaaaaagaac ttctggcctg gcaggagaaa    2460
ctgcatcagc cgattatcat caccgaatac ggcgtggata cgttagccgg gctgcactca    2520
atgtacaccg acatgtggag tgaagagtat cagtgtgcat ggctggatat gtatcaccgc    2580
gtctttgatc gcgtcagcgc cgtcgtcggt gaacaggtat ggaatttcgc cgattttgcg    2640
acctcgcaag gcatattgcg cgttggcggt aacaagaaag gatcttcac tcgcgaccgc    2700
aaaccgaagt cggcggcttt tctgctgcaa aaacgctgga ctggcatgaa cttcggtgaa    2760
aaaccgcagc agggaggcaa acaatgagag ctcggttgtt gatggatctg tgatgcatgc    2820
aatagctgat aatagaactt acgcaaatat tagcaaaaat atattagaca atactacaat    2880
taacgatgag tgtagatgct gttattttga accacagatt aggattcttg atagagatga    2940
```

```
gatgctcaat ggatcatcgt gtgatatgaa cagacattgt attatgatga atttacctga    3000
tgtaggcgaa tttggatcta gtatgttggg gaaatatgaa cctgacatga ttaagattgc    3060
tctttcggtg gctggcggcc cgctcgagta aaaatgaaa aaatattcta atttatagga     3120
cggttttgat tttctttttt tctatgctat aaataataaa tagcggccgc accatgaaag    3180 tgaagggat caggaagaat tatcagcact tgtggaaatg gggcatcatg ctccttggga     3240
tgttgatgat ctgtagtgct gtagaaaatt tgtgggtcac agtttattat ggggtacctg    3300
tgtggaaaga agcaaccacc actctatttt gtgcatcaga tgctaaagca tatgatacag    3360
aggtacataa tgtttgggcc acacatgcct gtgtacccac agaccccaac ccacaagaag    3420
tagtattgga aaatgtgaca gaaaatttta acatgtggaa aaataacatg gtagaacaga    3480
tgcatgagga tataatcagt ttatgggatc aaagcctaaa gccatgtgta aaattaaccc    3540
cactctgtgt tactttaaat tgcactgatt tgaggaatgt tactaatatc aataatagta    3600
gtgagggaat gagaggagaa ataaaaaact gctctttcaa tatcaccaca agcataagag    3660
ataaggtgaa gaaagactat gcactttctt atagacttga tgtagtacca atagataatg    3720
ataatactag ctataggttg ataaattgta atacctcaac cattacacag gcctgtccaa    3780
aggtatcctt tgagccaatt cccatacatt attgtacccc ggctggtttt gcgattctaa    3840
agtgtaaaga caagaagttc aatggaacag ggccatgtaa aaatgtcagc acagtacaat    3900
gtacacatgg aattaggcca gtagtgtcaa ctcaactgct gttaaatggc agtctagcag    3960
aagaagaggt agtaattaga tctagtaatt tcacagacaa tgcaaaaaac ataatagtac    4020
agttgaaaga atctgtagaa attaattgta caagacccaa caacaataca aggaaaagta    4080
tacatatagg accaggaaga gcattttata caacaggaga ataataggag atataagac      4140 aagcacattg caacattagt agaacaaaat ggaataacac tttaaatcaa atagctacaa    4200
aattaaaaga acaatttggg aataataaaa caatagtctt taatcaatcc tcaggagggg    4260
acccagaaat tgtaatgcac agttttaatt gtggagggga attcttctac tgtaattcaa    4320
cacaactgtt taatagtact tggaattttta atggtacttg gaatttaaca caatcgaatg    4380
gtactgaagg aaatgacact atcacactcc catgtagaat aaaacaaatt ataaatatgt    4440
ggcaggaagt aggaaaagca atgtatgccc ctcccatcag aggacaaatt agatgctcat    4500
caaatattac agggctaata ttaacaagag atggtggaac taacagtagt gggtccgaga    4560
tcttcagacc tgggggagga gatatgaggg acaattggag aagtgaatta tataaatata    4620
aagtagtaaa aattgaacca ttaggagtag caccaccaa ggcaaaaaga agagtggtgc      4680
agagagaaaa aagagcagtg ggaacgatag gagctatgtt ccttgggttc ttgggagcag    4740
caggaagcac tatgggcgca gcgtcaataa cgctgacggt acaggccaga ctattattgt    4800
ctggtatagt gcaacagcag aacaatttgc tgagggctat tgaggcgcaa cagcatctgt    4860
tgcaactcac agtctgggc atcaagcagc tccaggcaag agtcctggct gtggaaagat      4920
acctaaggga tcaacagctc ctagggattt ggggttgctc tggaaaactc atctgcacca    4980
ctgctgtgcc ttggaatgct agttggagta ataaaactct ggatatgatt tgggataaca    5040
tgacctggat ggagtgggaa agagaaatcg aaaattacac aggcttaata tacaccttaa    5100
ttgaggaatc gcagaaccaa caagaaaaga tgaacaaga cttattagca ttagataagt      5160
gggcaagttt gtggaattgg tttgacatat caaattggct gtggtatgta aaatcttca      5220 taatgatagt aggaggcttg ataggtttaa gaatagtttt tactgtactt tctatagtaa    5280
```

-continued

```
atagagttag gcagggatac tcaccattgt catttcagac ccacctccca gccccgaggg    5340
gacccgacag gcccgaagga atcgaagaag aaggtggaga cagagactaa tttttatgcg    5400
gccgctggta cccaacctaa aaattgaaaa taaatacaaa ggttcttgag ggttgtgtta    5460
aattgaaagc gagaaataat cataaataag cccggggatc ctctagagtc gacaccatgg    5520
gtgcgagagc gtcagtatta agcggggag aattagatcg atgggaaaaa attcggttaa    5580
ggccaggggg aaagaaaaaa tataaattaa acatatagt atgggcaagc agggagctag    5640
aacgattcgc agttaatcct ggcctgttag aaacatcaga aggctgtaga caaatactgg    5700
gacagctaca accatccctt cagacaggat cagaagaact tagatcatta tataatacag    5760
tagcaaccct ctattgtgtg catcaaagga tagagataaa agacaccaag gaagctttag    5820
acaagataga ggaagagcaa aacaaaagta agaaaaagc acagcaagca gcagctgaca    5880
caggacacag caatcaggtc agccaaaatt accctatagt gcagaacatc caggggcaaa    5940
tggtacatca ggccatatca cctagaactt taaatgcatg ggtaaaagta gtagaagaga    6000
aggctttcag cccagaagtg atacccatgt tttcagcatt atcagaagga gccaccccac    6060
aagatttaaa caccatgcta aacacagtgg ggggacatca agcagccatg caaatgttaa    6120
aagagaccat caatgaggaa gctgcagaat gggatagagt gcatccagtg catgcagggc    6180
ctattgcacc aggccagatg agagaaccaa ggggaagtga catagcagga actactagta    6240
cccttcagga caaatagga tggatgacaa ataatccacc tatcccagta ggagaaattt    6300
ataaaagatg gataatcctg ggattaaata aaatagtaag aatgtatagc cctaccagca    6360
ttctggacat aagacaagga ccaaaagaac cctttagaga ctatgtagac cggttctata    6420
aaactctaag agccgagcaa gcttcacagg aggtaaaaaa ttggatgaca gaaaccttgt    6480
tggtccaaaa tgcgaaccca gattgtaaga ctattttaaa agcattggga ccagcggcta    6540
cactagaaga aatgatgaca gcatgtcagg gagtaggagg acccggccat aaggcaagag    6600
ttttggctga gcaatgagc caagtaacaa attcagctac cataatgatg cagagaggca    6660
attttaggaa ccaaagaaag attgttaagt gtttcaattg tggcaaagaa gggcacacag    6720
ccagaaattg cagggcccct aggaaaaagg ctgttggaa atgtggaaag gaaggacacc    6780
aaatgaaaga ttgtactgag agacaggcta attttttagg gaagatctgg ccttcctaca    6840
agggaaggcc agggaatttt cttcagagca gaccagagcc aacagcccca ccagaagaga    6900
gcttcaggtc tgggggtagag caacaactc cccctcagaa gcaggagccg atagacaagg    6960
aactgtatcc tttaacttcc ctcagatcac tctttggcaa cgaccctcg tcacaataaa    7020
gatagggggg caactaaagg aagctctatt agatacagga gcagatgata cagtattaga    7080
agaaatgagt ttgccaggaa gatggaaacc aaaaatgata ggggaattg gaggttttat    7140
caaagtaaga cagtatgatc agatactcat agaaatctgt ggacataaag ctataggtac    7200
agtattagta ggacctacac ctgtcaacat aattggaaga atctgttga ctcagattgg    7260
ttgcacttta aattttccca ttagccctat tgagactgta ccagtaaaat taaagccagg    7320
aatggatggc ccaaaagtta acaatggcc attgacagaa gaaaaaataa aagcattagt    7380
agaaatttgt acagaaatgg aaaaggaagg gaaaatttca aaaattgggc ctgagaatcc    7440
atacaatact ccagtatttg ccataaagaa aaaagacagt actaaatgga gaaaattagt    7500
agatttcaga gaacttaata agagaactca agacttctgg gaagttcaat taggaatacc    7560
acatcccgca gggttaaaaa agaaaaaatc agtaacagta ctggatgtgg gtgatgcata    7620
ttttcagtt cccttagatg aagacttcag gaagtatact gcatttacca tacctagtat    7680
```

```
aaacaatgag acaccaggga ttagatatca gtacaatgtg cttccacagg gatggaaagg      7740
atcaccagca atattccaaa gtagcatgac aaaaatctta gagcctttta aaaacaaaa       7800 tccagacata gttatctatc aatacatgaa cgatttgtat gtaggatctg acttagaaat      7860
agggcagcat agaacaaaaa tagaggagct gagacaacat ctgttgaggt ggggacttac      7920
cacaccagac aaaaaacatc agaagaacc tccattcctt tggatgggtt atgaactcca       7980
tcctgataaa tggacagtac agcctatagt gctgccagaa aaagacagct ggactgtcaa      8040
tgacatacag aagttagtgg ggaaattgaa taccgcaagt cagatttacc cagggattaa      8100
agtaaggcaa ttatgtaaac tccttagagg aaccaaagca ctaacagaag taataccact      8160
aacagaagaa gcagagctag aactggcaga aaacagagag attctaaaag aaccagtaca      8220
tggagtgtat tatgacccat caaaagactt aatagcagaa atacagaagc aggggcaagg      8280
ccaatggaca tatcaaattt atcaagagcc atttaaaaat ctgaaaacag gaaaatatgc      8340
aagaatgagg ggtgcccaca ctaatgatgt aaaacaatta acagaggcag tgcaaaaaat      8400
aaccacagaa agcatagtaa tatggggaaa gactcctaaa tttaaactac ccatacaaaa      8460
ggaaacatgg gaaacatggt ggacagagta ttggcaagcc acctggattc ctgagtggga      8520
gtttgttaat acccctcctt tagtgaaatt atggtaccag ttagagaaag aacccatagt      8580
aggagcagaa accttctatg tagatggggc agctaacagg gagactaaat taggaaaagc      8640
aggatatgtt actaacaaag gaagacaaaa ggttgtcccc ctaactaaca caacaaatca      8700
gaaaactcag ttacaagcaa tttatctagc tttgcaggat tcaggattag aagtaaacat      8760
agtaacagac tcacaatatg cattaggaat cattcaagca caaccagata aaagtgaatc      8820
agagttagtc aatcaaataa tagagcagtt aataaaaaag gaaaaggtct atctggcatg      8880
ggtaccagca cacaaaggaa ttggaggaaa tgaacaagta gataaattag tcagtgctgg      8940
aatcaggaaa atactatttt tagatggaat agataaggcc caagatgaac attagttttt      9000
atgtcgacct gcagggaaag ttttataggt agttgataga acaaaataca taattttgta      9060
aaaataaatc acttttttata ctaatatgac acgattacca atacttttgt tactaatatc      9120
attagtatac gctacacctt ttcctcagac atctaaaaaa ataggtgatg atgcaacttt      9180
atcatgtaat cgaaataata caaatgacta cgttgttatg agtgcttggt ataaggagcc      9240
caattccatt attcttttag ctgctaaaag cgacgtcttg tattttgata attataccaa      9300
ggataaaata tcttacgact ctccatacga tgatctagtt acaactatca caattaaatc      9360
attgactgct agagatgccg gtacttatgt atgtgcattc tttatgacat cgcctacaaa      9420
tgacactgat aaagtagatt atgaagaata ctccacagag ttgattgtaa atacagatag      9480
tgaatcgact atagacataa tactatctgg atctacacat tcaccagaaa ctagttaagc      9540
ttgtctccct atagtgagtc gtattagagc ttggcgtaat catggtcata gctgtttcct      9600
gtgtgaaatt gttatccgct cacaattcca cacaacatac gagccggaag cataaagtgt      9660
aaagcctggg gtgcctaatg agtgagctaa ctcacattaa ttgcgttgcg ctcactgccc      9720
gctttcgagt cgggaaacct gtcgtgccag ctgcattaat gaatcggcca acgcgcgggg      9780
agaggcggtt tgcgtattgg gcgctcttcc gcttcctcgc tcactgactc gctgcgctcg      9840
gtcgttcggc tgcggcgagc ggtatcagct cactcaaagg cggtaatacg gttatccaca      9900
gaatcagggg ataacgcagg aaagaacatg tgagcaaaag gccagcaaaa ggccaggaac      9960
cgtaaaaagg ccgcgttgct ggcgtttttc gataggctcc gcccccctga cgagcatcac     10020
```

```
aaaaatcgac gctcaagtca gaggtggcga aacccgacag gactataaag ataccaggcg   10080 tttcccctg  gaagctccct cgtgcgctct cctgttccga ccctgccgct taccggatac   10140
ctgtccgcct ttctcccttc gggaagcgtg gcgctttctc atagctcacg ctgtaggtat   10200
ctcagttcgg tgtaggtcgt tcgctccaag ctgggctgtg tgcacgaacc ccccgttcag   10260
cccgaccgct gcgccttatc cggtaactat cgtcttgagt ccaacccggt aagacacgac   10320
ttatcgccac tggcagcagc cactggtaac aggattagca gagcgaggta tgtaggcggt   10380
gctacagagt tcttgaagtg gtggcctaac tacggctaca ctagaaggac agtatttggt   10440
atctgcgctc tgctgaagcc agttaccttc ggaaaaagag ttggtagctc ttgatccggc   10500
aaacaaacca ccgctggtag cggtggtttt tttgtttgca agcagcagat tacgcgcaga   10560
aaaaaaggat ctcaagaaga tcctttgatc ttttctacgg ggtctgacgc tcagtggaac   10620
gaaaactcac gttaagggat tttggtcatg agattatcaa aaaggatctt cacctagatc   10680
cttttaaatt aaaaatgaag ttttaaatca atctaaagta tatatgagta aacttggtct   10740
gacagttacc aatgcttaat cagtgaggca cctatctcag cgatctgtct atttcgttca   10800
tccatagttg cctgactccc cgtcgtgtag ataactacga tacgggaggg cttaccatct   10860
ggccccagtg ctgcaatgat accgcgagac ccacgctcac cggctccaga tttatcagca   10920
ataaaccagc cagccggaag ggccgagcgc agaagtggtc ctgcaacttt atccgcctcc   10980
atccagtcta ttaattgttg ccgggaagct agagtaagta gttcgccagt taatagtttg   11040
cgcaacgttg ttggcattgc tacaggcatc gtggtgtcac gctcgtcgtt tggtatggct   11100
tcattcagct ccggttccca acgatcaagg cgagttacat gatcccccat gttgtgcaaa   11160
aaagcggtta gctccttcgg tcctccgatc gttgtcagaa gtaagttggc cgcagtgtta   11220
tcactcatgg ttatggcagc actgcataat tctcttactg tcatgccatc cgtaagatgc   11280
ttttctgtga ctggtgagta ctcaaccaag tcattctgag aatagtgtat gcggcgaccg   11340
agttgctctt gcccggcgtc aatacgggat aataccgcgc cacatagcag aactttaaaa   11400
gtgctcatca ttggaaaacg ttcttcgggg cgaaaactct caaggatctt accgctgttg   11460
agatccagtt cgatgtaacc cactcgtgca cccaactgat cttcagcatc ttttactttc   11520
accagcgttt ctgggtgagc aaaaacagga aggcaaaatg ccgcaaaaaa gggaataagg   11580
gcgacacgga aatgttgaat actcatactc ttccttttc  aatattattg aagcatttat   11640
cagggttatt gtctcatgag cggatacata tttgaatgta tttagaaaaa taaacaaata   11700
ggggttccgc gcacatttcc ccgaaaagtg ccacctgacg tctaagaaac cattattatc   11760
atgacattaa cctataaaaa taggcgtatc acgaggccct ttcgtctcgc gcgtttcggt   11820
gatgacggtg aaaacctctg acacatgcag ctcccggaga cggtcacagc ttgtctgtaa   11880
gcggatgccg ggagcagaca agcccgtcag gcgcgtcag  cgggtgttgg cgggtgtcgg   11940
ggctggctta actatgcggc atcagagcag attgtactga gagtgcacca tatgcggtgt   12000
gaaataccgc acagatgcgt aaggagaaaa taccgcatca ggcgccattc gccattcagg   12060
ctgcgcaact gttgggaagg gcgatcggtg cgggcctctt cgctattacg ccagctggcg   12120
aaagggggat gtgctgcaag gcgattaagt tgggtaacgc cagggttttc ccagtcacga   12180
cgttgtaaaa cgacggccag tgaattggat ttaggtgaca ctata              12225
```

<210> SEQ ID NO 2
<211> LENGTH: 74
<212> TYPE: DNA
<213> ORGANISM: Artificial Sequence
<220> FEATURE:
<223> OTHER INFORMATION: Psyn II promoter

<400> SEQUENCE: 2

```
taaaaaatga aaaatatattc taatttatag gacggttttg attttctttt tttctatgct    60
ataaataata aata                                                       74
```

<210> SEQ ID NO 3
<211> LENGTH: 2214
<212> TYPE: DNA
<213> ORGANISM: Artificial Sequence
<220> FEATURE:
<223> OTHER INFORMATION: HIV env gene

<400> SEQUENCE: 3

```
atgaaagtga aggggatcag gaagaattat cagcacttgt ggaaatgggg catcatgctc     60
cttgggatgt tgatgatctg tagtgctgta gaaaatttgt gggtcacagt ttattatggg    120
gtacctgtgt ggaagaagc aaccaccact ctattttgtg catcagatgc taaagcatat    180
gatacagagg tacataatgt ttgggccaca catgcctgtg tacccacaga ccccaaccca    240
caagaagtag tattggaaaa tgtgacagaa aattttaaca tgtggaaaaa taacatggta    300
gaacagatgc atgaggatat aatcagttta tgggatcaaa gcctaaagcc atgtgtaaaa    360
ttaaccccca tctgtgttac tttaaattgc actgatttga ggaatgttac taatatcaat    420
aatagtagtg agggaatgag aggagaaata aaaaactgct ctttcaatat caccacaagc    480
ataagagata aggtgaagaa agactatgca cttttctata gacttgatgt agtaccaata    540
gataatgata atactagcta taggttgata aattgtaata cctcaaccat tacacaggcc    600
tgtccaaagg tatcctttga gccaattccc atacattatt gtaccccggc tggttttgcg    660
attctaaagt gtaaagacaa gaagttcaat ggaacagggc catgtaaaaa tgtcagcaca    720
gtacaatgta cacatggaat taggccagta gtgtcaactc aactgctgtt aaatggcagt    780
ctagcagaag aagaggtagt aattagatct agtaatttca cagacaatgc aaaaaacata    840
atagtacagt tgaaagaatc tgtagaaatt aattgtacaa gacccaacaa caatacaagg    900
aaaagtatac atataggacc aggaagagca ttttatacaa caggagaaat aataggagat    960
ataagacaag cacattgcaa cattagtaga acaaaatgga ataacacttt aaatcaaata   1020
gctacaaaat taaagaaaca atttgggaat aataaaacaa tagtctttaa tcaatcctca   1080 ggagggacc cagaaattgt aatgcacagt tttaattgtg gaggggaatt cttctactgt   1140
aattcaacac aactgtttaa tagtacttgg aatttaatg gtacttggaa tttaacacaa   1200
tcgaatggta ctgaaggaaa tgacactatc acactcccat gtagaataaa acaaattata   1260
aatatgtggc aggaagtagg aaaagcaatg tatgcccctc ccatcagagg acaaattaga   1320
tgctcatcaa atattacagg gctaatatta acaagagatg gtggaactaa cagtagtggg   1380
tccgagatct tcagacctgg gggaggagat atgagggaca attggagaag tgaattatat   1440
aaatataaag tagtaaaaat tgaaccatta ggagtagcac ccaccaaggc aaaaagaaga   1500
gtggtgcaga gagaaaaaag agcagtggga acgataggag ctatgttcct tgggttcttg   1560
ggagcagcag gaagcactat gggcgcagcg tcaataacgc tgacggtaca ggccagacta   1620
ttattgtctg gtatagtgca acagcagaac aatttgctga gggctattga ggcgcaacag   1680
catctgttgc aactcacagt ctggggcatc aagcagctcc aggcaagagt cctggctgtg   1740
gaaagatacc taagggatca acagctccta gggatttggg gttgctctgg aaaactcatc   1800
```

| | |
|---|---|
| tgcaccactg ctgtgccttg gaatgctagt tggagtaata aaactctgga tatgatttgg | 1860 |
| gataacatga cctggatgga gtgggaaaga gaaatcgaaa attacacagg cttaatatac | 1920 |
| accttaattg aggaatcgca gaaccaacaa gaaaagaatg aacaagactt attagcatta | 1980 |
| gataagtggg caagtttgtg gaattggttt gacatatcaa attggctgtg gtatgtaaaa | 2040 |
| atcttcataa tgatagtagg aggcttgata ggtttaagaa tagttttac tgtactttct | 2100 |
| atagtaaata gagttaggca gggatactca ccattgtcat ttcagaccca cctcccagcc | 2160 |
| ccgaggggac ccgacaggcc cgaaggaatc gaagaagaag gtggagacag agac | 2214 |

<210> SEQ ID NO 4
<211> LENGTH: 70
<212> TYPE: DNA
<213> ORGANISM: Artificial Sequence
<220> FEATURE:
<223> OTHER INFORMATION: PmH5 promoter

<400> SEQUENCE: 4

| | |
|---|---|
| aaaaattgaa ataaatacaa aaggttcttg agggttgtgt taaattgaaa gcgagaaata | 60 |
| atcataaata | 70 |

<210> SEQ ID NO 5
<211> LENGTH: 3479
<212> TYPE: DNA
<213> ORGANISM: Artificial Sequence
<220> FEATURE:
<223> OTHER INFORMATION: HIV genes

<400> SEQUENCE: 5

| | |
|---|---|
| atgggtgcga gagcgtcagt attaagcggg ggagaattag atcgatggga aaaaattcgg | 60 |
| ttaaggccag ggggaaagaa aaaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa aagcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaaa gaacccttta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt cagggagtag gaggacccgg ccataaggca | 1080 |
| agagttttgg ctgaagcaat gagccaagta acaaattcag ctaccataat gatgcagaga | 1140 |
| ggcaattttta ggaaccaaag aaagattgtt aagtgtttca attgtggcaa agaagggcac | 1200 |
| acagccagaa attgcagggc ccctaggaaa aagggctgtt ggaaatgtgg aaaggaagga | 1260 |

```
caccaaatga aagattgtac tgagagacag gctaattttt tagggaagat ctggccttcc    1320
tacaagggaa ggccagggaa ttttcttcag agcagaccag agccaacagc cccaccagaa    1380
gagagcttca ggtctggggt agagacaaca actcccccctc agaagcagga gccgatagac   1440
aaggaactgt atcctttaac ttccctcaga tcactctttg caacgaccc ctcgtcacaa     1500 taaagatagg ggggcaacta aaggaagctc tattagatac aggagcagat gatacagtat    1560
tagaagaaat gagtttgcca ggaagatgga aaccaaaaat gatagggga attggaggtt     1620 ttatcaaagt aagacagtat gatcagatac tcatagaaat ctgtggacat aaagctatag    1680
gtacagtatt agtaggacct acacctgtca acataattgg aagaaatctg ttgactcaga    1740
ttggttgcac tttaaatttt cccattagcc ctattgagac tgtaccagta aaattaaagc    1800
caggaatgga tggcccaaaa gttaaacaat ggccattgac agaagaaaaa ataaaagcat    1860
tagtagaaat ttgtacagaa atggaaaagg aagggaaaat ttcaaaaatt gggcctgaga    1920
atccatacaa tactccagta tttgccataa agaaaaaaga cagtactaaa tggaggaaat    1980
tagtagattt cagagaactt aataagagaa ctcaagactt ctgggaagtt caattaggaa    2040
taccacatcc cgcagggtta aaaagaaaa atcagtaac agtactggat gtgggtgatg      2100
catatttttc agttccctta gatgaagact tcaggaagta tactgcattt accataccta    2160
gtataaacaa tgagacacca gggattagat atcagtacaa tgtgcttcca cagggatgga   2220
aaggatcacc agcaatattc caaagtagca tgacaaaaat cttagagcct tttaaaaaac    2280
aaaatccaga catagttatc tatcaataca tgaacgattt gtatgtagga tctgacttag   2340
aaatagggca gcatagaaca aaaatagagg agctgagaca catctgttg aggtggggac    2400 ttaccacacc agacaaaaaa catcagaaag aacctccatt cctttggatg ggttatgaac    2460
tccatcctga taaatggaca gtacagccta tagtgctgcc agaaaaagac agctggactg    2520
tcaatgacat acagaagtta gtggggaaat tgaataccgc aagtcagatt tacccaggga    2580
ttaaagtaag gcaattatgt aaactcctta gaggaaccaa agcactaaca gaagtaatac    2640
cactaacaga agaagcagag ctagaactgg cagaaaacag agagattcta aaagaaccag    2700
tacatggagt gtattatgac ccatcaaaag acttaatagc agaaatacag aagcaggggc    2760
aaggccaatg gacatatcaa atttatcaag agccatttaa aaatctgaaa acaggaaaat    2820
atgcaagaat gagggtgcc cacactaatg atgtaaaaca attaacagag gcagtgcaaa     2880
aaataaccac agaaagcata gtaatatggg gaaagactcc taaatttaaa ctacccatac    2940
aaaaggaaac atgggaaaca tggtggacag agtattggca agccacctgg attcctgagt    3000
gggagtttgt taatacccct cctttagtga aattatggta ccagttagag aaagaaccca    3060
tagtaggagc agaaaccttc tatgtagatg ggcagctaa cagggagact aaattaggaa     3120
aagcaggata tgttactaac aaaggaagac aaaaggttgt ccccctaact aacacaacaa    3180
atcagaaaac tcagttacaa gcaatttatc tagctttgca ggattcagga ttagaagtaa    3240
acatagtaac agactcacaa tatgcattag gaatcattca agcacaacca gataaaagtg    3300
aatcagagtt agtcaatcaa ataatagagc agttaataaa aaaggaaaag gtctatctgg    3360
catgggtacc agcacacaaa ggaattggag gaaatgaaca agtagataaa ttagtcagtg    3420
ctggaatcag gaaaatacta ttttagatg gaatagataa ggcccaagat gaacattag    3479
```

<210> SEQ ID NO 6
<211> LENGTH: 9
<212> TYPE: PRT

<213> ORGANISM: Simian Immunodeficiency virus

<400> SEQUENCE: 6

Cys Thr Pro Tyr Asp Ile Asn Gln Met
1 5

<210> SEQ ID NO 7
<211> LENGTH: 8
<212> TYPE: PRT
<213> ORGANISM: Gallus gallus

<400> SEQUENCE: 7

Ser Ile Ile Asn Phe Glu Lys Leu
1 5

<210> SEQ ID NO 8
<211> LENGTH: 20
<212> TYPE: DNA
<213> ORGANISM: Artificial Sequence
<220> FEATURE:
<223> OTHER INFORMATION: probe sequence

<400> SEQUENCE: 8
ctgtctgcgt catttggtgc 20

<210> SEQ ID NO 9
<211> LENGTH: 4
<212> TYPE: PRT
<213> ORGANISM: Human immunodeficiency Virus
<220> FEATURE:
<221> NAME/KEY: VARIANT
<222> LOCATION: 2,3
<223> OTHER INFORMATION: Xaa = Any Amino Acid

<400> SEQUENCE: 9

Tyr Xaa Xaa Leu
1

<210> SEQ ID NO 10
<211> LENGTH: 93
<212> TYPE: DNA
<213> ORGANISM: Artificial Sequence
<220> FEATURE:
<223> OTHER INFORMATION: m7.5 promote

<400> SEQUENCE: 10
cgctttttat agtaagtttt tcacccataa ataataaata caataattaa tttctcgtaa 60
aaattgaaaa actattctaa tttattgcac ggt 93

<210> SEQ ID NO 11
<211> LENGTH: 74
<212> TYPE: DNA
<213> ORGANISM: Artificial Sequence
<220> FEATURE:
<223> OTHER INFORMATION: Psyn III promoter

<400> SEQUENCE: 11
taaaaattga aaaaatattc taatttatag gacggttttg attttctttt tttctatact 60
ataaataata aata 74

<210> SEQ ID NO 12
<211> LENGTH: 74
<212> TYPE: DNA
<213> ORGANISM: Artificial Sequence
<220> FEATURE:

-continued

```
<223> OTHER INFORMATION: Psyn IV promoter

<400> SEQUENCE: 12
taaaaattga aaaactattc taatttatag gacggttttg attttctttt tttctatact     60
ataaataata aata                                                       74

<210> SEQ ID NO 13
<211> LENGTH: 75
<212> TYPE: DNA
<213> ORGANISM: Artificial Sequence
<220> FEATURE:
<223> OTHER INFORMATION: Psyn V promote

<400> SEQUENCE: 13
aaaaaatgat aaagtaggtt cagttttatt gctggtttaa aatcacgctt tcgagtaaaa     60
actacgaata taaat                                                      75
```

MVA EXPRESSING MODIFIED HIV ENVELOPE, GAG, AND POL GENES

RELATED APPLICATIONS

This application is a continuation of U.S. application Ser. No. 12/018,150 filed Jan. 22, 2008, now U.S. Pat. No. 7,867,982 which is a continuation of U.S. application Ser. No. 10/646,628, filed Aug. 22, 2003 now abandoned which is a continuation and claims the benefit of priority of International Application No. PCT/US02/06713 filed Mar. 1, 2002, designating the United States of America and published in English, which claims the benefit of priority of U.S. Provisional Application No. 60/274,434 filed Mar. 8, 2001, all of which are hereby expressly incorporated by reference in their entireties.

FIELD OF THE INVENTION

The invention provides modified vaccinia Ankara (MVA), a replication-deficient strain of vaccinia virus, expressing human immunodeficiency virus (HIV) env, gag, and pol genes.

BACKGROUND OF THE INVENTION

Cellular immunity plays an important role in the control of immunodeficiency virus infections (P. J. Goulder et al. 1999 *AIDS* 13:S 121). Recently, a DNA vaccine designed to enhance cellular immunity by cytokine augmentation successfully-contained a highly virulent immunodeficiency virus challenge (D. H. Barouch et al. 2000 *Science* 290:486). Another promising approach to raising cellular immunity is DNA priming followed by recombinant poxvirus boosters (H. L. Robinson et al. 2000 *AIDS Rev* 2:105). This heterologous prime/boost regimen induces 10- to 100-fold higher frequencies of T cells than priming and boosting with DNA or recombinant poxvirus vaccines alone. Previously, investigators showed that boosting a DNA-primed response with a poxvirus was superior to boosting with DNA or protein for the control of a non-pathogenic immunodeficiency virus (H. L. Robinson et al. 1999 *Nat Med* 5:526). There is a need for the control of a pathogenic immunodeficiency virus.

SUMMARY OF THE INVENTION

Here we report that DNA priming followed by a recombinant modified vaccinia Ankara (rMVA) booster has controlled a highly pathogenic immunodeficiency virus challenge in a rhesus macaque model. Both the DNA and rMVA components of the vaccine expressed multiple immunodeficiency virus proteins. Two DNA inoculations at 0 and 8 weeks and a single rMVA booster at 24 weeks effectively controlled an intrarectal challenge administered seven months after the booster. These findings are envisioned as indicating that a relatively simple multiprotein DNA/MVA vaccine can help to control the acquired immune deficiency syndrome (AIDS) epidemic. We also report that inoculations of rMVA induce good immune responses even without DNA priming.

BRIEF DESCRIPTION OF THE DRAWINGS

FIG. 3. Tropic and biologic properties of HIV-1 isolates.

FIG. 14. Sequence of plasmid transfer vector pLW-48.

FIG. 15. Sequences of plasmid transfer vector pLW-48, Psy II promoter (which controls ADA envelope expression), ADA envelope truncated, PmH5 promoter (which controls HXB2 gag pol expression), and HXB2 gag pol (with safety mutations, Δ integrase).

FIG. 18. Sequence of new Psyn II promoter.

DETAILED DESCRIPTION OF THE PREFERRED EMBODIMENT

Recombinant MVA Virus

Vaccinia virus, a member of the genus Orthopoxvirus in the family of Poxyiridae, was used as live vaccine to immunize against the human smallpox disease. Successful worldwide vaccination with vaccinia virus culminated in the eradication of variola virus, the causative agent of the smallpox (The global eradication of smallpox. Final report of the global commission for the certification of smallpox eradication. History of Public Health, No. 4, Geneva: World Health Organization, 1980). Since that WHO declaration, vaccination has been universally discontinued except for people at high risk of poxvirus infections (e.g. laboratory workers).

More recently, vaccinia viruses have also been used to engineer viral vectors for recombinant gene expression and for the potential use as recombinant live vaccines (Mackett, M. et al. 1982 *PNAS USA* 79:7415-7419; Smith, G. L. et al. 1984 Biotech Genet Engin. Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110, 385). The recombinant vaccinia viruses prepared in this way can be used, on the one hand, as live vaccines for the prophylaxis of infectious diseases, on the other hand, for the preparation of heterologous proteins in eukaryotic cells.

For vector applications health risks would be lessened by the use of a highly attenuated vaccinia virus strain. Several such strains of vaccinia virus were especially developed to avoid undesired side effects of smallpox vaccination. Thus, the modified vaccinia Ankara (MVA) has been generated by long-term serial passages of the Ankara strain of vaccinia virus (CVA) on chicken embryo fibroblasts (for review see Mayr, A. et al. 1975 *Infection* 3:6-14; Swiss Patent No. 568, 392). The MVA virus is publicly available from American Type Culture Collection as ATCC No. VR-1508. MVA is distinguished by its great attenuation, that is to say by diminished virulence and ability to replicate in primate cells while maintaining good immunogenicity. The MVA virus has been analyzed to determine alterations in the genome relative to the parental CVA strain. Six major deletions of genomic DNA (deletion I, II, III, IV, V, and VI) totaling 31,000 base pairs have been identified (Meyer, H. et al. 1991 *J Gen Viral* 72:1031-1038). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr A. et al. 1978 Zentralbl Bakteriol [B] 167:375-390; Stickl et al. 1974 Dtsch Med Wschr 99:2386-2392). During these studies in over 120,000 humans, including high-risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B. 1992 *PNAS USA* 89:10847-10851). Additionally, novel vaccinia vector vaccines were established on the basis of MVA having foreign DNA sequences inserted at the site of deletion III within the MVA genome (Sutter, G. et al. 1994 Vaccine 12:1032-1040).

The recombinant MVA vaccinia viruses can be prepared as set out hereinafter. A DNA-construct which contains a DNA-sequence which codes for a foreign polypeptide flanked by MVA DNA sequences adjacent to a naturally occurring deletion, e.g. deletion III, or other non-essential sites, within the MVA genome, is introduced into cells infected with MVA, to allow homologous recombination. Once the DNA-construct has been introduced into the eukaryotic cell and the foreign DNA has recombined with the viral DNA, it is possible to isolate the desired recombinant vaccinia virus in a manner known per se, preferably with the aid of a marker. The DNA-construct to be inserted can be linear or circular. A plasmid or polymerase chain reaction product is preferred. The DNA-construct contains sequences flanking the left and the right side of a naturally occurring deletion, e.g. deletion III, within the MVA genome. The foreign DNA sequence is inserted between the sequences flanking the naturally occurring deletion. For the expression of a DNA sequence or gene, it is necessary for regulatory sequences, which are required for the transcription of the gene, to be present on the DNA. Such regulatory sequences (called promoters) are known to those skilled in the art, and include for example those of the vaccinia 11 kDa gene as are described in EP-A-198,328, and those of the 7.5 kDa gene (EP-A-110,385). The DNA-construct can be introduced into the MVA infected cells by transfection, for example by means of calcium phosphate precipitation (Graham et al. 1973 *Virol* 52:456-467; Wigler et al. 1979 *Cell* 16:777-785), by means of electroporation (Neumann et al. 1982 *EMBO J* 1:841-845), by microinjection (Graessmann et al. 1.983 *Meth Enzymol* 101:482-492), by means of liposomes (Straubinger et al. 1983 *Meth Enzymol* 101:512-527), by means of spheroplasts (Schaffner 1980 *PNAS USA* 77:2163-2167) or by other methods known to those skilled in the art.

HIVs and their Replication

Figure 1:
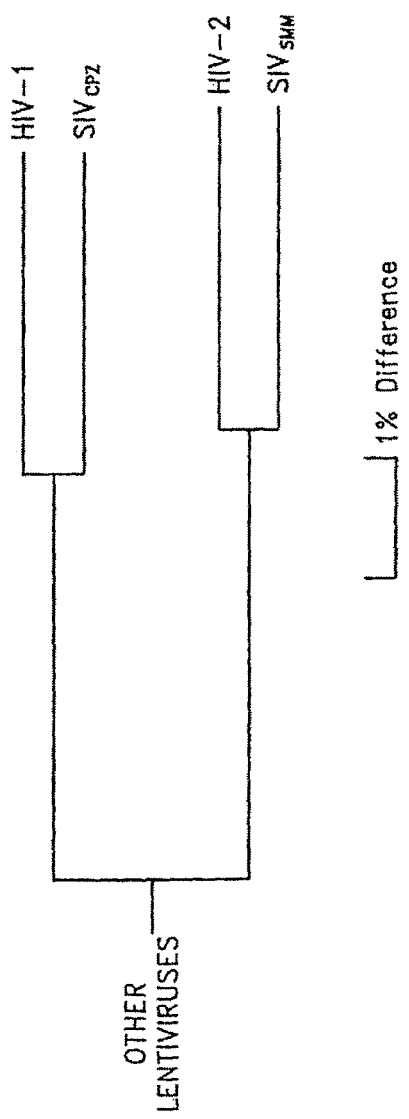
FIG. 1. Phylogenetic relationships of HIV-1 and HIV-2 based on identity of pol gene sequences. $SIV_{cpz}$ and $SIV_{smm}$ are subhuman primate lentiviruses recovered from a chimpanzee and sooty mangabey monkey, respectively.

The etiological agent of acquired immune deficiency syndrome (AIDS) is recognized to be a retrovirus exhibiting characteristics typical of the lentivirus genus, referred to as human immunodeficiency virus (HIV). The phylogenetic relationships of the human lentiviruses are shown in FIG. 1. HIV-2 is more closely related to $SIV_{smm}$, a virus isolated from sooty mangabey monkeys in the wild, than to HIV-1. It is currently believed that HIV-2 represents a zoonotic transmission of $SIV_{smm}$ to man. A series of lentiviral isolates from captive chimpanzees, designated $SIV_{cpz}$, are close genetic relatives of HIV-1.

Figure 2:
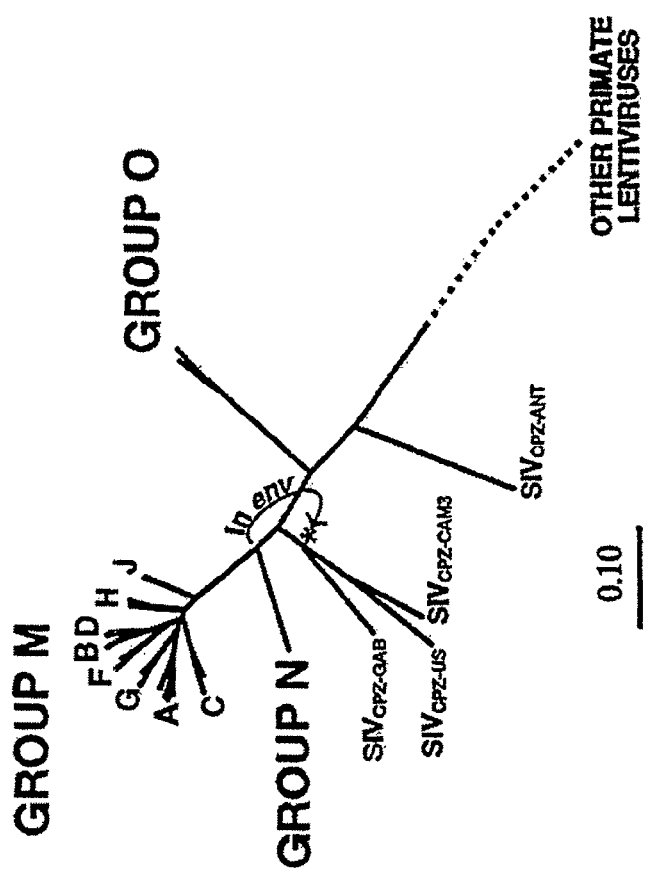
FIG. 2. Phylogenetic relationships of HIV-1 groups M; N and O with four different $SIV_{cpz}$ isolates based on full-length pol gene sequences. The bar indicates a genetic distance of 0.1 (10% nucleotide divergence) and the asterisk positions group N HIV-1 isolates based on env sequences.

The earliest phylogenetic analyses of HIV-1 isolates focused on samples from Europe/North America and Africa; discrete clusters of viruses were identified from these two areas of the world. Distinct genetic subtypes or clades of HIV-1 were subsequently defined and classified into three groups: M (major); O (outlier); and N (non-M or O) (FIG. 2). The M group of HIV-1, which includes over 95% of the global virus isolates, consists of at least eight discrete clades (A, B, C, D, F, G, H, and J), based on the sequence of complete viral genomes. Members of HIV-1 group O have been recovered from individuals living in Cameroon, Gabon, and Equatorial Guinea; their genomes share less than 50% identity in nucleotide sequence with group M viruses. The more recently discovered group N HIV-1 strains have been identified in infected Cameroonians, fail to react serologically in standard whole-virus enzyme-linked immunosorbent assay (ELISA), yet are readily detectable by conventional Western blot analysis.

Most current knowledge about HIV-1 genetic variation comes from studies of group M viruses of diverse geographic origin. Data collected during the past decade indicate that the HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

All of the HIV-1 group M subtypes can be found in Africa. Clade A viruses are genetically the most divergent and were the most common HIV-1 subtype in Africa early in the epidemic. With the rapid spread of HIV-1 to southern Africa during the mid to late 1990s, clade C viruses have become the dominant subtype and now account for 48% of HIV-1 infections worldwide. Clade B viruses, the most intensively studied HIV-1 subtype, remain the most prevalent isolates in Europe and North America.

High rates of genetic recombination are a hallmark of retroviruses. It was initially believed that simultaneous infections by genetically diverse virus strains were not likely to be established in individuals at risk for HIV-1. By 1995, however, it became apparent that a significant fraction of the HIV-1 group M global diversity included interclade viral recombinants. It is now appreciated that HIV-1 recombinants will be found in geographic areas such as Africa, South America, and Southeast Asia, where multiple HIV-1 subtypes coexist and may account for more than 10% of circulating HIV-1 strains. Molecularly, the genomes of these recombinant viruses resemble patchwork mosaics, with juxtaposed diverse HIV-1 subtype segments, reflecting the multiple crossover events contributing to their generation. Most HIV-1 recombinants have arisen in Africa and a majority contain segments originally derived from clade A viruses. In Thailand, for example, the composition of the predominant circulating strain consists of a clade A gag plus pol gene segment and a clade E env gene. Because the clade E env gene in Thai HIV-1 strains is closely related to the clade E env present in virus isolates from the Central African Republic, it is believed that the original recombination event occurred in Africa, with the subsequent introduction of a descendent virus into Thailand. Interestingly, no full-length HIV-1 subtype E isolate (i.e., with subtype E gag, pol, and env genes) has been reported to date.

The discovery that α and β chemokine receptors function as coreceptors for virus fusion and entry into susceptible $CD4^+$ cells has led to a revised classification scheme for HIV-1 (FIG. 3). Isolates can now be grouped on the basis of chemokine receptor utilization in fusion assays in which HIV-1 gp120 and $CD4^+$ coreceptor proteins are expressed in separate cells. As indicated in FIG. 3, HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

Figure 4:
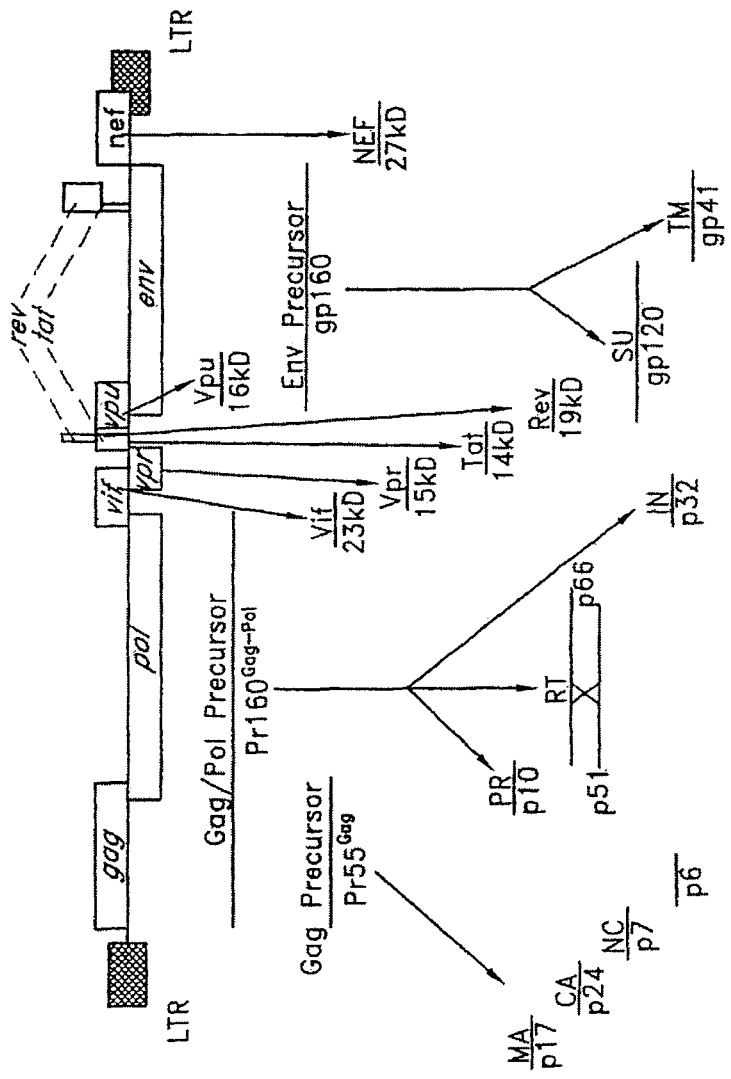
FIG. 4. HIV-encoded proteins. The location of the HIV genes, the sizes of primary translation products (in some cases polyproteins), and the processed mature viral proteins are indicated.

As is the case for all replication-competent retroviruses, the three primary HIV-1 translation products, all encoding structural proteins, are initially synthesized as polyprotein precursors, which are subsequently processed by viral or cellular proteases into mature particle-associated proteins (FIG. 4). The 55-kd Gag precursor $Pr55^{Gag}$ is cleaved into the matrix (MA), capsid (CA), nucleocapsid (NC), and p6 proteins. Autocatalysis of the 160-kd Gag-Pol polyprotein, $Pr160^{Gag-Pol}$, gives rise to the protease (PR), the heterodimeric reverse transcriptase (RT), and the integrase (IN) proteins, whereas proteolytic digestion by a cellular enzyme(s) converts the glycosylated 160-kd Env precursor gp160 to the gp120 surface (SU) and gp41 transmembrane (TM) cleavage products. The remaining six HIV-1-encoded proteins (Vif, Vpr, Tat, Rev, Vpu, and Nef) are the primary translation products of spliced mRNAs.

Gag

Figure 5:
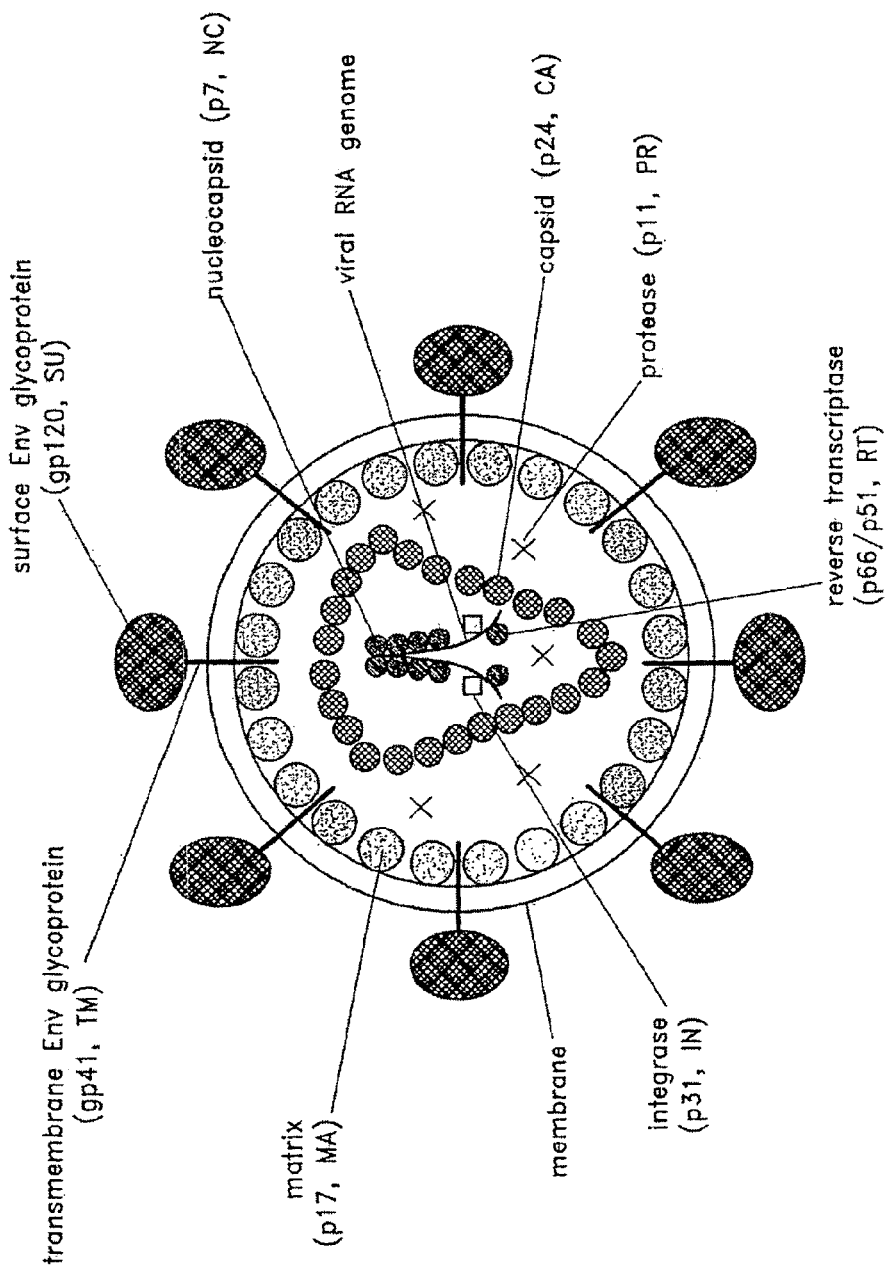
FIG. 5. Schematic representation of a mature HIV-1 virion.

The Gag proteins of HIV, like those of other retroviruses, are necessary and sufficient for the formation of noninfectious, virus-like particles. Retroviral Gag proteins are generally synthesized as polyprotein precursors; the HIV-1 Gag precursor has been named, based on its apparent molecular mass, $Pr55^{Gag}$. As noted previously, the mRNA for $Pr55^{Gag}$ is the unspliced 9.2-kb transcript (FIG. 4) that requires Rev for its expression in the cytoplasm. When the poi ORF is present, the viral protease (PR) cleaves $Pr55^{Gag}$ during or shortly after budding from the cell to generate the mature Gag proteins p17 (MA), p24 (CA), p7 (NC), and p6 (see FIG. 4). In the virion, MA is localized immediately inside the lipid bilayer of the viral envelope, CA forms the outer portion of the cone-shaped core structure in the center of the particle, and NC is present in the core in a ribonucleoprotein complex with the viral RNA genome (FIG. 5).

The HIV $Pr55^{Gag}$ precursor oligomerizes following its translation and is targeted to the plasma membrane, where particles of sufficient size and density to be visible by EM are assembled. Formation of virus-like particles by $Pr55^{Gag}$ is a self-assembly process, with critical Gag-Gag interactions taking place between multiple domains along the Gag precursor. The assembly of virus-like particles does not require the participation of genomic RNA (although the presence of nucleic acid appears to be essential), pol-encoded enzymes, or Env glycoproteins, but the production of infectious virions requires the encapsidation of the viral RNA genome and the incorporation of the Env glycoproteins and the Gag-Pol polyprotein precursor Pr160$^{Gag-Pol}$.

Pol

Downstream of gag lies the most highly conserved region of the HIV genome, the pol gene, which encodes three enzymes: PR, RT, and IN (see FIG. 4). RT and IN are required, respectively, for reverse transcription of the viral RNA genome to a double-stranded DNA copy, and for the integration of the viral DNA into the host cell chromosome. PR plays a critical role late in the life cycle by mediating the production of mature, infectious virions. The pol gene products are derived by enzymatic cleavage of a 160-kd Gag-Pol fusion protein, referred to as Pr160$^{Gag-Pol}$. This fusion protein is produced by ribosomal frameshifting during translation of Pr55$^{Gag}$ (see FIG. 4). The frame-shifting mechanism for Gag-Pol expression, also utilized by many other retroviruses, ensures that the pol-derived proteins are expressed at a low level, approximately 5% to 10% that of Gag. Like Pr55$^{Gag}$, the N-terminus of Pr160$^{Gag-Pol}$ is myristylated and targeted to the plasma membrane.

Protease

Early pulse-chase studies performed with avian retroviruses clearly indicated that retroviral Gag proteins are initially synthesized as polyprotein precursors that are cleaved to generate smaller products. Subsequent studies demonstrated that the processing function is provided by a viral rather than a cellular enzyme, and that proteolytic digestion of the Gag and Gag-Pol precursors is essential for virus infectivity. Sequence analysis of retroviral PRs indicated that they are related to cellular "aspartic" proteases such as pepsin and renin. Like these cellular enzymes, retroviral PRs use two apposed Asp residues at the active site to coordinate a water molecule that catalyzes the hydrolysis of a peptide bond in the target protein. Unlike the cellular aspartic proteases, which function as pseudodimers (using two folds within the same molecule to generate the active site), retroviral PRs function as true dimers. X-ray crystallogaphic data from HIV-1 PR indicate that the two monomers are held together in part by a four-stranded antiparallel β-sheet derived from both N- and C-terminal ends of each monomer. The substrate-binding site is located within a cleft formed between the two monomers. Like their cellular homologs, the HIV PR dimer contains flexible "flaps" that overhang the binding site and may stabilize the substrate within the cleft; the active-site Asp residues lie in the center of the dimer. Interestingly, although some limited amino acid homology is observed surrounding active-site residues, the primary sequences of retroviral PRs are highly divergent, yet their structures are remarkably similar.

Reverse Transcriptase

By definition, retroviruses possess the ability to convert their single-stranded RNA genomes into double-stranded DNA during the early stages of the infection process. The enzyme that catalyzes this reaction is RT, in conjunction with its associated RNaseH activity. Retroviral RTs have three enzymatic activities: (a) RNA-directed DNA polymerization (for minus-strand DNA synthesis), (b) RNaseH activity (for the degradation of the tRNA primer and genomic RNA present in DNA-RNA hybrid intermediates), and (c) DNA-directed DNA polymerization (for second- or plus-strand DNA synthesis).

The mature HIV-1 RT holoenzyme is a heterodimer of 66 and 51 kd subunits. The 51-kd subunit (p51) is derived from the 66-kd (p66) subunit by proteolytic removal of the C-terminal 15-kd RNaseH domain of p66 by PR (see FIG. 4). The crystal structure of HIV-1 RT reveals a highly asymmetric folding in which the orientations of the p66 and p51 subunits differ substantially. The p66 subunit can be visualized as a right hand, with the polymerase active site within the palm, and a deep template-binding cleft formed by the palm, fingers, and thumb subdomains. The polymerase domain is linked to RNaseH by the connection subdomain. The active site, located in the palm, contains three critical Asp residues (110, 185, and 186) in close proximity, and two coordinated Mg$^{2+}$ ions. Mutation of these Asp residues abolishes RT polymerizing activity. The orientation of the three active-site Asp residues is similar to that observed in other DNA polymerases (e.g., the Klenow fragment of *E. coli* DNA poII). The p51 subunit appears to be rigid and does not form a polymerizing cleft; Asp 110, 185, and 186 of this subunit are buried within the molecule. Approximately 18 base pairs of the primer-template duplex lie in the nucleic acid binding cleft, stretching from the polymerase active site to the RNaseH domain.

In the RT-primer-template-dNTP structure, the presence of a dideoxynucleotide at the 3' end of the primer allows visualization of the catalytic complex trapped just prior to attack on the incoming dNTP. Comparison with previously obtained structures suggests a model whereby the fingers close in to trap the template and dNTP prior to nucleophilic attack of the 3'-OH of the primer on the incoming dNTP. After the addition of the incoming dNTP to the growing chain, it has been proposed that the fingers adopt a more open configuration, thereby releasing the pyrophosphate and enabling RT to bind the next dNTP. The structure of the HIV-1 RNaseH has also been determined by x-ray crystallography; this domain displays a global folding similar to that of *E. coli* RNaseH.

Integrase

A distinguishing feature of retrovirus replication is the insertion of a DNA copy of the viral genome into the host cell chromosome following reverse transcription. The integrated viral DNA (the provirus) serves as the template for the synthesis of viral RNAs and is maintained as part of the host cell genome for the lifetime of the infected cell. Retroviral mutants deficient in the ability to integrate generally fail to establish a productive infection.

The integration of viral DNA is catalyzed by integrase, a 32-kd protein generated by PR-mediated cleavage of the C-terminal portion of the HIV-1 Gag-Pol polyprotein (see FIG. 4).

Retroviral IN proteins are composed of three structurally and functionally distinct domains: an N-terminal, zinc-finger-containing domain, a core domain, and a relatively non-conserved C-terminal domain. Because of its low solubility, it has not yet been possible to crystallize the entire 288-amino-acid HIV-1 IN protein. However, the structure of all three domains has been solved independently by x-ray crystallography or NMR methods. The crystal structure of the core domain of the avian sarcoma virus IN has also been determined. The N-terminal domain (residues 1 to 55), whose structure was solved by NMR spectroscopy, is composed of four helices with a zinc coordinated by amino acids His-12, His-16, Cys-40, and Cys-43. The structure of the N-terminal domain is reminiscent of helical DNA binding proteins that contain a so-called helix-turn-helix motif; however, in the HIV-1 structure this motif contributes to dimer formation. Initially, poor solubility hampered efforts to solve the structure of the core domain. However, attempts at crystallography were successful when it was observed that a Phe-to-Lys change at IN residue 185 greatly increased solubility without disrupting in vitro catalytic activity. Each monomer of the HIV-1 IN core domain (IN residues 50 to 212) is composed of a five-stranded β-sheet flanked by helices; this structure bears striking resemblance to other polynucleotidyl transferases including RNaseH and the bacteriophage MuA transposase. Three highly conserved residues are found in analogous positions in other polynucleotidyl transferases; in HIV-1 IN these are Asp-64, Asp-116 and Glu-152, the so-called D,D-35-E motif. Mutations at these positions block HIV IN function both in vivo and in vitro. The close proximity of these three amino acids in the crystal structure of both avian sarcoma virus and HIV-1 core domains supports the hypothesis that these residues play a central role in catalysis of the polynucleotidyl transfer reaction that is at the heart of the integration process. The C-terminal domain, whose structure has been solved by NMR methods, adopts a five-stranded β-barrel folding topology reminiscent of a Src homology 3 (SH3) domain. Recently, the x-ray structures of SIV and Rous sarcoma virus IN protein fragments encompassing both the core and C-terminal domains have been solved.

Env

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

Figure 6:
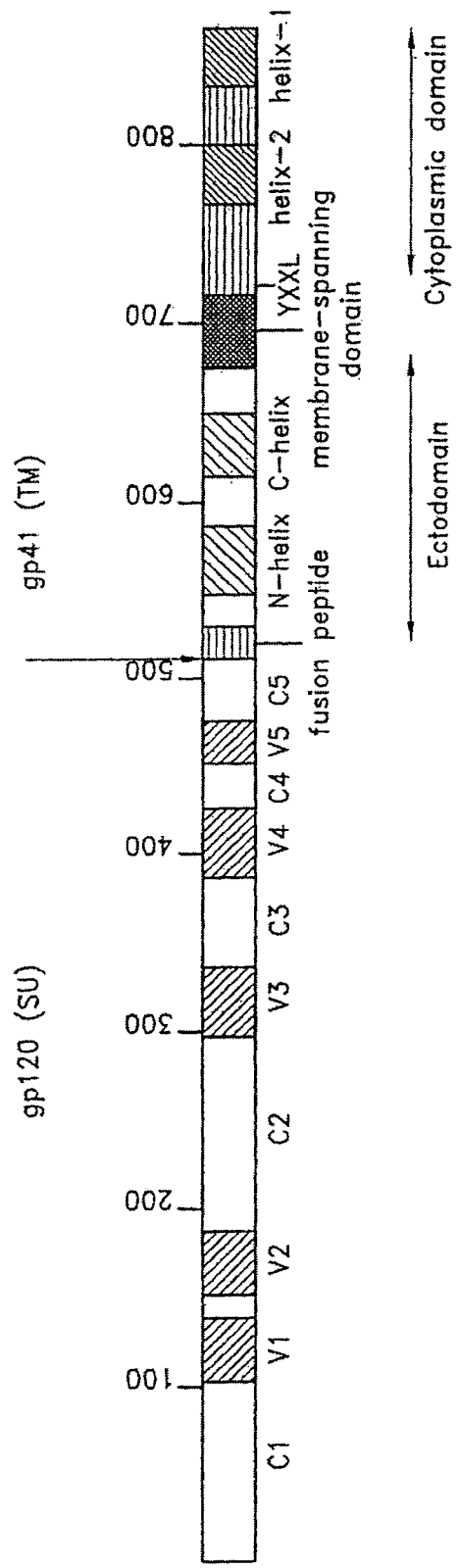
FIG. 6. Linear representation of the HIV-1 Env glycoprotein. The arrow indicates the site of gp160 cleavage to gp120 and gp41. In gp120, cross-hatched areas represent variable domains ($V_1$ to $V_5$) and open boxes depict conserved sequences ($C_1$ to $C_5$). In the gp41 ectodomain, several domains are indicated: the N-terminal fusion peptide, and the two ectodomain helices (N- and C-helix). The membrane-spanning domain is represented by a black box. In the gp41 cytoplasmic domain, the Tyr-X-X-Leu (YXXL) endocytosis motif (SEQ ID NO: 9) and two predicted helical domains (helix-1 and -2) are shown. Amino acid numbers are indicated.

The HIV Env glycoprotein is synthesized from the singly spliced 4.3-kb Vpu/Env bicistronic mRNA (see FIG. 4); translation occurs on ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41 (FIG. 6). The gp160 is cotranslationally glycosylated, forms disulfide bonds, and undergoes oligomerization in the ER. The predominant oligomeric form appears to be a trimer, although dimers and tetramers are also observed. The gp160 is transported to the Golgi, where, like other retroviral envelope precursor proteins, it is proteolytically cleaved by cellular enzymes to the mature SU glycoprotein gp120 and TM glycoprotein gp41 (see FIG. 6). The cellular enzyme responsible for cleavage of retroviral Env precursors following a highly conserved Lys/Arg-X-Lys/Arg-Arg motif is furin or a furin-like protease, although other enzymes may also catalyze gp160 processing. Cleavage of gp160 is required for Env-induced fusion activity and virus infectivity. Subsequent to gp160 cleavage, gp120 and gp41 form a noncovalent association that is critical for transport of the Env complex from the Golgi to the cell surface. The gp120-gp41 interaction is fairly weak, and a substantial amount of gp120 is shed from the surface of Env-expressing cells.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. As shown in FIG. 6, gp120 contains interspersed conserved ($C_1$ to $C_5$) and variable ($V_1$ to $V_5$) domains. The Cys residues present in the gp120s of different isolates are highly conserved and form disulfide bonds that link the first four variable regions in large loops.

A primary function of viral Env glycoproteins is to promote a membrane fusion reaction between the lipid bilayers of the viral envelope and host cell membranes. This membrane fusion event enables the viral core to gain entry into the host cell cytoplasm. A number of regions in both gp120 and gp41 have been implicated, directly or indirectly, in Env-mediated membrane fusion. Studies of the $HA_2$ hemagglutinin protein of the orthomyxoviruses and the F protein of the paramyxoviruses indicated that a highly hydrophobic domain at the N-terminus of these proteins, referred to as the fusion peptide, plays a critical role in membrane fusion. Mutational analyses demonstrated that an analogous domain was located at the N-terminus of the HIV-1, HIV-2, and SIV TM glycoproteins (see FIG. 6). Nonhydrophobic substitutions within this region of gp41 greatly reduced or blocked syncytium formation and resulted in the production of noninfectious progeny virions.

C-terminal to the gp41 fusion peptide are two amphipathic helical domains (see FIG. 6) which play a central role in membrane fusion. Mutations in the N-terminal helix (referred to as the N-helix), which contains a Leu zipper-like heptad repeat motif, impair infectivity and membrane fusion activity, and peptides derived from these sequences exhibit potent antiviral activity in culture. The structure of the ectodomain of HIV-1 and SIV gp41, the two helical motifs in particular, has been the focus of structural analyses in recent years. Structures were determined by x-ray crystallography or NMR spectroscopy either for fusion proteins containing the helical domains, a mixture of peptides derived from the N- and C-helices, or in the case of the SIV structure, the intact gp41 ectodomain sequence from residue 27 to 149. These studies obtained fundamentally similar trimeric structures, in which the two helical domains pack in an antiparallel fashion to generate a six-helix bundle. The N-helices form a coiled-coil in the center of the bundle, with the C-helices packing into hydrophobic grooves on the outside.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Use of Recombinant MVA Virus to Boost CD+8 Cell Immune Response

The present invention relates to generation of a $CD8^+$ T cell immune response against an antigen and also eliciting an antibody response. More particularly, the present invention relates to "prime and boost" immunization regimes in which the immune response induced by administration of a priming composition is boosted by administration of a boosting composition. The present invention is based on inventors' experimental demonstration that effective boosting can be achieved using modified vaccinia Ankara (MVA) vectors, following priming with any of a variety of different types of priming compositions including recombinant MVA itself.

A major protective component of the immune response against a number of pathogens is mediated by T lymphocytes of the $CD8^+$ type, also known as cytotoxic T lymphocytes (CTL). An important function of $CD8^+$ cells is secretion of gamma interferon (IFNγ), and this provides a measure of CD8+ T cell immune response. A second component of the immune response is antibody directed to the proteins of the pathogen.

The present invention employs MVA which, as the experiments described below show, has been found to be an effective means for providing a boost to a CD8+ T cell immune response primed to antigen using any of a variety of different priming compositions and also eliciting an antibody response.

Remarkably, the experimental work described below demonstrates that use of embodiments of the present invention allows for recombinant MVA virus expressing an HIV antigen to boost a CD8+ T cell immune response primed by a DNA vaccine and also eliciting an antibody response. The MVA was found to induce a CD8+ T cell response after intradermal, intramuscular or mucosal immunization. Recombinant MVA has also been shown to prime an immune response that is boosted by one or more inoculations of recombinant MVA.

Non-human primates immunized with plasmid DNA and boosted with the MVA were effectively protected against intramucosal challenge with live virus. Advantageously, the inventors found that a vaccination regime used intradermal, intramuscular or mucosal immunization for both prime and boost can be employed, constituting a general immunization regime suitable for inducing CD8+ T cells and also eliciting an antibody response, e.g. in humans.

The present invention in various aspects and embodiments employs an MVA vector encoding an HIV antigen for boosting a CD8+ T cell immune response to the antigen primed by previous administration of nucleic acid encoding the antigen and also eliciting an antibody response.

A general aspect of the present invention provides for the use of an MVA vector for boosting a CD8+ T cell immune response to an HIV antigen and also eliciting an antibody response.

One aspect of the present invention provides a method of boosting a CD8+ T cell immune response to an HIV antigen in an individual, and also eliciting an antibody response, the method including provision in the individual of an MVA vector including nucleic acid encoding the antigen operably linked to regulatory sequences for production of antigen in the individual by expression from the nucleic acid, whereby a CD8+ T cell immune response to the antigen previously primed in the individual is boosted.

An immune response to an HIV antigen may be primed by immunization with plasmid DNA or by infection with an infectious agent.

A further aspect of the invention provides a method of inducing a CD8+ T cell immune response to an HIV antigen in an individual, and also eliciting an antibody response, the method comprising administering to the individual a priming composition comprising nucleic acid encoding the antigen and then administering a boosting composition which comprises an MVA vector including nucleic acid encoding the antigen operably linked to regulatory sequences for production of antigen in the individual by expression from the nucleic acid.

A further aspect provides for use of an MVA vector, as disclosed, in the manufacture of a medicament for administration to a mammal to boost a CD8+ T cell immune response to an HIV antigen, and also eliciting an antibody response. Such a medicament is generally for administration following prior administration of a priming composition comprising nucleic acid encoding the antigen.

The priming composition may comprise any viral vector, such as a vaccinia virus vector such as a replication-deficient strain such as modified vaccinia Ankara (MVA) or NYVAC (Tartaglia et al. 1992 *Virology* 118:217-232), an avipox vector such as fowlpox or canarypox, e.g. the strain known as ALVAC (Paoletti et al. 1994 *Dev Biol Stand* 82:65-69), or an adenovirus vector or a vesicular stomatitis virus vector or an alphavirus vector.

The priming composition may comprise DNA encoding the antigen, such DNA preferably being in the form of a circular plasmid that is not capable of replicating in mammalian cells. Any selectable marker should not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boasting with a boosting composition, or first and second boosting compositions, the first and second boosting compositions being the same or different from one another. Still further boosting compositions may be employed without departing from the present invention. In one embodiment, a triple immunization regime employs DNA, then adenovirus as a first boosting composition, then MVA as a second boosting composition, optionally followed by a further (third) boosting composition or subsequent boosting administration of one or other or both of the same or different vectors. Another option is DNA then MVA then adenovirus, optionally followed by subsequent boosting administration of one or other or both of the same or different vectors.

The antigen to be encoded in respective priming and boosting compositions (however many boosting compositions are employed) need not be identical, but should share at least one CD8+ T cell epitope. The antigen may correspond to a complete antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

An HIV antigen of the invention to be encoded by a recombinant MVA virus includes polypeptides having immunogenic activity elicited by an amino acid sequence of an HIV Env, Gag, Pol, Vif, Vpr, Tat, Rev, Vpu, or Nef amino acid sequence as at least one CD8+ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full length Env precursor sequence is presented for use in the present invention, Env is optionally deleted of subsequences. For example, regions of the gp120 surface and gp41 transmembrane cleavage products can be deleted.

Although a full length Gag precursor sequence is presented for use in the present invention, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full length Pol precursor sequence is presented for use in the present invention, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Percent identify can be determined, for example, by comparing sequence information using the GAP computer program, version 6.0, available from the University of Wisconsin Genetics Computer Group (UWGCG). The GAP program utilizes the alignment method of Needleman and Wunsch (*J Mol Biol* 1970 48:443), as revised by Smith and Waterman (*Adv Appl Math* 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (*Nucl Acids Res* 1986 14:6745), as described by Schwartz and Dayhoff (eds., *Atlas of Protein Sequence and Structure*, National Biomedical Research Foundation, Washington, D.C. 1979, pp. 353-358); (2) a penalty of 3.0 for each gap and an additional 0.10 penalty for each symbol in each gap; and (3) no penalty for end gaps.

In a preferred embodiment, an Env of the present invention is a variant form of at least one HIV envelope protein. Preferably, the Env is composed of gp120 and the membrane-spanning and ectodomain of gp41 but lacks part or all of the cytoplasmic domain of gp41.

Known HIV sequences are readily available from commercial and institutional HIV sequence databases, such as GEN-BANK, or as published compilations, such as Myers et al. eds., Human Retroviruses and AIDS, A Compilation and Analysis of Nucleic Acid and Amino Acid Sequences, Vol. I and II, Theoretical Biology and Biophysics, Los Alamos, N. Mex. (1993).

Substitutions or insertions of an HIV Env, Gag, or Pol to obtain an additional HIV Env, Gag, or Pol, encoded by a nucleic acid for use in a recombinant MVA virus of the present invention, can include substitutions or insertions of at least one amino acid residue (e.g., 1-25 amino acids). Alternatively, at least one amino acid (e.g., 1-25 amino acids) can be deleted from an HIV Env, Gag, or Pol sequence. Preferably, such substitutions, insertions or deletions are identified based on safety features, expression levels, immunogenicity and compatibility with high replication rates of MVA.

Amino acid sequence variations in an HIV Env, Gag, or Pol of the present invention can be prepared e.g., by mutations in the DNA. Such HIV Env, Gag, or Pol include, for example, deletions, insertions or substitutions of nucleotides coding for different amino acid residues within the amino acid sequence. Obviously, mutations that will be made in nucleic acid encoding an HIV Env, Gag, or Pol must not place the sequence out of reading frame and preferably will not create complementary domains that could produce secondary mRNA structures.

HIV Env, Gag, or Pol-encoding nucleic acid of the present invention can also be prepared by amplification or site-directed mutagenesis of nucleotides in DNA or RNA encoding an HIV Env, Gag, or Pol and thereafter synthesizing or reverse transcribing the encoding DNA to produce DNA or RNA encoding an HIV Env, Gag, or Pol, based on the teaching and guidance presented herein.

Recombinant MVA viruses expressing HIV Env, Gag, or Pol of the present invention, include a finite set of HIV Env, Gag, or Pol-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., 1978 *Principles of Protein Structure*, Springer-Verlag, New York, N.Y., and Creighton, T. E., 1983 *Proteins: Structure and Molecular Properties*, W.H. Freeman & Co., San Francisco, Calif. For a presentation of nucleotide sequence substitutions, such as codon preferences, see Ausubel et al. eds. *Current Protocols in Molecular Biology*, Greene Publishing Assoc., New York, N.Y. 1994 at §§A.1.1-A.1.24, and Sambrook, J. et al. 1989 *Molecular Cloning: A Laboratory. Manual*, Second Edition, Cold Spring Harbor Laboratory Press, Cold Spring Harbor, N.Y. at Appendices C and D.

Thus, one of ordinary skill in the art, given the teachings and guidance presented herein, will know how to substitute other amino acid residues in other positions of an HIV env, gag, or pol DNA or RNA to obtain alternative HIV Env, Gag, or Pol, including substitutional, deletional or insertional variants.

Within the MVA vector, regulatory sequences for expression of the encoded antigen will include a natural, modified or synthetic poxvirus promoter. By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, marker genes and other sequences may be included as appropriate, in accordance with the knowledge and practice of the ordinary person skilled in the art: see, for example, Moss, B. (2001). Poxyiridae: the viruses and their replication. In Fields Virology, D. M. Knipe, and P. M. Howley, eds. (Philadelphia, Lippincott Williams & Wilkins), pp. 2849-2883. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* 1998 Ausubel et al. eds., John Wiley & Sons.

Promoters for use in aspects and embodiments of the present invention must be compatible with poxvirus expression systems and include natural, modified and synthetic sequences.

Either or both of the priming and boosting compositions may include an adjuvant, such as granulocyte macrophage-colony stimulating factor (GM-CSF) or encoding nucleic acid therefor.

Administration of the boosting composition is generally about 1 to 6 months after administration of the priming composition, preferably about 1 to 3 months.

Preferably, administration of priming composition, boosting composition, or both priming and boosting compositions, is intradermal, intramuscular or mucosal immunization.

Administration of MVA vaccines may be achieved by using a needle to inject a suspension of the virus. An alternative is the use of a needleless injection device to administer a virus suspension (using, e.g., BIOJECTOR™ needleless injector (Bioject Medical Technologies, Inc., Lake Forest, Calif.)) or a resuspended freeze-dried powder containing the vaccine, providing for manufacturing individually prepared doses that do not need cold storage. This would be a great advantage for a vaccine that is needed in rural areas of Africa.

MVA is a virus with an excellent safety record in human immunizations. The generation of recombinant viruses can be accomplished simply, and they can be manufactured reproducibly in large quantities. Intradermal, intramuscular or mucosal administration of recombinant MVA virus is therefore highly suitable for prophylactic or therapeutic vaccination of humans against AIDS which can be controlled by a CD8+ T cell response.

The individual may have AIDS such that delivery of the antigen and generation of a CD8+ T cell immune response to the antigen is of benefit or has a therapeutically beneficial effect.

Most likely, administration will have prophylactic aim to generate an immune response against HIV or AIDS before infection or development of symptoms.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. intravenous, cutaneous or subcutaneous, nasal, intramuscular, intraperitoneal routes.

As noted, administration is preferably intradermal, intramuscular or mucosal.

Physiological saline solution, dextrose or other saccharide solution or glycols such as ethylene glycol, propylene glycol or polyethylene glycol may be included.

For intravenous, cutaneous, subcutaneous, intramuscular or mucosal injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included as required.

A slow-release formulation may be employed.

Following production of MVA particles and optional formulation of such particles into compositions, the particles may be administered to an individual, particularly human or other primate. Administration may be to another mammal, e.g. rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* 16th edition, 1980, Osol, A. (ed.).

In one preferred regimen, DNA is administered at a dose of 250 μg to 2.5 mg/injection, followed by MVA at a dose of $10^6$ to $10^9$ infectious virus particles/injection.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g. protection against HIV or AIDS.

Further aspects and embodiments of the present invention will be apparent to those of ordinary skill in the art, in view of the above disclosure and following experimental exemplification, included by way of illustration and not limitation, and with reference to the attached figures.

EXAMPLE 1

Control of a Mucosal Challenge and Prevention of Aids by a Multiprotein DNA/MVA Vaccine Here we tested DNA priming and poxvirus boosting for the ability to protect against a highly pathogenic mucosal challenge. The 89.6 chimera of simian and human immunodeficiency viruses (SHIV-89.6) was used for the construction of immunogens and its highly pathogenic derivative, SHIV-89.6P, for challenge (G. B. Karlsson et al. 1997 *J Virol* 71:4218). SHIV-89.6 and SHIV-89.6P do not generate cross-neutralizing antibody (D. C. Montefiori et al. 1998 *J Virol* 72:3427) and allowed us to address the ability of vaccine-raised T cells and non-neutralizing antibodies to control an immunodeficiency virus challenge. Modified vaccinia Ankara (MVA) was used for the construction of the recombinant poxvirus. MVA has been highly effective at boosting DNA-primed CD8 T cells and enjoys the safety feature of not replicating efficiently in human or monkey cells (H. L. Robinson et al. 2000 *AIDS Reviews* 2:105).

To ensure a broad immune response both the DNA and recombinant MVA (rMVA) components of the vaccine expressed multiple immunodeficiency virus proteins. The DNA prime (DNA/89.6) expressed simian immunodeficiency virus (SIV) Gag, Poi, Vif, Vpx, and Vpr and human immunodeficiency virus-1 (HIV-1) Env, Tat, and Rev from a single transcript (R. J. Gorelick et al. 1.999 *Virology* 253:259; M. M. Sauter et al. 1996 *J Cell Biol* 132:795).

Molecularly cloned SHIV-89.6 sequences were cloned into the vector pGA2 using ClaI and RsrII sites. This cloning deleted both long terminal repeats (LTRs) and nef. The SHIV-89.6 sequences also were internally mutated for a 12-base pair region encoding the first four amino acids of the second zinc finger in nucleocapsid. This mutation renders SHIV viruses noninfectious (R. J. Gorelick et al. 1999 *Virology* 253:259). A mutation in gp41 converted the tyrosine at position 710 to cysteine to achieve better expression of Env on the plasma membrane of DNA-expressing cells (M. M. Sauter et al. 1996 *J Cell Biol* 132:795). pGA2 uses the CMV immediate early promoter without intron A and the bovine growth hormone polyadenylation sequence to express vaccine inserts. Vaccine DNA was produced by Althea (San Diego, Calif.). In transient transfections of 293T cells, DNA/89.6 produced about 300 ng of Gag and 85 ng of Env per $1\times10^6$ cells.

The rMVA booster (MVA/89.6) expressed SIV Gag, Pol, and HIV-1 Env under the control of vaccinia virus early/late promoters.

The MVA double recombinant virus expressed both the HIV 89.6 Env and the SIV 239 Gag-Pol, which were inserted into deletion II and deletion III of MVA, respectively. The 89.6 Env protein was truncated for the COOH-terminal 115 amino acids of gp41. The modified H5 promoter controlled the expression of both foreign genes.

Vaccination was accomplished by priming with DNA at 0 and 8 weeks and boosting with rMVA at 24 weeks (FIG. 7A).

I.d. and i.m. DNA immunizations were delivered in phosphate-buffered saline (PBS) with a needleless jet injector (Bioject, Portland, Oreg.) to deliver five i.d. 100-μl injections to each outer thigh for the 2.5-mg dose of DNA or one i.d. 100-μl injection to the right outer thigh for the 250-μg dose of plasmid. I.m. deliveries of DNA were done with one 0.5-ml injection of DNA in PBS to each outer thigh for the 2.5-mg dose and one 100-μl injection to the right outer thigh for the 250-μg dose. $1 \times 10^8$ pfu of MVA/89.6 was administered both i.d. and i.m. with a needle. One 100-μl dose was delivered to each outer thigh for the i.d. dose and one 500-μl dose to each outer thigh for the i.m dose. Control animals received 2.5 mg of the pGA2 vector without vaccine insert with the Bioject device to deliver five 100-μl doses i.d. to each outer thigh. The control MVA booster immunization consisted of $2 \times 10^8$ pfu of MVA without an insert delivered i.d. and i.m. as described for MVA/89.6.

Four groups of six rhesus macaques each were primed with either 2.5 mg (high-dose) or 250 μg (low-dose) of DNA by intradermal (i.d.) or intramuscular (i.m.) routes using a needleless jet injection device (Bioject, Portland, Oreg.) (T. M. Allen et al. 2000 *J Immunol* 164:4968).

Young adult rhesus macaques from the Yerkes breeding colony were cared for under guidelines established by the Animal Welfare Act and the NIH "Guide for the Care and Use of Laboratory Animals" with protocols approved by the Emory University Institutional Animal Care and Use Committee. Macaques were typed for the Mamu-A*01 allele with polymerase chain reaction (PCR) analyses (M. A. Egan et al. 2000 *J Viral* 74:7485; I. Ourmanov et al. 2000 *J Viral* 74:2740). Two or more animals containing at least one Mamu-A*01 allele were assigned to each group. Animal numbers are as follows: 1, RBr-5*; 2, RIm-5*; 3, RQf-5*; 4, RZe-5; 5, ROm-5; 6, RDm-5; 7, RAj-5*; 8, RJi-5*; 9, RAl-5*; 10, RDe-5*; 11, RAi-5; 12, RPr-5; 13, RKw-4*; 14, RWz-5*; 15, RGo-5; 16, RLp-4; 17, RWd-6; 18, RAt-S; 19, RPb-5*; 20, RIi-5*; 21, RIq-5; 22, RSp-4; 23, RSn-5; 24, RGd-6; 25, RMb-5*; 26, RGy-5*; 27, RUs-4; and 28, RPm-5. Animals with the A*01 allele are indicated with asterisks.

Gene gun deliveries of DNA were not used because these had primed non-protective immune responses in a 1996-98 trial (H. L. Robinson et al. 1999 *Nat Med* 5:526). The MVA/89.6 booster immunization ($2 \times 10^8$ plaque-forming units, pfu) was injected with a needle both i.d. and i.m. A control group included two mock immunized animals and two naive animals. The challenge was given at 7 months after the rMVA booster to test for the generation of long-term immunity. Because most HIV-1 infections are transmitted across mucosal surfaces, an intrarectal challenge was administered.

DNA priming followed by rMVA boosting generated high frequencies of virus-specific T cells that peaked at one week following the rMVA booster (FIG. 7). The frequencies of T cells recognizing the Gag-CM9 epitope were assessed by means of Mamu-A*01 tetramers, and the frequencies of T cells recognizing epitopes throughout Gag were assessed with pools of overlapping peptides and an enzyme-linked immunospot (ELISPOT) assay (C. A. Power et al. 1999 *J Immunol Methods* 227:99).

For tetramer analyses, about $1 \times 10^6$ peripheral blood mononuclear cells (PBMC) were surface-stained with antibodies to CD3 conjugated to fluorescein isothiocyanate (FITC) (FN-18; Biosource International, Camarillo, Calif.), CD8 conjugated to peridinin chlorophyl protein (PerCP) (SK1; Becton Dickinson, San Jose, Calif.), and Gag-CM9 (CTPY-DINQM)-Manzu-A*01 tetramer (SEQ ID NO: 6) conjugated to allophycocyanin (APC), in a volume of 100 μl at 8° to 10° C. for 30 min. Cells were washed twice with cold PBS containing 2% fetal bovine serum (FBS), fixed with 1% paraformaldehyde in PBS, and analyzed within 24 hrs on a FACScaliber (Becton Dickinson, San Jose, Calif.). Cells were initially gated on lymphocyte populations with forward scatter and side scatter and then on CD3 cells. The CD3 cells were then analyzed for CD8 and tetramer-binding cells. About 150,000 lymphocytes were acquired for each sample. Data were analyzed using FloJo software (Tree Star, San Carlos, Calif.).

For interferon-γ (IFN-γ) ELISPOTs, MULTISCREEN 96 well filtration plates (Millipore Inc. Bedford, Mass.) were coated overnight with antibody to human IFN-γ (Clone B27, Pharmingen, San Diego, Calif.) at a concentration of 2 μg/ml in sodium bicarbonate buffer (pH 9.6) at 8° to 10° C. Plates were washed two times with RPMI medium and then blocked for 1 hour with complete medium (RPMI containing 10% FBS) at 37° C. Plates were washed five more times with plain RPMI medium, and cells were seeded in duplicate in 100 μl complete medium at numbers ranging from $2 \times 10^4$ to $5 \times 10^5$ cells per well. Peptide pools were added to each well to a final concentration of 2 μg/ml of each peptide in a volume of 100 μl in complete medium. Cells were cultured at 37° C. for about 36 hrs under 5% $CO_2$. Plates were washed six times with wash buffer (PBS with 0.05% Tween-20) and then incubated with 1 μg of biotinylated antibody to human IFN-γ per milliliter (clone 7-86-1; Diapharma Group, West Chester, Ohio) diluted in wash buffer containing 2% FBS. Plates were incubated for 2 hrs at 37° C. and washed six times with wash buffer. Avidin-horseradish peroxidase (Vector Laboratories, Burlingame, Calif.) was added to each well and incubated for 30 to 60 min at 37° C. Plates were washed six times with wash buffer and spots were developed using stable DAB as substrate (Research Genetics, Huntsville, Ala.). Spots were counted with a stereo dissecting microscope. An ovalbumin peptide (SIINFEKL) (SEQ ID NO: 7) was included as a control in each analysis. Background spots for the ovalbumin peptide were generally <5 for $5 \times 10^5$ PBMCs. This background when normalized for $1 \times 10^6$ PBMC was <10. Only ELISPOT counts of twice the background (≥20) were considered significant. The frequencies of ELISPOTs are approximate because different dilutions of cells have different efficiencies of spot formation in the absence of feeder cells (C. A. Power et al. 1999 *J Immunol Methods* 227: 99). The same dilution of cells was used for all animals at a given time point, but different dilutions were used to detect memory and acute responses.

Figure 7A:
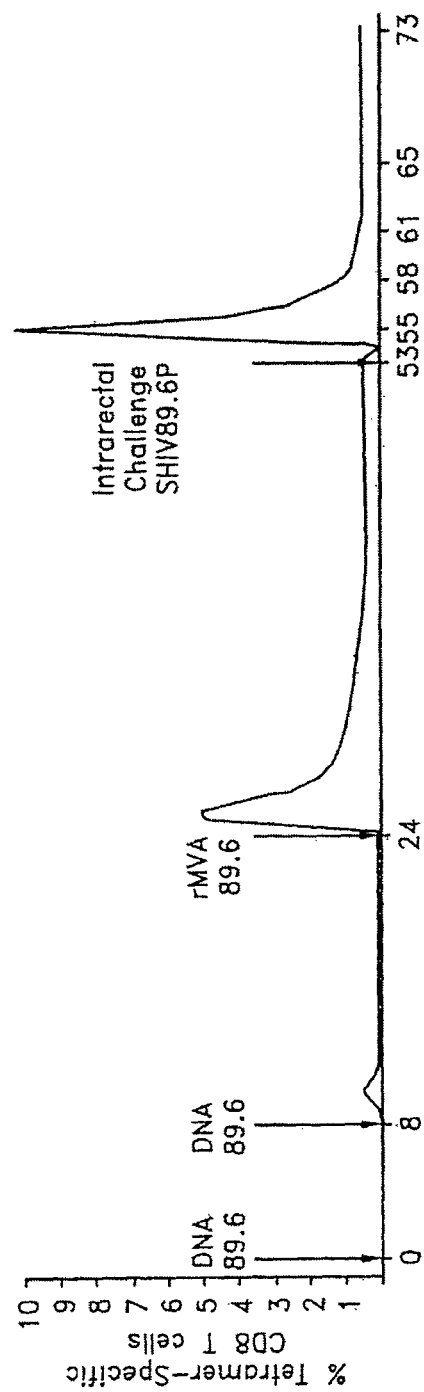
FIG. 7. Temporal frequencies of Gag-specific T cells. (A) Gag-specific CD8 T cell responses raised by DNA priming and rMVA booster immunizations. The schematic presents mean Gag-CM9-tetramer data generated in the high-dose i.d. DNA-immunized animals. (B) Gag-specific IFN-γ ELISPOTs in A*01 (open bars) and non-A*01 (filled bars) macaques at various times before challenge and at two weeks after challenge. Three pools of 10 to 13 Gag peptides (22-mers overlapping by 12) were used for the analyses. The numbers above data bars represent the arithmetic mean±SD for the ELISPOTs within each group. The numbers at the top of the graphs designate individual animals. *, data not available; #, <20 ELISPOTs per $1 \times 10^6$ peripheral blood mononuclear cells (PBMC). Temporal data for Gag-CM9-Mamu-A*01 tetramer-specific T cells can be found in FIG. 12.
Figure 7B:
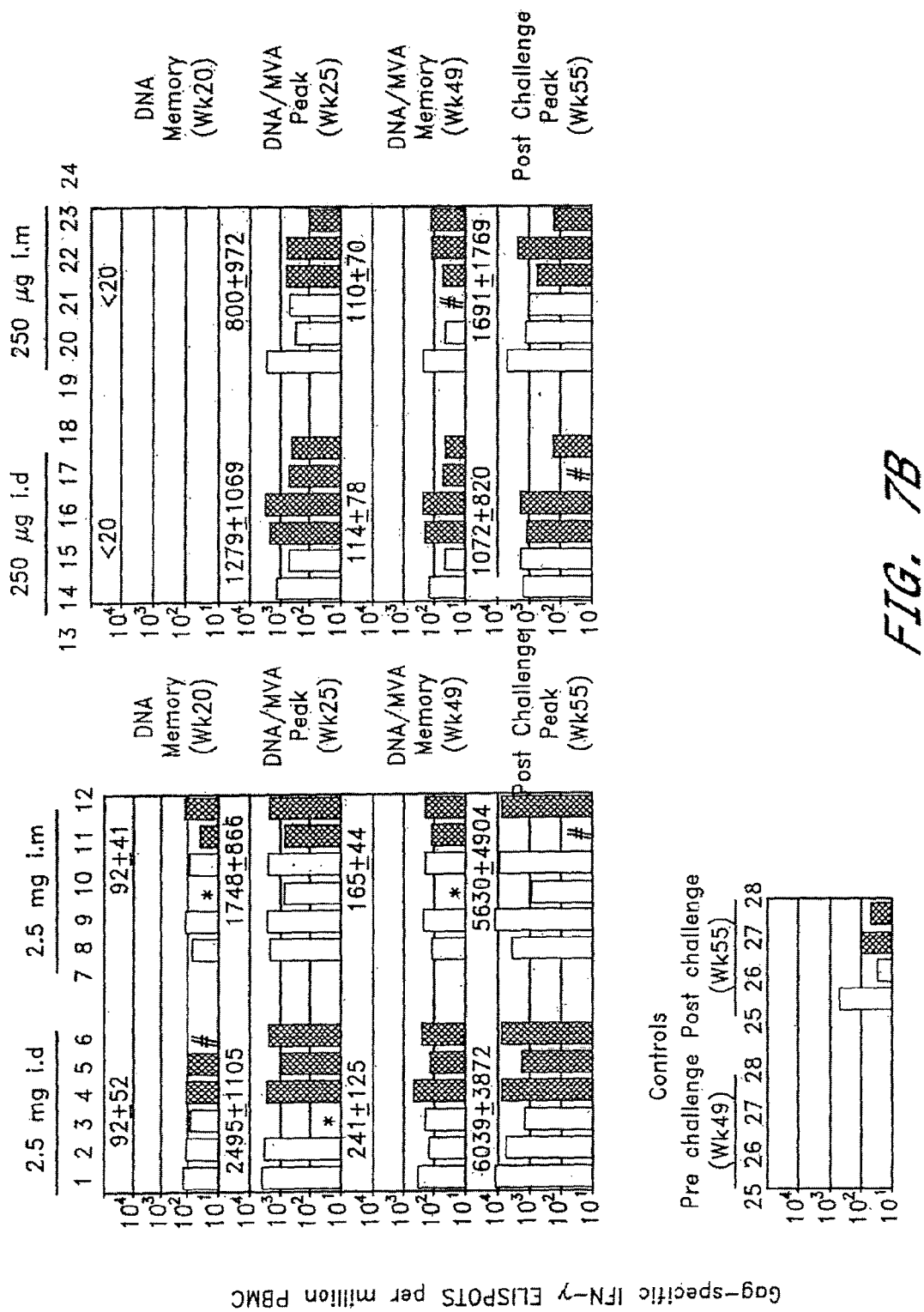
Figure 12:
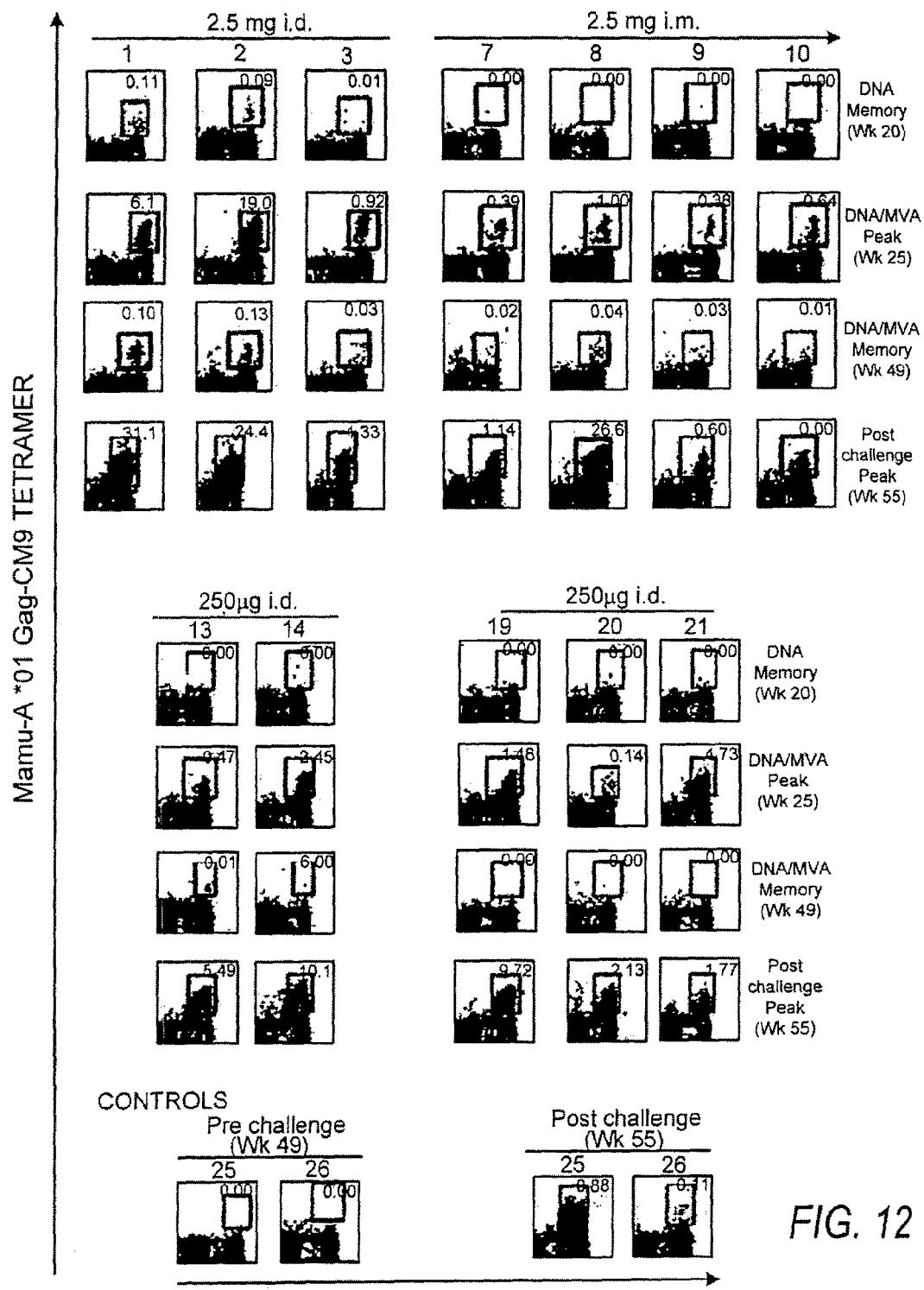
FIG. 12. Gag-CM9-Mamu-A*01 tetramer-specific T cells in Mamu-A*01 vaccinated and control macaques at various times before challenge and at two weeks after challenge. The number at the upper right corner of each plot represents the frequency of tetramer-specific CD8 T cells as a % of total CD8 T cells. The numbers above each column of FACS data designate individual animals.
Figure 13:
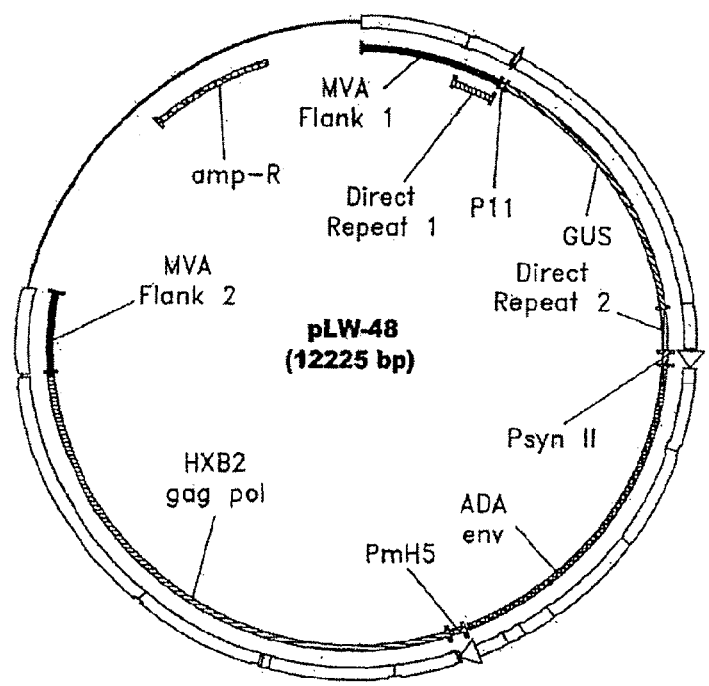
FIG. 13. Map of plasmid transfer vector pLW-48.

Gag-CM9 tetramer analyses were restricted to macaques that expressed the Mamu-A*01 histocompatibility type, whereas ELISPOT responses did not depend on a specific histocompatibility type. As expected, the DNA immunizations raised low levels of memory cells that expanded to high frequencies within 1 week of the rMVA booster (FIGS. 7 and 12). In Mamu-A*01 macaques, CD8 cells specific to the Gag-CM9 epitope expanded to frequencies as high as 19% of total CD8 T cells (FIG. 12). This peak of specific cells underwent a 10- to 100-fold contraction into the DNA/MVA memory pool (FIGS. 7A and 12). ELISPOTs for three pools of Gag peptides also underwent a major expansion (frequencies up to 4000 spots for $1 \times 10^6$ PBMC) before contracting from 5- to 20-fold into the DNA/MVA memory response (FIG. 7B). The frequencies of ELISPOTs were the same in macaques with and without the A*01 histocompatibility type (P>0.2).

Simple linear regression was used to estimate correlations between postbooster and postchallenge ELISPOT responses, between memory and postchallenge ELISPOT responses, and between logarithmically transformed viral loads and ELISPOT frequencies. Comparisons between vaccine and control groups and A*01 and non A*01 macaques were performed by means of two-sample t tests with logarithmically transformed viral load and ELISPOT responses. Two-way analyses of variance were used to examine the effects of dose and route of administration on peak DNA/MVA ELISPOTs, on memory DNA/MVA ELISPOTs, and on logarithmically transformed Gag antibody data.

At both peak and memory phases of the vaccine response, the rank order for the height of the ELISPOTs in the vaccine groups was 2.5 mg i.d.>2.5 mg i.m.>250 µg i.d.>250 µg i.m. (FIG. 7B). The IFN-γ ELISPOTs included both CD4 and CD8 cells. Gag-CM9-specific CD8 cells had good lytic activity after restimulation with peptide.

The highly pathogenic SHIV-89.6P challenge was administered intrarectally at 7 months after the rMVA booster, when vaccine-raised T cells were in memory (FIG. 7).

The challenge stock ($5.7 \times 10^9$ copies of viral RNA per milliliter) was produced by one intravenous followed by one intrarectal passage in rhesus macaques of the original SHIV-89.6P stock (G. B. Karlsson et al. 1997 *J Viral* 71:4218). Lymphoid cells were harvested from the intrarectally infected animal at peak viremia, CD8-depleted, and mitogen-stimulated for stock production. Before intrarectal challenge, fasted animals were anesthetized (ketamine, 10 mg/kg) and placed on their stomach with the pelvic region slightly elevated. A feeding tube (8Fr (2.7 mm)×16 inches (41 cm); Sherwood Medical, St. Louis, Mo.) was inserted into the rectum for a distance of 15 to 20 cm. Following insertion of the feeding tube, a syringe containing 20 intrarectal infectious doses in 2 ml of RPMI-1640 plus 10% FBS was attached to the tube and the inoculum was slowly injected into the rectum. After delivery of the inoculum, the feeding tube was flushed with 3.0 ml of RPMI without FBS and then slowly withdrawn. Animals were left in place, with pelvic regions slightly elevated, for a period of ten minutes after the challenge.

The challenge infected all of the vaccinated and control animals (FIG. 8). However, by 2 weeks after challenge, titers of plasma viral RNA were at least 10-fold lower in the vaccine groups (geometric means of $1 \times 10^7$ to $5 \times 10^7$) than in the control animals (geometric mean of $4 \times 10^8$) (FIG. 8A) (S. Staprans et al. in: *Viral Genome Methods* K. Adolph, ed. CRC Press, Boca Raton, Fla., 1996 pp. 167-184; R. Hofmann-Lehmann et al. 2000 *AIDS Res Hum Retroviruses* 16:1247).

For the determination of SHIV copy number, viral RNA from 150 µl of ACD anticoagulated plasma was directly extracted with the QIAamp Viral RNA kit (Qiagen), eluted in 60 µl of AVE buffer, and frozen at −80° C. until SHIV RNA quantitation was performed. Five microliters of purified plasma RNA was reverse-transcribed in a final 20-µl volume containing 50 mM KCl, 10 mM Tris-HCl (pH 8.3), 4 mM MgCl$_2$, 1 mM each deoxynucleotide triphosphate (dNTP), 2.5 µM random hexamers, 20 units MultiScribe RT, and 8 units ribonuclease inhibitor. Reactions were incubated at 25° C. for 10 min, followed by incubation at 42° C. for 20 min, and inactivation of reverse transcriptase at 99° C. for 5 min. The reaction mix was adjusted to a final volume of 50 µl containing 50 mM KCl, 10 mM Tris-HCl (pH 8.3), 4 mM MgCl$_2$, 0.4 mM each dNTP, 0.2 µM forward primer, 0.2 µM reverse primer, 0.1 µM probe, and 5 units AmpliTaq Gold DNA polymerase (all reagents from PerkinElmer Applied Biosystems, Foster City, Calif.). The primer sequences within a conserved portion of the SIV gag gene are the same as those described previously (S. Staprans et al. in: *Viral Genome Methods* K. Adolph, ed. CRC Press, Boca Raton, Fla., 1996 pp. 167-184). A PerkinElmer Applied Biosystems 7700 Sequence Detection System was used with the PCR profile: 95° C. for 10 min, followed by 40 cycles at 93° C. for 30 s, and 59.5° C. for 1 min. PCR product accumulation was monitored with the 7700 sequence detector and a probe to an internal conserved gag gene sequence: 6FAM-CTGTCTGCGT-CATTTGGTGC-Tamra (SEQ ID NO: 8), where FAM and Tamra denote the reporter and quencher dyes. SHIV RNA copy number was determined by comparison with an external standard Curve consisting of virion-derived SIVmac239 RNA quantified by the SIV bDNA method (Bayer Diagnostics, Emeryville, Calif.). All specimens were extracted and amplified in duplicate, with the mean result reported. With a 0.15-ml plasma input, the assay has a sensitivity of $10^3$ RNA copies per milliliter of plasma and a linear dynamic range of $10^3$ to $10^8$ RNA copies ($R^2=0.995$). The intranssay coefficient of variation was <20% for samples containing >$10^4$ SHIV RNA copies per milliliter, and <25% for samples containing $10^3$ to $10^4$ SHIV RNA copies per milliliter. To more accurately quantitate low SHIV RNA copy number in vaccinated animals at weeks 16 and 20, we made the following modifications to increase the sensitivity of the SHIV RNA assay: (i) Virions from ≤1 ml of plasma were concentrated by centrifugation at 23,000 g at 10° C. for 150 min before viral RNA extraction, and (ii) a one-step reverse transcriptase PCR method was used (R. Hofmann-Lehmann et al. 2000 *AIDS Res Hum Retroviruses* 16:1247). These changes provided a reliable quantification limit of 300 SHIV RNA copies per milliliter, and gave SHIV RNA values that were highly correlated to those obtained by the first method used ($r=0.91$, $P<0.0001$).

Figure 8C:
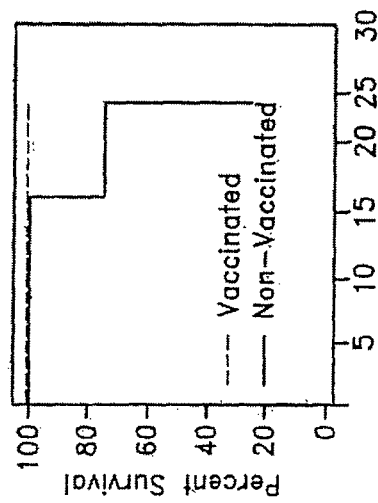
FIG. 8. Temporal viral loads, CD4 counts, and survival after challenge of vaccinated and control animals. (A) Geometric mean viral loads and (B) geometric mean CD4 counts. (C) Survival curve for vaccinated and control animals. The dotted line represents all. 24 vaccinated animals. (D) Viral loads and (E) CD4 counts for individual animals in the vaccine and control groups. The key to animal numbers is presented in (E). Assays for the first 12 weeks after challenge had a detection level of 1000 copies of RNA per milliliter of plasma. Animals with loads below 1000 were scored with a load of 500. For weeks 16 and 20, the detection level was 300 copies of RNA per milliliter. Animals with levels of virus below 300 were scored at 300.

By 8 weeks after challenge, both high-dose DNA-primed groups and the low-dose i.d. DNA-primed group had reduced their geometric mean loads to about 1000 copies of viral RNA per milliliter. At this time, the low-dose i.m. DNA-primed group had a geometric mean of $6 \times 10^3$ copies of viral RNA and the nonvaccinated controls had a geometric mean of $2 \times 10^6$. By 20 weeks after challenge, even the low-dose i.m. group had reduced its geometric mean copies of viral RNA to 1000. Among the 24 vaccinated animals, only one animal, animal number 22 in the low-dose i.m. group, had intermittent viral loads above $1 \times 10^4$ copies per milliliter (FIG. 8D).

Figure 8B:
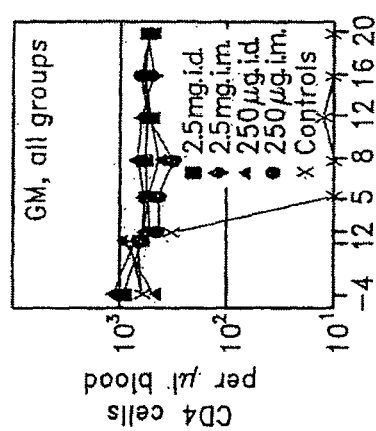
Figure 8A:
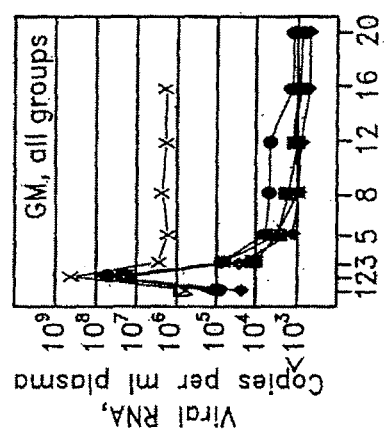
Figure 8D:
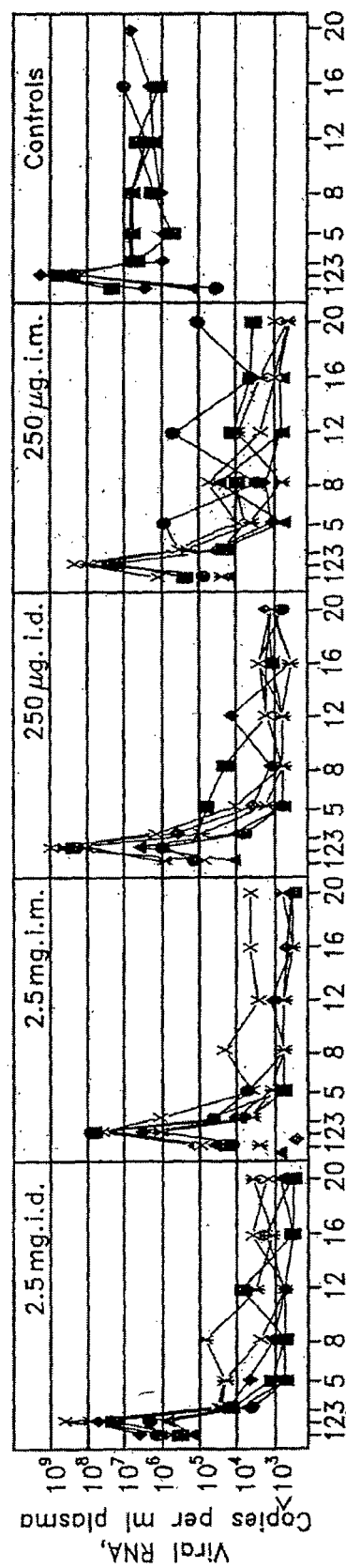
Figure 8E:
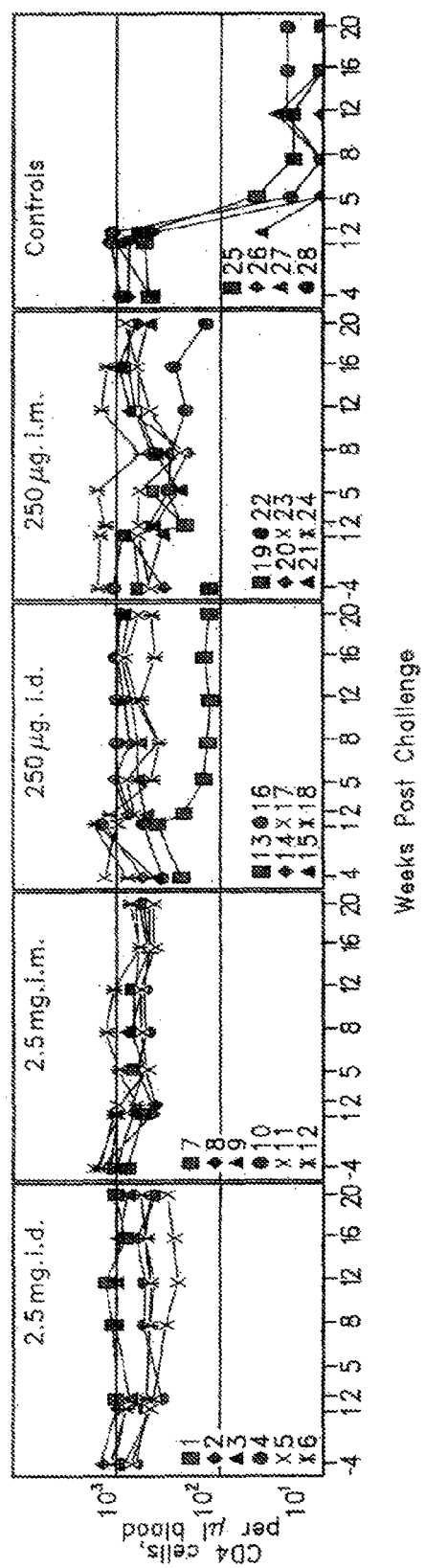

By 5 weeks after challenge, all of the nonvaccinated controls had undergone a profound depletion of CD4 cells (FIG. 8B). All of the vaccinated animals maintained their CD4 cells, with the exception of animal 22 in the low dose i.m. group (see above), which underwent a slow CD4 decline (FIG. 8E). By 23 weeks after challenge, three of the four control animals had succumbed to AIDS (FIG. 8C). These animals had variable degrees of enterocolitis with diarrhea, cryptosporidiosis, colicystitis, enteric *campylobacter* infection, splenomegaly, lymphadenopathy, and SIV-associated giant cell pneumonia. In contrast, all 24 vaccinated animals maintained their health.

Figure 9A:
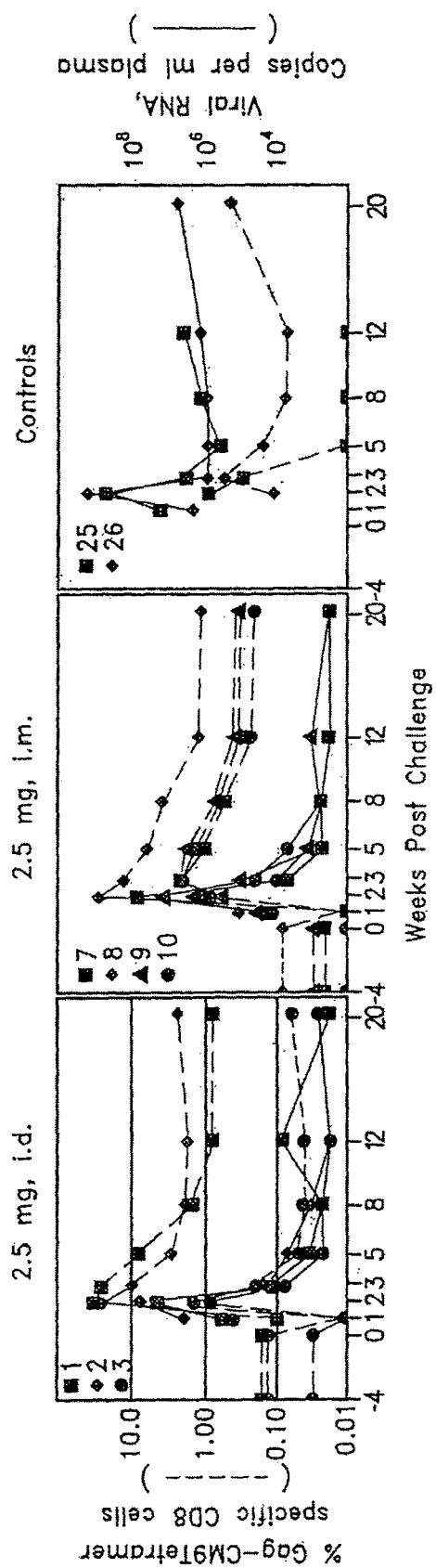
FIG. 9. Postchallenge T cell responses in vaccine and control groups. (A) Temporal tetramer⁺ cells (dashed line) and viral loads (solid line). (B) Intracellular cytokine assays for IFN-γ production in response to stimulation with the Gag-CM9 peptide at two weeks after challenge. This ex vivo assay allows evaluation of the functional status of the peak postchallenge tetramer⁺ cells displayed in FIG. 7A. (C) Proliferation assay at 12 weeks after challenge. Gag-Pol-Env (open bars) and Gag-Pol (hatched bars) produced by transient transfections were used for stimulation. Supernatants from mock-transfected cultures served as control antigen. Stimulation indices are the growth of cultures in the presence of viral antigens divided by the growth of cultures in the presence of mock antigen.

Containment of the viral challenge was associated with a burst of antiviral T cells (FIGS. 7 and 9A). At one week after challenge, the frequency of tetramer$^+$ cells in the peripheral blood had decreased, potentially reflecting the recruitment of specific T cells to the site of infection (FIG. 9A). However, by two weeks after challenge, tetramer$^+$ cells in the peripheral blood had expanded to frequencies as high as, or higher than, after the rMVA booster (FIGS. 7 and 9A). The majority of the tetramer$^+$ cells produced IFN-γ in response to a 6-hour peptide stimulation (FIG. 9B) (S. L. Waldrop et al. 1997 *J Clin Invest* 99:1739) and did not have the "stunned" IFN-γ negative phenotype sometimes observed in viral infections (F. Lechner et al. 2000 *J Exp Med* 191:1499).

For intracellular cytokine assays, about $1 \times 10^6$ PBMC were stimulated for 1 hour at 37° C. in 5 ml polypropylene tubes with 100 µg of Gag-CM9 peptide (CTPYDINQM) (SEQ ID NO: 6) per milliliter in a volume of 100 µl RPMI containing 0.1% bovine serum albumin (BSA) and 1 µg of antibody to human CD28 and 1 µg of antibody to human CD49d (Pharmingen, San. Diego, Calif.) per milliliter. Then, 900 of RPMI containing 10% FBS and monensin (10 µg/ml) was added, and the cells were cultured for an additional 5 hrs at 37° C. at an angle of 5° under 5% $CO_2$. Cells were surface stained with antibodies to CD8 conjugated to erCP (clone SK1, Becton Dickinson) at 8° to 10° C. for 30 min, washed twice with cold PBS containing 2% PBS, and fixed and permeabilized with CYTOFIX/CYTOPERM™ solution (Pharmingen, San Diego, Calif.). Cells were then incubated with antibodies to human CD3 (clone FN-18; Biosource International, Camarillo, Calif.) and IFN-γ (Clone B27; Pharmingen) conjugated to FITC and phycoerythrin, respectively, in Perm wash solution (Pharmingen) for 30 min at 4° C. Cells were washed twice with Perm wash, once with plain. PBS, and resuspended in 1% paraformaldehyde in PBS. About 150,000 lymphocytes were acquired on the FACScaliber and analyzed with FloJo software.

The postchallenge burst of T cells contracted concomitant with the decline of the viral load. By 12 weeks after challenge, virus-specific T cells were present at about one-tenth of their peak height (FIGS. 7A and 9A). In contrast to the vigorous secondary response in the vaccinated animals, the naive animals mounted a modest primary response (FIGS. 7B and 9A). Tetramer$^+$ cells peaked at less than 1% of total CD8 cells (FIG. 9A), and IFN-γ-producing ELISPOTs were present at a mean frequency of about 300 as opposed to the much higher frequencies of 1000 to 6000 in the vaccine groups (FIG. 7B) ($P<0.05$).

Figure 9B:
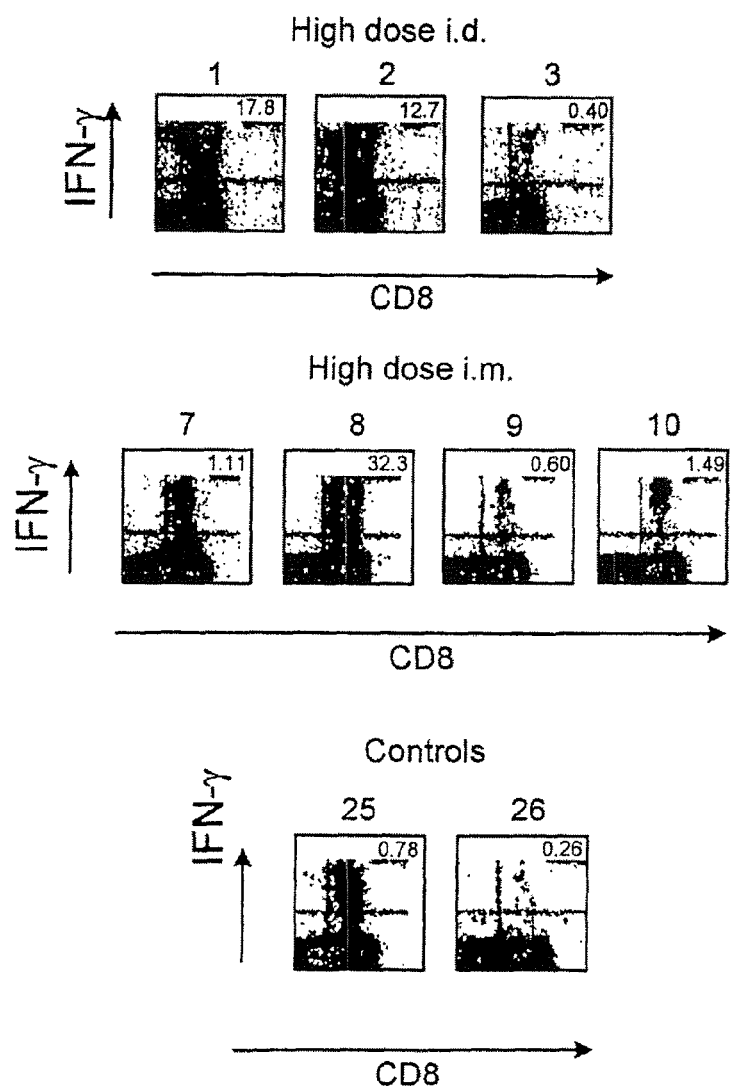

The tetramer$^+$ cells in the control group, like those in the vaccine group, produced IFN-γ after peptide stimulation (FIG. 9B). By 12 weeks after challenge, three of the four controls had undetectable levels of IFN-γ-producing ELISPOTs. This rapid loss of antiviral T cells in the presence of high viral loads may reflect the lack of CD4 help.

Figure 9C:
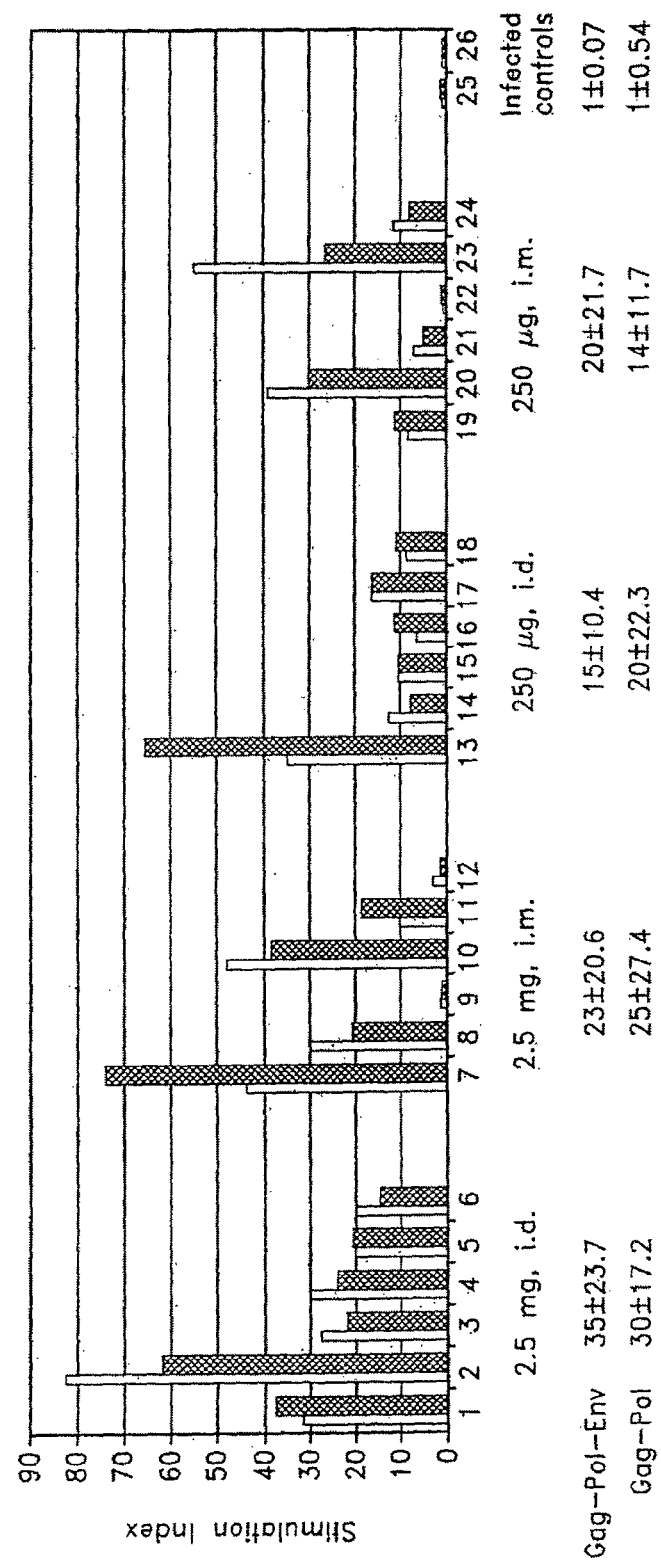

T cell proliferative responses demonstrated that virus-specific CD4 cells had survived the challenge and were available to support the antiviral immune response (FIG. 9C).

About 0.2 million PBMC were stimulated in triplicate for 5 days with the indicated antigen in 200 µl of RPMI at 37° C. under 5% $CO_2$. Supernatants from 293T cells transfected with DNA expressing either SHIV-89.6 Gag and Pol or SHIV-89.6 Gag, Pol and Env were used directly as antigens (final concentration of ~0.5 µg of p27 Gag per milliliter). Supernatants from mock DNA (vector alone)-transfected cells served as negative controls. On day six, cells were pulsed with 1 µCi of tritiated thymidine per well for 16 to 20 hours. Cells were harvested with an automated cell harvester (TOMTEC, Harvester 96, Model 1010, Hamden, Conn.) and counted with a Wallac 1450 MICROBETA Scintillation counter (Gaithersburg, Md.). Stimulation indices are the counts of tritiated thymidine incorporated in PBMC stimulated with 89.6 antigens divided by the counts of tritiated thymidine incorporated by the same PBMC stimulated with mock antigen.

At 12 weeks after challenge, mean stimulation indices for Gag-Pol-Env or Gag-Pol proteins ranged from 35 to 14 in the vaccine groups but were undetectable in the control group. Consistent with the proliferation assays, intracellular cytokine assays demonstrated the presence of virus-specific CD4 cells in vaccinated but not control animals. The overall rank order of the vaccine groups for the magnitude of the proliferative response was 2.5 mg i.d.>2.5 mg i.m.>250 µg i.d.>250 µg i.m.

Figure 10D:
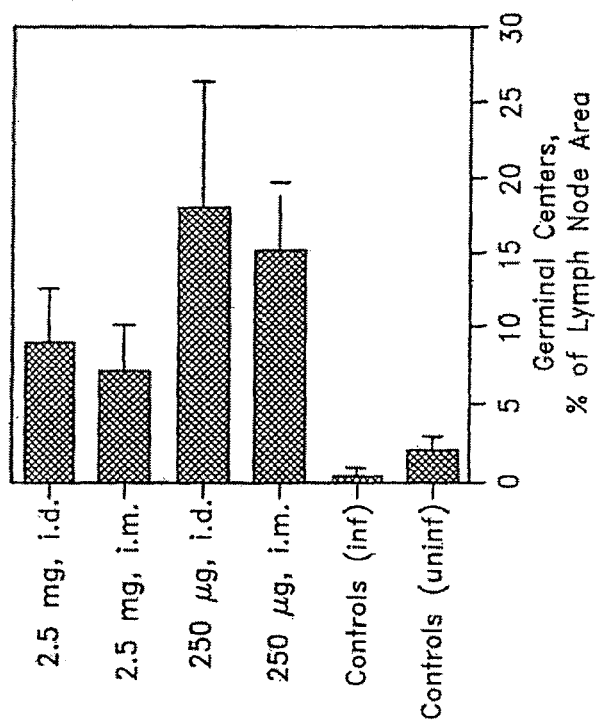
FIG. 10. Lymph node histomorphology at 12 weeks after challenge. (A) Typical lymph node from a vaccinated macaque showing evidence of follicular hyperplasia characterized by the presence of numerous secondary follicles with expanded germinal centers and discrete dark and light zones. (B) Typical lymph node from an infected control animal showing follicular depletion and paracortical lymphocellular atrophy. (C) A representative lymph node from an age-matched, uninfected macaque displaying nonreactive germinal centers. (D) The percentage of the total lymph node area occupied by germinal centers was measured to give a non-specific indicator of follicular hyperplasia. Data for uninfected controls are for four age-matched rhesus macaques.
Figure 11A:
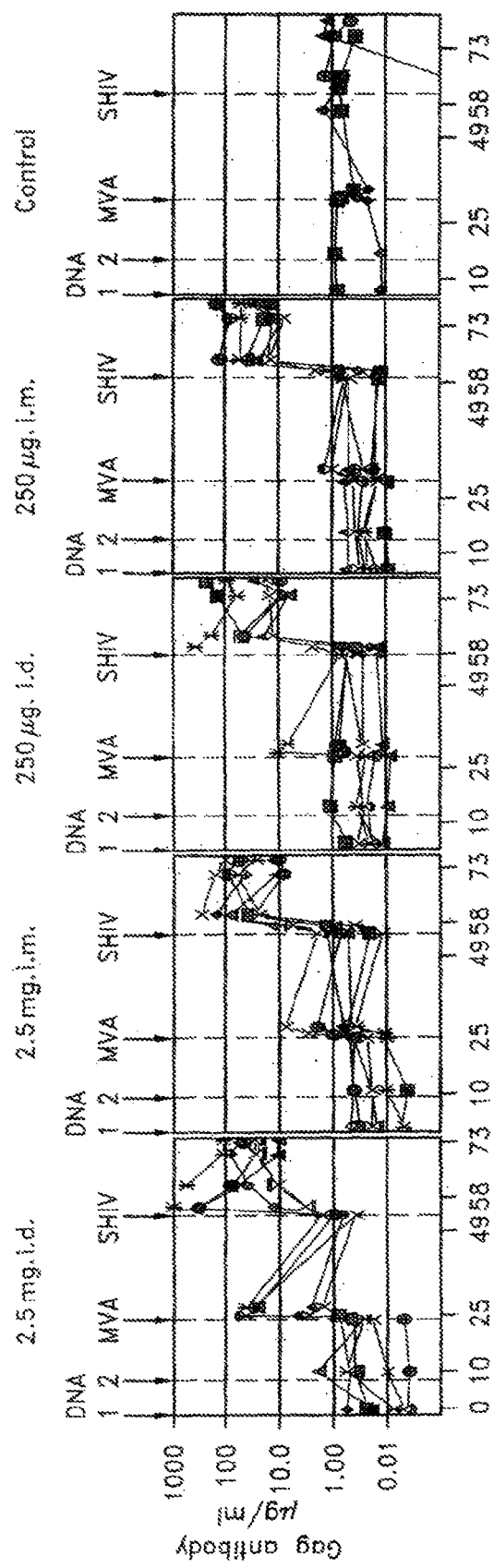
FIG. 11. Temporal antibody responses. Micrograms of total Gag (A) or Env (B) antibody were determined with ELISAs. The titers of neutralizing antibody for SHIV-89.6 (C) and SHIV-89.6P (D) were determined with MT-2 cell killing and neutral red staining (D. C. Montefiori et al. 1988 *J Clin Microbial* 26:231). Titers are the reciprocal of the serum dilution giving 50% neutralization of the indicated viruses grown in human PBMC. Symbols for animals are the same as in FIG. 8.
Figure 11B:
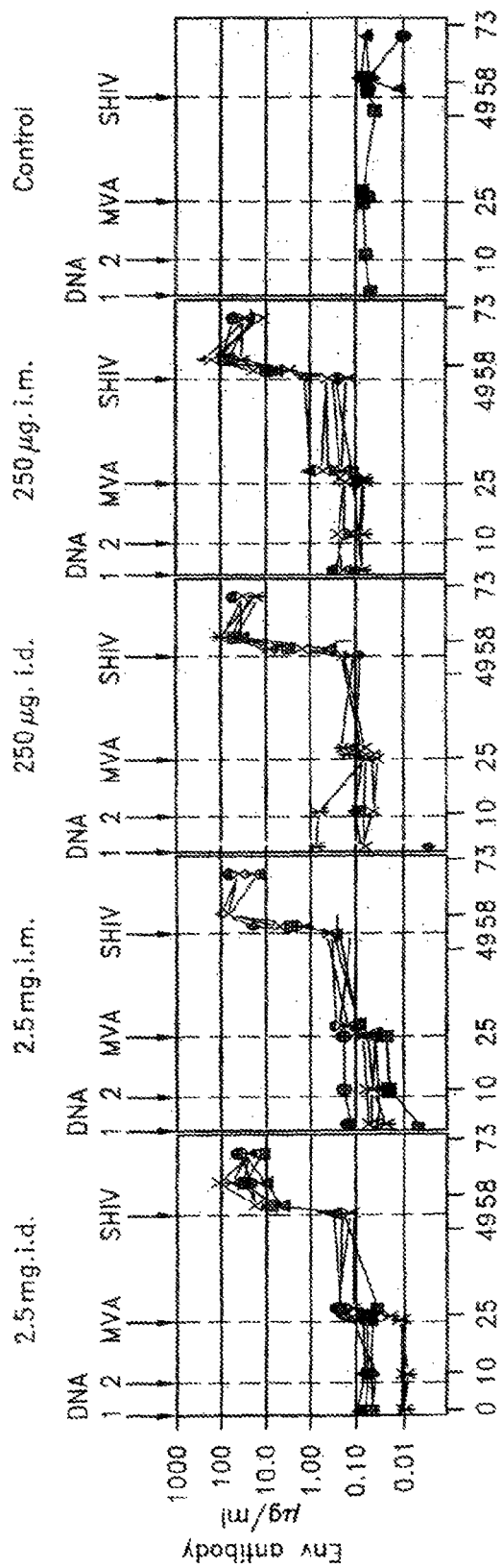
Figure 11C:
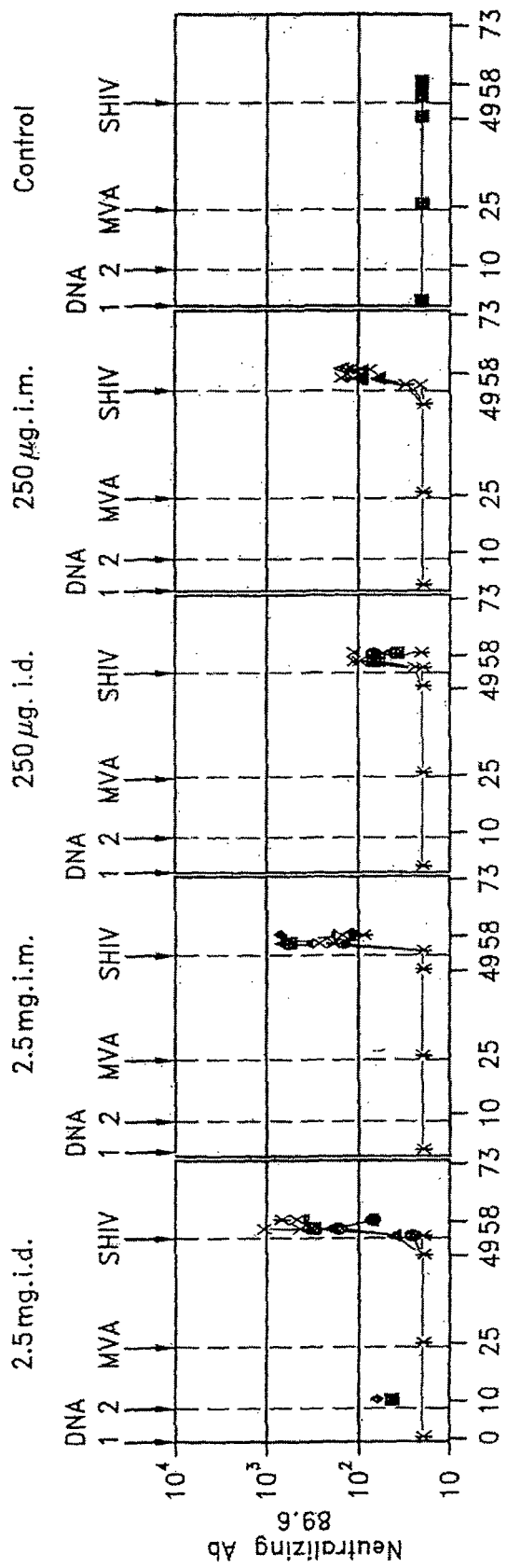
Figure 11D:
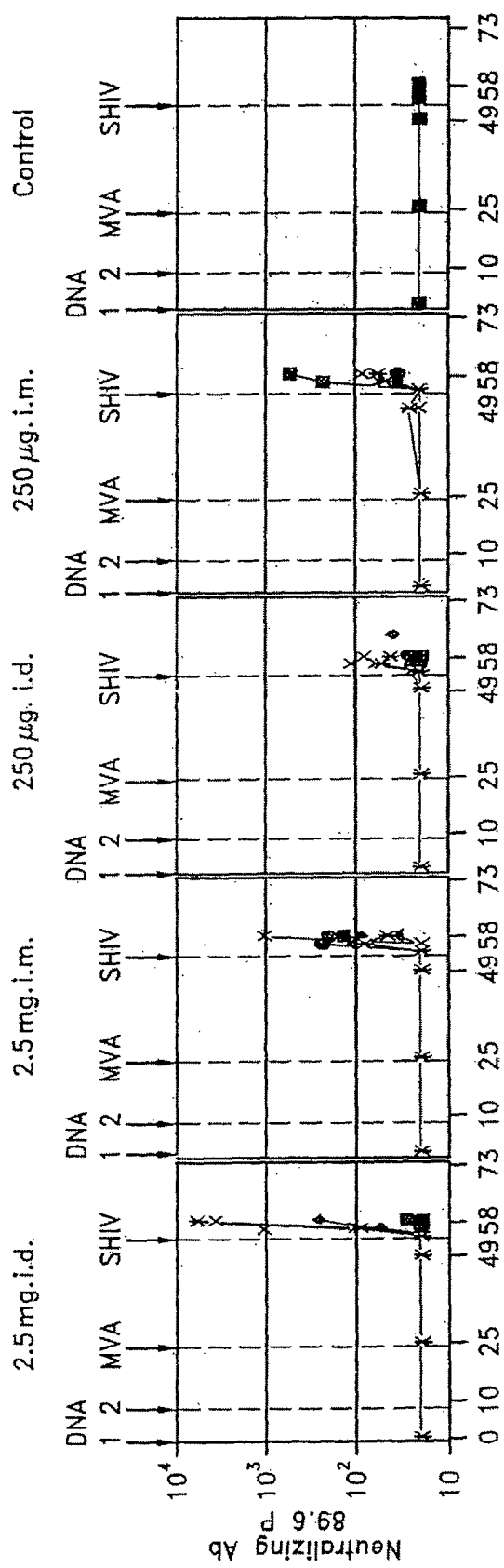

At 12 weeks after challenge, lymph nodes from the vaccinated animals were morphologically intact and responding to the infection, whereas those from the infected controls had been functionally destroyed (FIG. 10). Nodes from vaccinated animals contained large numbers of reactive secondary follicles with expanded germinal centers and discrete dark and light zones (FIG. 10A). By contrast, lymph nodes from the non-vaccinated control animals showed follicular and paracortical depletion (FIG. 10B), while those from unvaccinated and unchallenged animals displayed normal numbers of minimally reactive germinal centers (FIG. 10C). Germinal centers occupied <0.05% of total lymph node area in the infected controls, 2% of the lymph node area in the uninfected controls, and up to 18% of the lymph node area in the vaccinated groups (FIG. 10D). More vigorous immune reactivity in the low-dose than the high-dose DNA-primed animals was suggested by more extensive germinal centers in the low dose group (FIG. 10D). At 12 weeks after challenge, in situ hybridization for viral RNA revealed rare virus-expressing cells in lymph nodes from 3 of the 24 vaccinated macaques, whereas virus-expressing cells were readily detected in lymph nodes from each of the infected control animals. In the controls, which had undergone a profound depletion in CD4 T cells, the cytomorphology of infected lymph node cells was consistent with a macrophage phenotype.

The prime/boost strategy raised low levels of antibody to Gag and undetectable levels of antibody to Env (FIG. 11). Postchallenge, antibodies to both Env and Gag underwent anamnestic responses with total Gag antibody reaching heights approaching 1 mg/ml and total Env antibody reaching heights of up to 100 µg/ml.

Enzyme-linked immunosorbent assays (ELISAs) for total antibody to Gag used bacterially produced SIV gag p27 to coat wells (2 µg per milliliter in bicarbonate buffer). ELISAs for antibody to Env antibody used 89.6 Env produced in transiently transfected 293T cells and captured with sheep antibody against Env (catalog number 6205; International Enzymes, Fairbrook Calif.). Standard curves for Gag and Env ELISAs were produced with serum from a SHIV-89.6-infected macaque with known amounts of immunoglobulin G (IgG) specific for Gag or Env. Bound antibody was detected with peroxidase-conjugated goat antibody to macaque IgG (catalog #YNGMOIGGFCP; Accurate Chemical, Westbury, N.Y.) and TMB substrate (Catalog #T3405; Sigma. St. Louis, Mo.). Sera were assayed at threefold dilutions in duplicate wells. Dilutions of test sera were performed in whey buffer (4% whey and 0.1% tween 20 in 1×PBS). Blocking buffer consisted of whey buffer plus 0.5% nonfat dry milk. Reactions were stopped with 2M $H_2SO_4$ and the optical density read at 450 nm. Standard curves were fitted and sample concentrations were interpolated as µg of antibody per ml of serum using SOFTmax 2.3 software (Molecular Devices, Sunnyvale, Calif.).

By 2 weeks after challenge, neutralizing antibodies for the 89.6 immunogen, but not the SHIV-89.6P challenge, were present in the high-dose DNA-primed groups (geometric mean titers of 352 in the i.d. and 303 in the i.m. groups) (FIG. 11C) (D. C. Montefiori et al. 1988 *J Clin Microbiol* 26:231). By 5 weeks after challenge, neutralizing antibody to 89.6P had been generated (geometric mean titers of 200 in the high-dose i.d. and 126 in the high-dose i.m. group) (FIG. 11D) and neutralizing antibody to 89.6 had started to decline. By 16 to 20 weeks after challenge, antibodies to Gag and Env had fallen in most animals.

Our results demonstrate that a multiprotein DNA/MVA vaccine can raise a memory immune response capable of controlling a highly virulent mucosal immunodeficiency virus challenge. Our levels of viral control were more favorable than have been achieved Using only DNA (M. A. Egan et al. 2000 *J Virol* 74:7485) or rMVA vaccines (I. Ourmanov et al. 2000 *J Virol* 74:2740) and were comparable to those obtained for DNA immunizations adjuvanted with interleukin-2 (D. H. Barouch et al. 2000 *Science* 290:486). All of these previous studies have used more than three vaccine inoculations, none have used mucosal challenges, and most have challenged at peak effector responses and not allowed a prolonged post vaccination period to test for "long term" efficacy.

The dose of DNA had statistically significant effects on both cellular and humoral responses (P<0.05), whereas the route of DNA administration affected only humoral responses. Intradermal DNA delivery was about 10 times more effective than i.m. inoculations for generating antibody to Gag (P=0.02). Neither route nor dose of DNA appeared to have a significant effect on protection. At 20 weeks after challenge, the high-dose DNA-primed animals had slightly lower geometric mean levels of viral RNA ($7 \times 10^2$ and $5 \times 10^2$) than the low-dose DNA-primed animals ($9 \times 10^2$ and $1 \times 10^3$).

The DNA/MVA vaccine controlled the infection, rapidly reducing viral loads to near or below 1000 copies of viral RNA per milliliter of blood. Containment, rather than prevention of infection, affords the opportunity to establish a chronic infection (H. L. Robinson et al. 1999 *Nat Med* 5:526). By rapidly reducing viral loads, a multiprotein DNA/MVA vaccine will extend the prospect for long-term non-progression and limit HIV transmission. (J. W. Mellors et al. 1996 *Science* 272:1167; T. C. Quinn et al. 2000 *N Engl J Med* 342:921).

EXAMPLE 2

MVA Expressing Modified HIV Env, Gag, and Pol Genes

This disclosure describes the construction of a modified vaccinia Ankara (MVA) recombinant virus, MVA/HIV clade B recombinant virus expressing the HIV strain ADA env and the HXB2 gag pol (MVA/HIV ADA env+HXB2 gag pol). For amplification, the lab name of MVA/HIV 48 will be used, which denotes the plasmid from which the construct comes.

The HIV gag-pol genes were derived from the Clade B infectious HXB2 virus. The gag-pol gene was truncated so that most of the integrase coding sequences were removed and amino acids 185, 266, and 478 were mutated to inactivate reverse transcriptase, inhibit strand transfer activity, and inhibit the RNaseH activity, respectively. The Clade B CCR5 tropic envelope gene was derived from the primary ADA isolate; TTTTTNT sequences were mutated without changing coding capacity to prevent premature transcription termination and the cytoplasmic tail was truncated in order to improve surface expression, immunogenicity, and stability of the MVA vector. The HIV genes were inserted into a plasmid transfer vector so that gag-pol gene was regulated by the modified H5 early/late vaccinia virus promoter and the env gene was regulated by the newly designed early/late Psyn II promoter to provide similar high levels of expression. A self-deleting GUS reporter gene was included to allow detection and isolation of the recombinant virus. The HIV genes were flanked by MVA sequences to allow homologous recombination into the deletion 3 site so that the recombinant MVA would remain TK positive for stability and high expression in resting cells. The recombinant MVA was isolated and shown to express abundant amounts of gag-pol-env and to process gag. Production of HIV-like particles was demonstrated by centrifugation and by electron microscopy. The presence of env in the HIV-like particles was demonstrated by immuno-electron microscopy.

Table of Sequences

| Description | SEQ ID NO | FIG. NO |
|---|---|---|
| pLW-48 | 1 | 14 |
| pLW-48 | 1 | 15 |
| Psyn II promoter | 2 | 15 |
| ADA envelope truncated | 3 | 15 |
| PmH5 promoter | 4 | 15 |
| HXB2 gag pol | 5 | 15 |

Plasmid Transfer Vector

Figure 16:
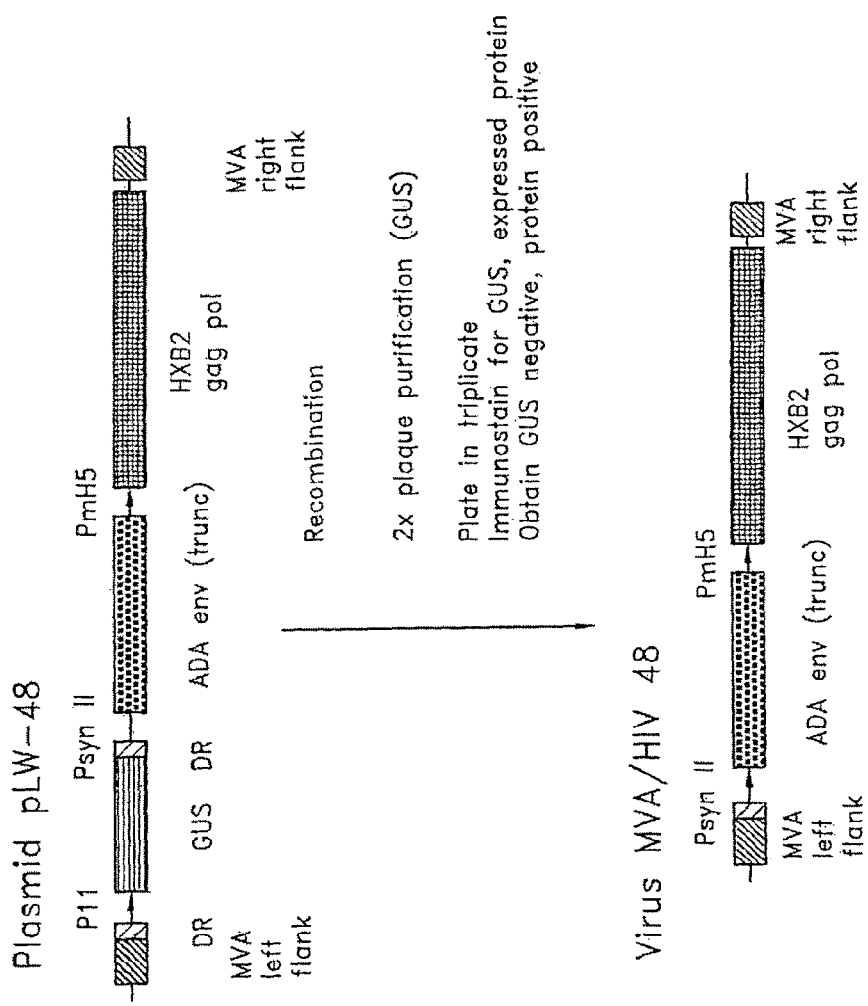
FIG. 16. Plasmid transfer vector pLW-48 and making MVA recombinant virus MVA/HIV 48.

The plasmid transfer vector used to make the MVA recombinant virus, pLW-48, (FIG. 16) by homologous recombination was constructed as follows:

1. From the commercially obtained plasmid, pGem-4Z (Promega), flanking areas on either side of deletion III, designated flank 1 and flank 2, containing 926 and 520 base pairs respectively, were amplified by PCR from the MVA stains of vaccinia virus. Within these flanks, a promoter, the mH5, which had been modified from the originally published sequence by changing two bases that had been shown by previously published work to increase the expression of the cloned gene, was added.

Figure 17:
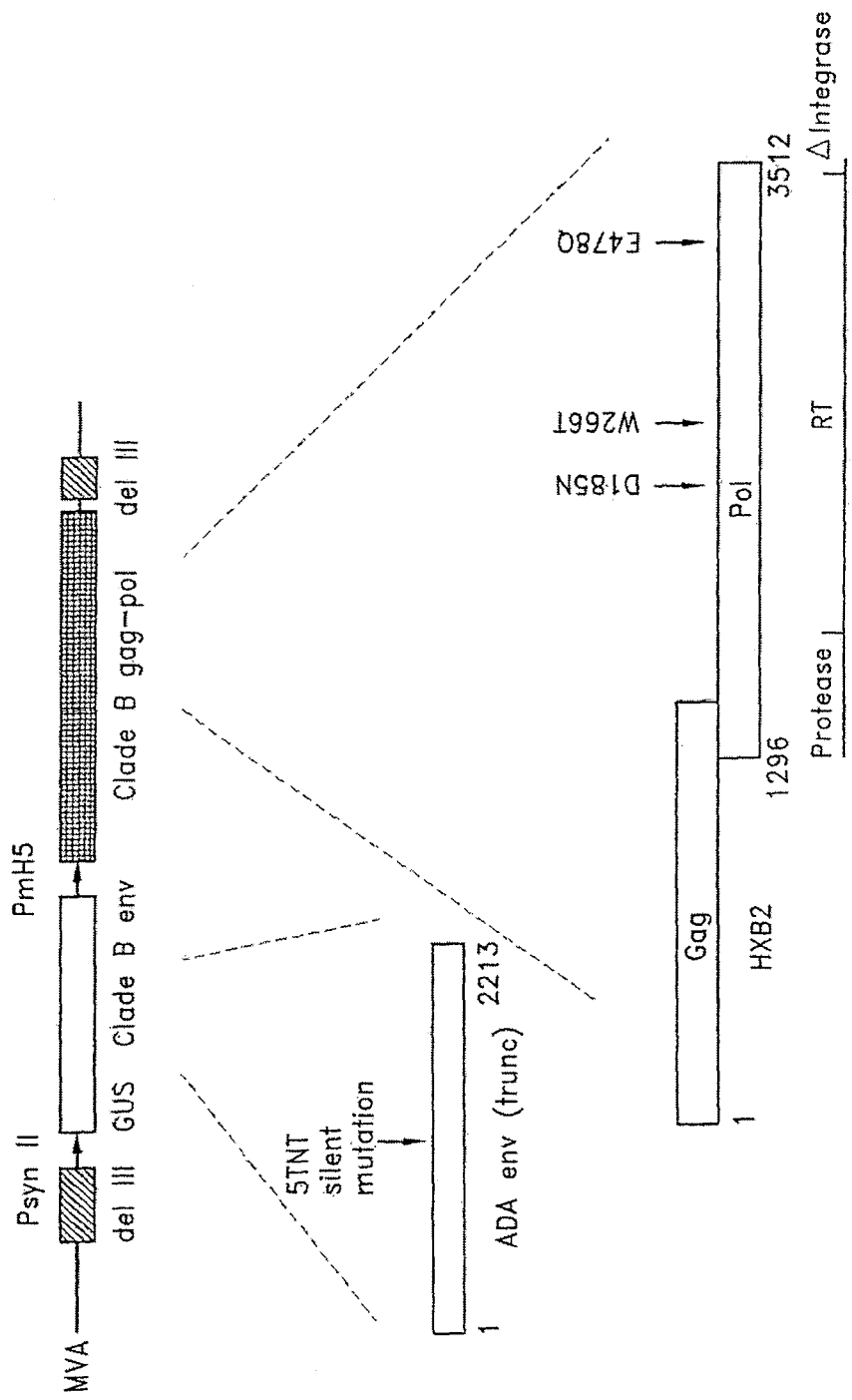
FIG. 17. A clade B gag pol.

2. A clade B gag pol (FIG. 17) was truncated so that the integrase was removed and was cloned into the plasmid so that it was controlled by the mH5 promoter. This gene contained the complete HXB2 sequence of the gag. The pol gene has reverse transcriptase safety mutations in amino acid 185 within the active site of RT, in amino acid 266 which inhibits strand transfer activity, and at amino acid 478 which inhibits the RNaseH activity. In addition, the integrase gene was deleted past EcoRI site.

3. A direct repeat of 280 basepairs, corresponding to the last 280 base pairs of MVA flank 1, was added after flank 1.

4. The p11 promoter and GUS reporter gene were added between the two direct repeats of flank 1 so that this screening marker could initially be used for obtaining the recombinant virus, yet deleted out in the final recombinant virus (Scheiflinger, F. et al. 1998 *Arch Virol* 143:467-474; Carroll, M. W. and B. Moss 1995 *BioTechniques* 19:352-355).

5. A new promoter, Psyn II, was designed to allow for increased expression of the ADA env. The sequence of this new early/late promoter is given in FIG. 18.

6. A truncated version of the ADA envelope with a silent 5TNT mutation was obtained by PCR and inserted in the plasmid under the control of the Psyn II promoter. The envelope was truncated in the cytoplasmic tail of the gp41 gene, deleting 115 amino acids of the cytoplasmic tail. This truncation was shown to increase the amount of envelope protein on the surface of infected cells and enhance immunogenicity of the envelope protein in mice, and stability of the recombinant virus in tissue culture.

Recombinant MVA Construction

1. MVA virus, which may be obtained from ATCC Number VR-1508, was plaque purified three times by terminal dilutions in chicken embryo fibroblasts (CEF), which were made from 9 day old SPF Premium SPAFAS fertile chicken eggs, distributed by B and E Eggs, Stevens, Pa.

2. Secondary CEF cells were infected at an MOI of 0.05 of MVA and transfected with 2 µg of pLW-48, the plasmid described above. Following a two day incubation at 37° C., the virus was harvested, frozen and thawed 3×, and plated out on CEF plates.

3. At 4 days, those foci of infection that stained blue after addition of X-gluc substrate, indicating that recombination had occurred between the plasmid and the infecting virus, were picked and inoculated on CEF plates. Again, those foci that stained blue were picked.

4. These GUS containing foci were plated out in triplicate and analyzed for GUS staining (which we wanted to now delete) and ADA envelope expression. Individual foci were picked from the 3rd replicate plates of those samples that had about equal numbers of mixed populations of GUS staining and nonstaining foci as well as mostly envelope staining foci.

5. These foci were again plated out in triplicate, and analyzed the same way. After 5 passages, a virus was derived which expressed the envelope protein but which had deleted the GUS gene because of the double repeat. By immunostaining, this virus also expressed the gag pol protein.

Characterization of MVA Recombinant Virus, MVA/HIV 48

1. Aliquots of MVA/HIV 48 infected cell lysates were analyzed by radioimmunoprecipitation and immunostaining with monoclonal antibodies for expression of both the envelope and gag pol protein. In both of these tests, each of these proteins was detected.

2. The recombinant virus was shown to produce gag particles in the supernatant of infected cells by pelleting the $^{35}$S-labeled particles on a 20% sucrose cushion.

3. Gag particles were also visualized both outside and budding from cells as well as within vacuoles of cells in the electron microscope in thin sections. These gag particles had envelope protein on their surface.

Unless otherwise indicated, all nucleotide sequences determined by sequencing a DNA molecule herein were determined using an automated DNA sequencer, and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Summary

In summary, we have made a recombinant MVA virus, MVA/HIV 48, which has high expression of the ADA truncated envelope and the HXB2 gag pol. The MVA recombinant virus is made using a transiently expressed GUS marker that is deleted in the final virus. High expression of the ADA envelope is possible because of a new hybrid early/late promoter, Psyn II. In addition, the envelope has been truncated because we have shown truncation of the envelope enhances the amount of protein on the surface of the infected cells, and hence enhances immunogenicity; stability of the recombinant is also enhanced. The MVA recombinant makes gag particles which has been shown by pelleting the particles through sucrose and analyzing by PAGE. Gag particles with envelope protein on the surface have also been visualized in the electron microscope.

EXAMPLE 3

Additional Modified or Synthetic Promoters Designed for Gene Expression in MVA Or Other Poxviruses Additional modified or synthetic promoters were designed for gene expression in MVA or other poxviruses. Promoters were modified to allow expression at early and late times after infection and to reduce possibility of homologous recombination between identical sequences when multiple promoters are used in same MVA vector. Promoters are placed upstream of protein coding sequence.

m7.5 promoter (SEQ ID NO: 10):
CGCTTTTTATAGTAAGTTTTTCACCCATAAATAATAAATACAATAATTA

ATTTCTCGTAAAAATTGAAAAACTATTCTAATTTATTGCACGGT

Psyn II promoter (SEQ ID NO: 2):
TAAAAAATGAAAAAATATTCTAATTTATAGGACGGTTTTGATTTTCTTT

TTTTCTATGCTATAAATAATAAATA

Psyn III promoter (SEQ ID NO: 11):
TAAAAATTGAAAAAATATTCTAATTTATAGGACGGTTTTGATTTTCTTT

TTTTCTATACTATAAATAATAAATA

Psyn IV promoter (SEQ ID NO: 12):
TAAAAATTGAAAAACTATTCTAATTTATAGGACGGTTTTGATTTTCTTT

TTTTCTATACTATAAATAATAAATA

PsynV promoter (SEQ ID NO: 13):
AAAAAATGATAAAGTAGGTTCAGTTTTATTGCTGGTTTAAAATCACGCT

TTCGAGTAAAAACTACGAATATAAAT

EXAMPLE 4

Tables A-F

Table A

MVA/48 Immunization—Guinea Pigs

Groups of guinea pigs were immunized at days 0 and 30 with 1×10$^8$ infectious units of MVA/48 by either the intramuscular (IM) or intradermal (ID) route. As a control another group was immunized IM with the same dose of non-recombinant MVA. Sera taken before as well as after each immunization was analyzed for neutralizing activity against HIV-1-MN. Titers are the reciprocal serum dilution at which 50% of MT-2 cells were protected from virus-induced killing. Significant neutralizing activity was observed in all animals after the second immunization with MVA/48 (day 49).

Table B

Frequencies of HIV-1 Gag-Specific T Cells Following Immunization of Mice with MVA/48

Groups of BalbC mice were immunized at days 0 and 21 with 1×10$^7$ infectious units of MVA/48 by one of three, routes: intraperitoneal (IP), intradermal (ID), or intramuscular (IM). A control group was immunized with non-recombinant MVA. At 5 weeks after the last immunization, splenocytes were prepared and stimulated in vitro with an immunodominant peptide from HIV-1 p24 for 7 days. The cells were then mixed either with peptide-pulsed P815 cells or with soluble peptide. Gamma interferon-producing cells were enumerated in an ELISPOT assay. A value of >500 was assigned to wells containing too many spots to count. Strong T cell responses have been reported in mice immunized IP with other viruses. In this experiment, IP immunization of mice with MVA/48 elicited very strong HIV-1 gag-specific T cell responses.

Table C

DNA Prime and MVA/48 Boost—Total Elispots Per Animal

Ten rhesus macaques were primed (weeks 0 and 8) with a DNA vaccine expressing HIV-1 antigens including Ada envelope and HXB2 gagpol. At week 24 the animals were boosted intramuscularly with $1 \times 10^8$ infectious units of MVA/48. Fresh peripheral blood mononuclear cells (PBMC) were analyzed for production of gamma interferon in an ELISPOT assay as follows: PBMC were incubated for 30-36 hours in the presence of pools of overlapping peptides corresponding to the individual HIV-1 antigens in the vaccines. The total number of gamma interferon-producing cells from each animal is shown in the table. T cell responses to DNA vaccination were limited (weeks 2-20). However, boosting with MVA/48 resulted in very strong HIV-1-specific T cell responses in all animals (week 25).

Table D

Antibody Response Following Immunization of Macaques with MVA/SHIV KB9

Groups of rhesus macaques were immunized with $2 \times 10^8$ infectious units of MVA/SHIV-KB9 at weeks 0 and 4 by one of several routes: Tonsilar, intradermal (ID), or intramuscular (IM). Another group was immunized with non-recombinant MVA using the same routes. Serum samples from 2 weeks after the second immunization were analyzed for binding to KB9 envelope protein by ELISA and for neutralization of SHIV-89.6P and SHIV-89.6. In the ELISA assay, soluble KB9 envelope protein was captured in 96 well plates using an antibody to the C-terminus of gp120. Serial dilutions of sera were analyzed and used to determine the endpoint titers. Neutralization of SHIV-89.6P and SHIV-89.6 was determined in an MT-2 cell assay. Titers are the reciprocal serum dilution at which 50% of the cells were protected from virus-induced killing. In in vitro neutralization assays, SHIV-89.6P and SHIV-89.6 are heterologous, i.e. sera from animals infected with one of the viruses does not neutralize the other virus. Thus, two immunizations with MVA/SHIV-KB9 elicited good ELISA binding antibodies in all animals and neutralizing antibodies to the homologous virus (SHIV-89.6P) in some animals. In addition, heterologous neutralizing antibodies were observed in a subset of animals.

Table E

Frequencies of gag CM-9-Specific CD3/CD8 T Cells Following Immunization of Macaques with MVA/SHIV-KB9

Groups of MamuA*01 positive rhesus macaques were immunized with $2 \times 10^8$ infectious units of MVA/SHIV-KB9 at weeks 0 and 4 by one of several routes: tonsilar, intradermal (ID), or intramuscular IM). Another group was immunized with non-recombinant MVA. The frequencies of CD3+/CD8+ T cells that bound tetrameric complex containing the SIV gag-specific peptide CM9 were determined by flow cytometry at various times after each immunization. Time intervals were as follows: 1a, 1b, and 1d were one, two, and four weeks after the first immunization, respectively; 2a, 2b, 2c, and 2d were one, two, three, and twelve weeks after the second immunization, respectively. Values above background are shown in bold face. Strong SIV gag-specific responses were observed after a single immunization with MVA/SHIV-KB9 in all immunized animals. Boosting was observed in most animals following the second immunization. In addition, measurable tetramer binding was still found twelve weeks after the second immunization.

Table F

Frequencies of Specific T Cells Following Immunization of Macaques with MVA/SHIV KB9

Groups of macaques were immunized with MVA/SHIV-KB9 as described above. MVA/SHIV-KB9 expresses 5 genes from the chimeric virus, SHIV-89.6P: envelope, gag, polymerase, tat, and nef. Thus, the frequencies of T cells specific for each of the 5 antigens was analyzed using pools of peptides corresponding to each individual protein. Fresh PBMC were stimulated with pools of peptides for 30-36 hours in vitro. Gamma interferon-producing cells were enumerated in an ELISPOT assay. The total number of cells specific for each antigen is given as "total # spots". In addition, the number of responding animals and average # of spots per group is shown. PBMC were analyzed at one week after the first immunization (1a) and one week after the second immunization (2a). Another group of 7 animals was immunized with non-recombinant MVA. In these animals, no spots above background levels were detected. Thus, a single immunization with MVA/SHIV-KB9 elicited strong SHIV-specific T cell responses in all animals. Gag and envelope responses were the strongest; most animals had responses to gag, all animals had responses to envelope. The Elispot responses were also observed after the second immunization with MVA/SHIV-KB9, albeit at lower levels. At both times, the rank order of responses was: tonsilar>ID>IM. We show good immune response to nef and some immune response to tat.

TABLE A

| | MVA/48 immunization—guinea pigs | | | | | | |
| | HIV-MN neutralizing antibody—reciprocal titer | | | | | | |
| Animal # | Group | Route | day 0 | Day 4 MVA #1 | day 30 | day 33 MVA#2 | day 49 |
| --- | --- | --- | --- | --- | --- | --- | --- |
| 885 | MVA | I.M. | <20 | I.M. | 31 | I.M. | 24 |
| 891 | " | " | <20 | " | 85 | " | <20 |
| 882 | MVA/48 | I.M. | <20 | I.M. | <20 | I.M. | 5,524 |
| 883 | " | " | <20 | " | 68 | " | 691 |
| 886 | " | " | <20 | " | <20 | " | 4,249 |
| 890 | " | " | <20 | " | 180 | " | 89 |
| 879 | MVA/48 | I.D. | <20 | I.D. | <20 | I.D. | 817 |
| 881 | " | " | <20 | " | <20 | " | 234 |
| 888 | " | " | <20 | " | 24 | " | 112 |
| 889 | " | " | <20 | " | 22 | " | 376 |

TABLE B

Frequencies of HIV-gag-specific T cells following immunization of mice with MVA/48

| Group | P815 cells + gag peptide | | gag peptide | | no stimulation | |
|---|---|---|---|---|---|---|
| MVA control | 0 | 2 | 0 | 4 | 1 | 2 |
| MVA/48 (IP) | >500 | >500 | >500 | >500 | 8 | 8 |
| MVA/48 (ID) | 12 | 5 | 49 | 33 | 4 | 2 |
| MVA/48 (IM) | 22 | 18 | 66 | 49 | 12 | 8 |

TABLE C

DNA prime and MVA/48 boost
Total ELISPOTS per Animal

| | WEEKS | | | | | | |
|---|---|---|---|---|---|---|---|
| Animal # | -2 | 2 | 6 | 10 [2] | 14 [2] | 20 [2] | 25 [2] |
| RLw | 4 | 731* | < | 47 | 43 | 50 | 3905 |
| RVl | 5 | 997* | < | < | < | 8 | 205 |
| Roa | < [1] | < | 1 | < | < | < | 245 |
| RHc | < | < | < | < | < | < | 535 |
| Ryl | < | < | < | < | < | < | 4130 |
| RQk | < | 46 | < | < | < | < | 630 |
| RDr | < | < | < | 14 | < | < | 1965 |
| RZc | < | 5 | < | 58 | < | < | 925 |
| RSf | < | 1.18 | < | < | < | 20 | 5570 |
| Ras | < | 69 | < | < | < | < | 1435 |
| Total | 9 | 1966 | 1 | 119 | 43 | 78 | 19545 |
| Geo Mean | 4.5 | 105.3 | 1.0 | 33.7 | 43.0 | 20.0 | 1147.7 |

DNA primes were at 0 and 8 weeks and MVA/48 boost was at 24 weeks
[1] < = Background (2x the number of ELISPOTs in the unstimulated control + 10)
[2] Costimulatory antibodies were added to the ELISPOT incubations
*Animals from this bleed date exhibited higher than usual ELISPOTs.

TABLE D

Antibody response following immunization of macaques with MVA/SHIV KB9

| Animal # | Route | KB9 env ELISA titer | KB9 env elisa average | KB9 env elisa std dev. | SHIV-89.6 Nab titer | SHIV-89.6P Nab titer | SHIV-89.6 # pos animals | SHIV-89.6P # pos animals |
|---|---|---|---|---|---|---|---|---|
| 598 | tonsil | 25,600 | 31,086 | 20,383 | <20 | <20 | 3 | 2 |
| 601 | " | 51,200 | | | <20 | <20 | | |
| 606 | " | 25,600 | | | <20 | <20 | | |
| 642 | " | 51,200 | | | 75 | 31 | | |
| 646 | " | 51,200 | | | 61 | 48 | | |
| 653 | " | 6,400 | | | <20 | <20 | | |
| 654 | " | 6,400 | | | 22 | <20 | | |
| 602 | i.d. | 25,600 | 18,800 | 15,341 | 38 | <20 | 2 | 4 |
| 604 | " | 12,800 | | | <20 | 262 | | |
| 608 | " | 3,200 | | | 20 | 66 | | |
| 637 | " | 12,800 | | | <20 | 35 | | |
| 638 | " | 51,200 | | | <20 | <20 | | |
| 645 | " | 25,600 | | | <20 | <20 | | |
| 647 | " | 12,800 | | | 32 | 162 | | |
| 650 | " | 6,400 | | | <20 | <20 | | |
| 599 | i.m. | 6,400 | 17,000 | 16,516 | <20 | <20 | 0 | 3 |
| 600 | " | 6,400 | | | <20 | 29 | | |
| 609 | " | 6,400 | | | <20 | <20 | | |
| 639 | " | 51,200 | | | <20 | 85 | | |
| 640 | " | 12,800 | | | <20 | <20 | | |
| 641 | " | 25,600 | | | <20 | 41 | | |
| 649 | " | 1,600 | | | <20 | <20 | | |
| 651 | " | 25,600 | | | 20 | <20 | | |
| 603 | Control | <100 | <100 | | <20 | <20 | 0 | 0 |
| 605 | " | <100 | | | <20 | <20 | | |
| 607 | " | <100 | | | <20 | <20 | | |
| 643 | " | <100 | | | <20 | <20 | | |
| 644 | " | <100 | | | <20 | <20 | | |
| 648 | " | <100 | | | <20 | <20 | | |
| 652 | " | <100 | | | <20 | <20 | | |

TABLE E

Frequencies of gag CM9—specific CD3/CD8 T cells following immunization of macaques with MVA/SHIV KB9

| Animal # | Route | Virus | pre-bleed | 1a | 1b | 1d | 2a | 2b | 2c | 2d |
|---|---|---|---|---|---|---|---|---|---|---|
| 598 | Tonsil | MVA/KB9 | 0.018 | 0.41 | 0.79 | 0.25 | 2.64 | 1.13 | 0.51 | 0.21 |
| 601 | " | " | 0.071 | 0.34 | 0.38 | 0.27 | 0.83 | 0.7 | 0.36 | 0.039 |

TABLE E-continued

Frequencies of gag CM9—specific CD3/CD8 T cells following immunization of macaques with MVA/SHIV KB9

| Animal # | Route | Virus | pre-bleed | 1a | 1b | 1d | 2a | 2b | 2c | 2d |
|---|---|---|---|---|---|---|---|---|---|---|
| 646 | " | " | 0.022 | 0.68 | 0.76 | 0.43 | 1.12 | 0.91 | 0.53 | 0.15 |
| 653 | " | " | 0.041 | 0.69 | 0.85 | 0.53 | 0.68 | 0.49 | 0.47 | 0.3 |
| 648 | " | MVA | | 0.033 | 0.039 | | 0.022 | 0.058 | 0.033 | 0.013 |
| 602 | i.d. | MVA/KB9 | 0.019 | 0.17 | 0.92 | 0.5 | 0.95 | 0.59 | 0.5 | 0.2 |
| 604 | " | " | 0.013 | 0.11 | 0.38 | 0.32 | 0.44 | 0.38 | 0.19 | 0.25 |
| 650 | " | " | 0.095 | 0.17 | 0.6 | 0.23 | 2.87 | 1.12 | 0.9 | 0.16 |
| 647 | " | " | 0.032 | 0.22 | 0.38 | 0.14 | 0.84 | 0.91 | 0.34 | 0.17 |
| 652 | " | MVA | | 0.041 | 0.038 | 0.059 | 0.025 | 0.022 | 0.026 | 0.055 |
| 599 | i.m. | MVA/KB9 | | 0.081 | 0.31 | 0.082 | | 0.12 | 0.054 | 0.11 |
| 600 | " | " | 0.034 | 0.15 | 0.41 | 0.17 | 0.29 | 0.27 | 0.16 | 0.049 |
| 649 | " | " | 0.00486 | 0.35 | 1.34 | 0.56 | 2.42 | 0.77 | 0.69 | 0.22 |
| 651 | " | " | 0.049 | 0.12 | 0.69 | 0.25 | 1.01 | 0.32 | 0.24 | 0.22 |
| 603 | " | MVA | | 0.024 | 0.087 | 0.073 | | 0.082 | 0.027 | 0.17 |

TABLE F

Frequencies of specific T cells following immunization of macaques with MVA/SHIV KB9

| Study groups | Gag specific | | | Tat specific | | | Nef specific | | | Env specific | | | Total |
|---|---|---|---|---|---|---|---|---|---|---|---|---|---|
| | # responding animals | Total # spots | average # spots | # responding animals | total # spots | average # spots | # responding animals | total # spots | average # spots | # responding animals | total # spots | Average # spots | # responding animals |
| tonsil 1a | 4/6 | 1325 | 221 | 0/6 | 0 | 0 | 3/6 | 195 | 33 | 6/6 | 8760 | 1460 | 6/6 |
| tonsil 2a | 5/6 | 1405 | 234 | 0/6 | 0 | 0 | 1/6 | 560 | 93 | 6/6 | 4485 | 748 | 6/6 |
| i.d. 1a | 7/7 | 1335 | 191 | 0/7 | 0 | 0 | 2/7 | 215 | 31 | 7/7 | 7320 | 1046 | 7/7 |
| i.d. 2a | 4/7 | 755 | 108 | 0/7 | 0 | 0 | 1/7 | 55 | 8 | 7/7 | 2700 | 386 | 7/7 |
| i.m. 1a | 7/7 | 925 | 132 | 1/7 | 60 | 9 | 3/7 | 180 | 26 | 7/7 | 5490 | 784 | 7/7 |
| i.m. 2a | 4/7 | 250 | 36 | 0/7 | 0 | 0 | 0/7 | 0 | 0 | 6/7 | 2205 | 315 | 6/7 |

While the present invention has been described in some detail for purposes of clarity and understanding, one skilled in the art will appreciate that various changes in form and detail can be made without departing from the true scope of the invention. All patents, patent applications and publications referred to above are hereby incorporated by reference.

What is claimed is:

1. A recombinant MVA virus expressing HIV-1 Gag, HIV-1 Pol lacking the integrase domain wherein the HIV-1 Pol expressed by the recombinant MVA virus has at least one amino acid change that inhibits reverse transcriptase activity, at least one amino acid change that inhibits strand transfer activity and at least one amino acid change that inhibits RNaseH activity, and at least the gp120 protein and the membrane-spanning domain and ectodomain of gp41 protein of HIV-I Env, but lacking at least 115 amino acids of the cytoplasmic domain of gp41 protein.

2. A recombinant MVA virus that expresses the HXB2 Gag/Pol of MVA 48 encoded by SEQ ID NO:5 and the truncated ADA envelope of MVA 48 encoded by SEQ ID NO:3.

3. A pharmaceutical composition comprising the recombinant MVA of claim 1 or claim 2 and a pharmaceutically acceptable carrier.

4. A pharmaceutical composition comprising the recombinant MVA of claim 2 and a pharmaceutically acceptable carrier.

* * * * *

UNITED STATES PATENT AND TRADEMARK OFFICE
CERTIFICATE OF CORRECTION

Page 1 of 1

PATENT NO. : 8,916,172 B2
APPLICATION NO. : 12/987791
DATED : December 23, 2014
INVENTOR(S) : Bernard Moss et al.

It is certified that error appears in the above-identified patent and that said Letters Patent is hereby corrected as shown below:

In the specification,

Column 1, line 3, immediately below the title of the application, please insert the following:

--ACKNOWLEDGEMENT

This invention was made with government support under Grant No. AI49364 awarded by the National Institutes of Health. The Government has certain rights in the invention.--

Signed and Sealed this
Twenty-second Day of December, 2015

Michelle K. Lee
*Director of the United States Patent and Trademark Office*